US007666656B2

(12) United States Patent
Sun et al.

(10) Patent No.: US 7,666,656 B2
(45) Date of Patent: Feb. 23, 2010

(54) RECOMBINANT BCG STRAINS WITH ENHANCED ABILITY TO ESCAPE THE ENDOSOME

(75) Inventors: Ronggai Sun, Ellicott City, MD (US); David Michael Hone, Rockville, MD (US); Jerald C. Sadoff, Washington, DC (US)

(73) Assignee: Aeras Global TB Vaccine Foundation, Bethesda, MD (US)

( * ) Notice: Subject to any disclaimer, the term of this patent is extended or adjusted under 35 U.S.C. 154(b) by 139 days.

(21) Appl. No.: 11/755,936

(22) Filed: May 31, 2007

(65) Prior Publication Data

US 2008/0095794 A1   Apr. 24, 2008

Related U.S. Application Data

(63) Continuation-in-part of application No. 11/578,124, filed as application No. PCT/US2005/042602 on Nov. 23, 2005, application No. 11/755,936, which is a continuation-in-part of application No. 11/284,895, filed on Nov. 23, 2005, now abandoned, and a continuation-in-part of application No. PCT/US2005/042602.

(60) Provisional application No. 60/631,973, filed on Dec. 1, 2004.

(51) Int. Cl.
    *C12N 1/12*   (2006.01)
(52) U.S. Cl. ............... 435/253.1; 435/252.3; 424/93.2; 424/93.4; 424/248.1
(58) Field of Classification Search ............... None
    See application file for complete search history.

(56) References Cited

U.S. PATENT DOCUMENTS

| 5,731,151 | A | 3/1998 | King et al. | |
| 6,423,545 | B1 | 7/2002 | Pavelka, Jr. et al. | |
| 6,471,967 | B1 * | 10/2002 | Horwitz et al. | 424/248.1 |
| 6,673,353 | B1 * | 1/2004 | Kaufmann et al. | 424/200.1 |
| 6,924,118 | B2 * | 8/2005 | Horwitz et al. | 424/9.1 |

FOREIGN PATENT DOCUMENTS

WO   WO 2006/060332 A2   12/2004

OTHER PUBLICATIONS

Wiker et al (Microbiological Reviews, 56(4):648-661, 1992).*
Jones et al (Molecular Microbiology, 21(6):1219-1225, 1996).*
Zhang et al (Plant Journal 33(4) abstract 2003).*
K. Edwards, et al. "Iron-Cofactored Superoxide Dismutase Inhibits Host Responses to Mycobacterium Tuberculosis", American Journal of Respiratory and Critical Care Medicine, vol. 164. 2001. pp. 2213-2219.
D. O'Brien et al. "Effects of *Clostridium perfingens* Alpha-Toxin (PLC) and Perfringolysin O (PFO) on Cytotoxicity to Macrophages, on Escape from the Phagosomes of Macrophages, and on Persistence of C. perfringens in Host Tissues", Infection and Immunity, vol. 72, No. 9. Sep. 2004, pp. 5204-5215.
S. Jones, et al. "Characterization of Listeria Monocytogenes Pathogenesis in a Stain Expressing Perfringolysin O in Place of Listeriolysin O", Infection and Immunity, vol. 62, No. 12. Dec. 1994. pp. 5608-5613.
S. Snapper, et al. "Lysogeny and Transformation in Mycobacteria: Stable Expression Foreign Genes", Proc. Natl. Acad. Sci. vol. 85, Sep. 1988. pp. 6987-6991.
J. Hess, et al. "*Mycobacterium bovis* Bacille Calamette-Guerin Strains Secreting Listerolysin of Listeria Monocytogens", Proc. Natl. Adcad. Sci. vol. 95. pp. 5299-5304, Apr. 1998.
D. Portnoy, et al. "Capacity of Listeriolysin O, Streptolysin O, and Perfringolysin O to Mediate Growth of *Bacillus subtilis* within MammalianCells",Infection and Immunity, vol. 60, No. 7. Jul. 1992. pp. 2710-2717.

* cited by examiner

*Primary Examiner*—Patricia A Duffy
(74) *Attorney, Agent, or Firm*—Whitham Curtis Christofferson & Cook, PC

(57) ABSTRACT

*Mycobacterium* strains that have an enhanced ability to elicit a MHC-Class I-restricted CD8+ T cell immune response are provided. The *Mycobacterium* strains are genetically engineered to express: a endosomolytic protein that is active at neutral pH (e.g. Perfringolysin O), permitting escape of the *Mycobacterium* from endosomes into the cytoplasm of the cell; and antigens of interest, such as tuberculosis antigens. The invention also provides vaccine preparations containing such *Mycobacterium* strains.

Figure 1:
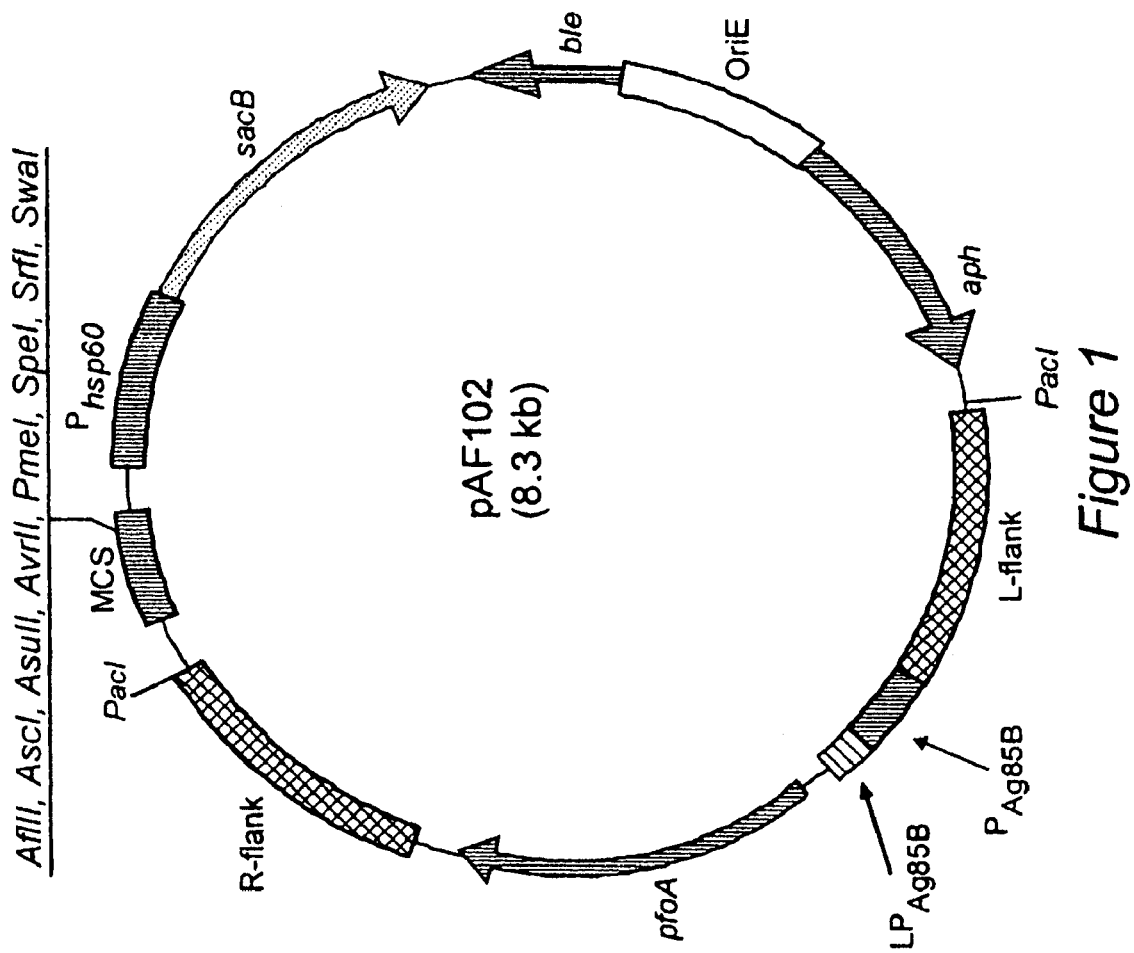

27 Claims, 29 Drawing Sheets atgataagatttaagaaaacaaaattaatagcaagtattgcaatggctttatgtctgttttctcaaccagtaatcagtttctcaaaggatataacaga
taaaaatcaaagtattgattctggaatatcaagcttaagttacaatagaaatgaagttttagctagtaatggagataaaattgaaagttttgttccaa
aggaaggtaaaaagactggtaataaaatttatagttgtagaacgtcaaaaaagatcccttacaacatcaccagtagatatatcaataattgattctg
taaatgaccgtacatatccaggagcattacaacttgcagataaagcctttgtggaaaatagacctacaatcttaatggtaaaaagaaagcctatt
aacattaatatagatttaccaggattaaaggggtgaaaatagtataaaggttgatgatccaacctatggaaaagtttctggagcaattgatgag
ttagtgtctaagtggaatgaaaagtattcatctacacatactttaccagcaagaactcaatattcagaatctatggtttatagtaaatcacaaatatc
aagtgcccttaatgttaatgctaaagtccttgaaaactcacttggagtagactttaatgcagtagcaaacaatgagaaaaaagttatgattttagc
atataaacaaatattctatacagtaagtgcagacttacctaagaatccatcagatcttttgatgacagtgttacatttaatgatttaaaacaaaagg
gagtaagtaatgaagcacctccacttatggtttcaaatgtagcttatggaagaactatatatgttaagttagaaactacttctagtagtaaagatgt
acaagctgctttcaaagctcttataaagaacactgatataaaaaatagtcaacaatataaagatatttatgaaaatagttccttcacagcagtagtt
ttaggaggagatgcacaagaacataacaaagttgtaactaaggactttgatgaaataagaaaagtaattaaagacaatgcaactttagtacaa
aaaacccagcatatccaatatcttatactagtgttttcttaaaagataactcagttgctgctgttcacaataaaacagattatatagaaacaacttct
acagagtattctaagggaaaaataaacttagatcatagtggagcctatgttgcacagtttgaagtagcatgggatgaagtttcatatgacaaaga
aggaaatgaagttttaactcataaaacatgggatggaaattatcaagataaaacagctcactattcaacagtaatacctcttgaagccaatgcaa
gaaatataagaataaaggcaagagagtgtacaggtcttgcttgggaatggtggagagatgttataagtgaatatgatgttccattaacaaataat
ataaatgtttcaatatggggaactactttatacccctggatctagtattacttacaattaa

```
AAG GAT ATC ACC GAC AAG AAC CAG AGC ATC GAT AGC GGC ATC TCC AGC
CTG TCG TAC AAC CGC GAA GTG CTA GCC TCG AAC GGC GAC AAG ATC
GAA AGC TTC GTT CCG AAG GAG GGT AAG AAG ACG GGT AAT AAG TTC ATC
GTC GTA GAA CGT CAG AAG CGA TCC TTG ACC ACG TCG CCA GTC GAT ATC
AGC ATC ATT GAT TCG GTG AAC GAC CGG ACC TAT CCG GGC GCA CTG CAA CTT
GCC GAC AAA GCC TTT GTG GAA AAC CGC CCG ACC ATC CTA ATG GTG AAG CGC
AAG CCG ATC AAC ATT AAC GAC CTG CCG CAG CTG AAG GGT GAG AAC
TCG ATC AAG GTG GAC GAC CCG ACC TAT GGC AAG GTG TCC GGC GCG ATC
GAC GAG CTG GTG TCG AAG TGG AAC GAG AAG TAT TCA TCC ACC CAT ACT CTC
CCA GCG CGG ACC CAG TAT TCA GAG AGC ATG GTC TAC TCG AAG TCC CAG
ATA TCA AGT GCC CTG AAT GTG AAT GCT AAG GTC CTG GAA AAC TCG CTG
GGC GTG GAC TTT AAC GCA GTA GCG AAC AAC GAG AAG AAG GTG ATG ATT
TTG GCC TAC AAA CAA ATC TTC TAT ACG GTG TCG GCG GAC CTG CCC AAG AAC
CCC AGC GAC CTG TTC GAC GAC TCG GTT ACG TTC AAC GAC CTC AAG CAG AAG
GGG GTG AGC AAT GAG GCG CCT CCG ATG GTC TCG AAC GTG GCC TAC
GGA CGG ACG ATC TAC GTC AAG TTA GAA ACC ACC TCT TCC TCG AAG GAC
GTC CAG GCC GCC TTC AAA GCC CTG ATC AAG AAC CTG ATC AAG AAC TCC
CAG CAG TAC AAG GAC ATT TAC GAG AAT TCG TCC TTC ACC GCG GTC GTC TTG
GGC GGC GAT GCG CAG GAA CAC AAC AAA GTG GTC ACC AAG GAC TTC GAT
GAG ATA CGG AAA GTC ATT AAG GAC AAC GCG ACT TTC TCC ACA AAA AAC
CCG GCA TAC CCG ATC AGC TAT ACC AGT GTG TTC CTC AAG GAC AAC AGC GTC
GCC GCT GTT CAC AAC AAG GAC TAC ATC GAC ACG ACC TCG ACC GAG TAC
AGC AAG GGG AAA ATC AAC CTG GAT CAC TCG GGC GCC TCG GTT GCC CAG
TTC GAG GTG GCC TGG GAC GAA GTC GAC TAT GAC AAG GAG GGC AAT GAA
GTG CTC ACG CAC AAA ACG TGG GAC GGG AAC TAC CAA GAT AAG ACA GCC
CAC TAC TCA ACC GTG ATC CCC CTC GAG GCC AAC GCG AGG AAC ATC CGC
ATC AAG GCG CGG GAG TGC ACG GGT CTT GCG TGG GAG TGG TGG CGC GAC
GTC ATC TCG GAG TAC GAC GTG CCG TTG ACC AAC AAC ATC AAT GTG AGC ATC
TGG GGA ACC ACC CTG TAC CCC GGG TCG TCG ATC ACC TAC AAC TGA
```

*Figure 3*

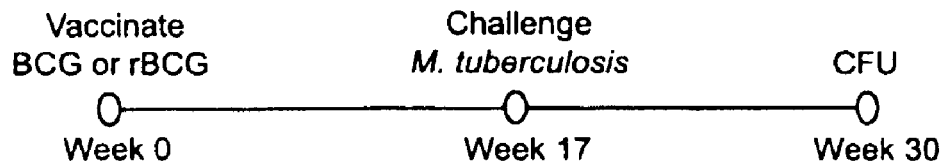
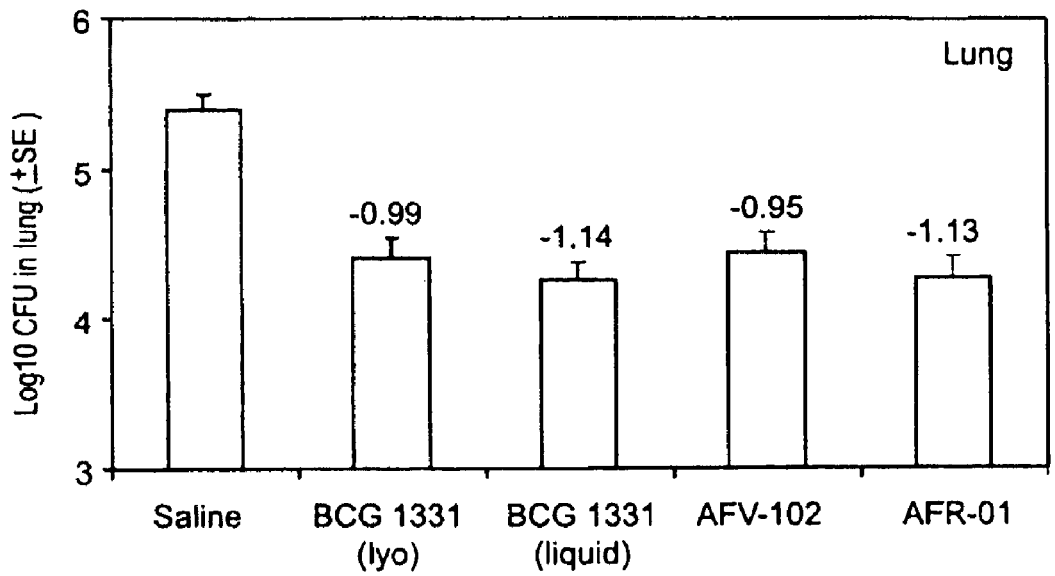
Figure 15A
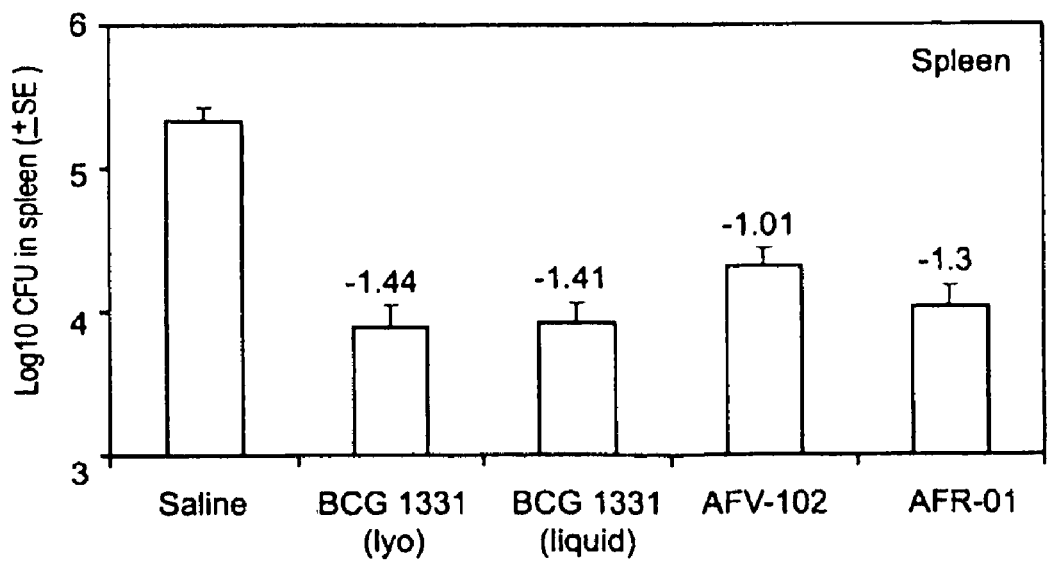
Figure 15B

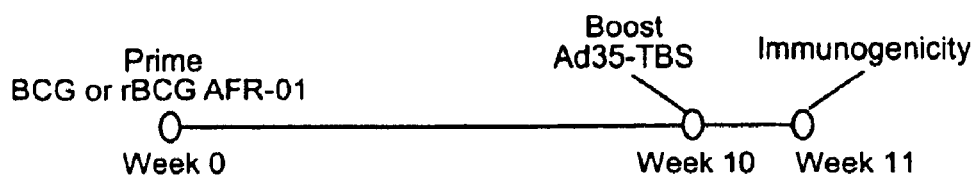
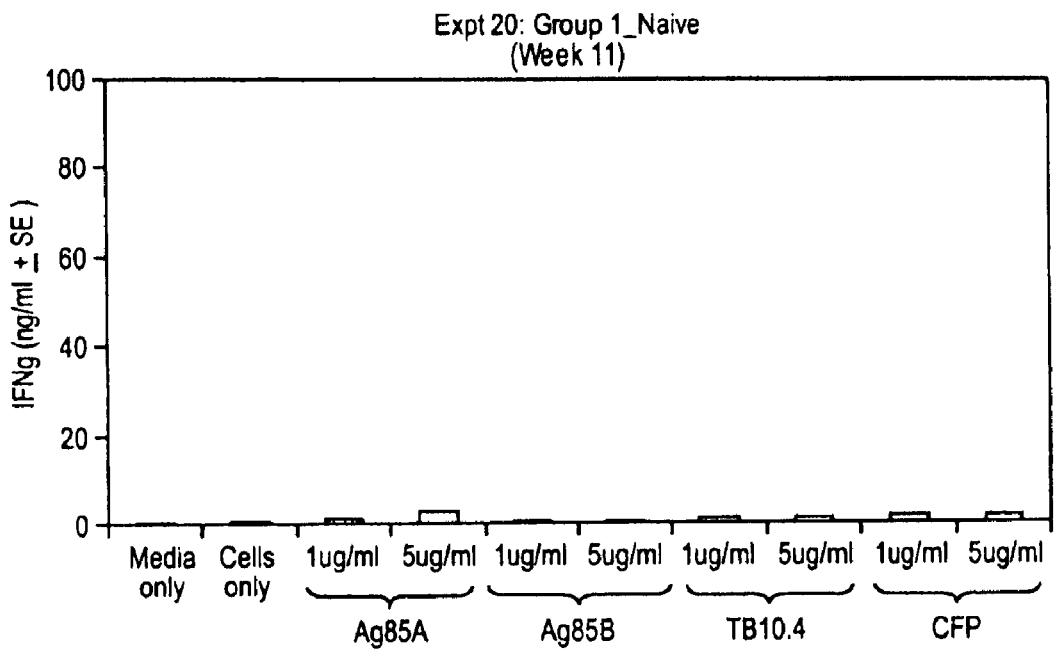
*Figure 18A*
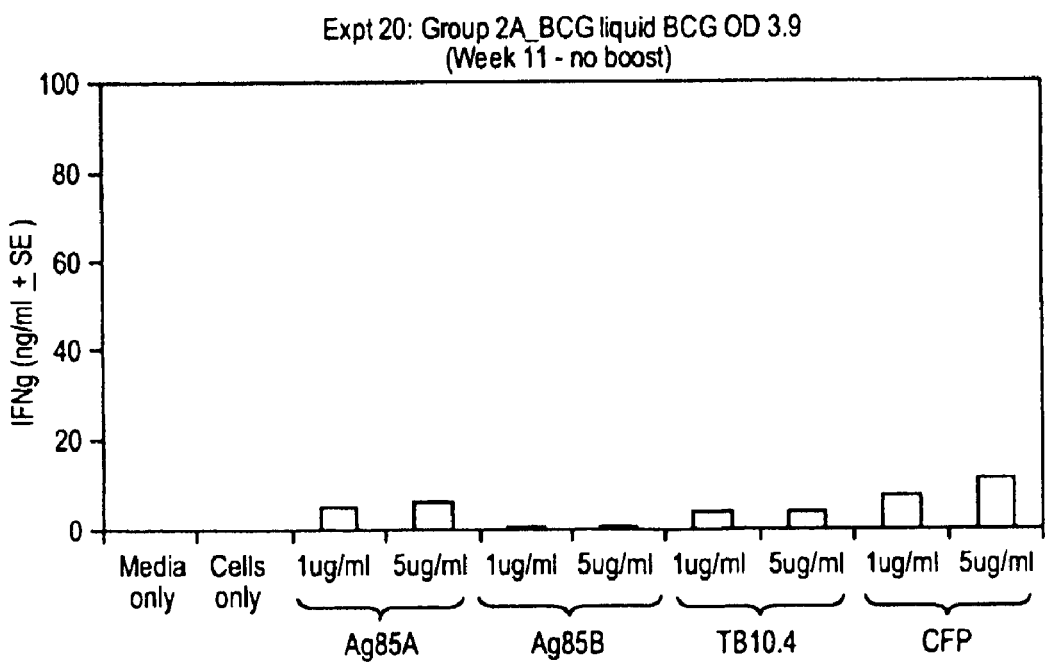
*Figure 18B*

| Group | Prime Wk0 | Boost-1 Wk14 | Boost-2 Wk18 | Boost-3 Wk26 |
|---|---|---|---|---|
| 1 n=6 | BCG (SSI-1331)[1] 2 x 10^5 CFU i.d. (0.1 ml) | Aeras-402[3] (3 x 10^10 vp) i.m. (1.0 ml) | Saline | Aeras-402[3] (3 x 10^10 vp) i.m. (1.0 ml) |
| 2 n=6 | rBCG (AFR0-1)[2] 2 x 10^5 CFU i.d. (0.1 ml) | Aeras-402[3] (3 x 10^10 vp) i.m. (1.0 ml) | Saline | Aeras-402[3] (3 x 10^10 vp) i.m. (1.0 ml) |
| 3 n=6 | BCG (SSI-1331)[1] 2 x 10^5 CFU i.d. (0.1 ml) | Aeras-402[3] (3 x 10^10 vp) i.m. (1.0 ml) | HyVac4:IC31[4] (50 µg in 500nmol IC31) i.m. (0.5 ml) | HyVac4:IC31[4] (50 µg in 500nmol IC31) i.m. (0.5 ml) |
| 4 n=6 | BCG (SSI-1331)[1] 2 x 10^5 CFU i.d. (0.1 ml) | Saline | HyVac4:IC31[4] (50 µg in 500nmol IC31) i.m. (0.5 ml) | HyVac4:IC31[4] (50 µg in 500nmol IC31) i.m. (0.5 ml) |
| 5 n=3 | Saline | Saline | Saline | Saline |

| Group | Prime Wk0 | Boost-1 Wk4 | Boost-2 Wk12 |
|---|---|---|---|
| 6 n=6 | Aeras-402[3] (3 x 10^10 vp) i.m. (1.0 ml) | HyVac4:IC31[4] (50 µg in 500nmol IC31) i.m. (0.5 ml) | HyVac4:IC31[4] (50 µg in 500nmol IC31) i.m. (0.5 ml) |

*Figure 21A*

SEQUENCE LISTING

<160> NUMBER OF SEQ ID NOS: 5

<210> SEQ ID NO 1
<211> LENGTH: 1503
<212> TYPE: DNA
<213> ORGANISM: Clostridium perfringens

<400> SEQUENCE: 1

```
atgataagat ttaagaaaac aaaattaata gcaagtattg caatggcttt atgtctgttt      60
tctcaaccag taatcagttt ctcaaaggat ataacagata aaaatcaaag tattgattct     120
ggaatatcaa gcttaagtta caatagaaat gaagttttag ctagtaatgg agataaaatt     180
gaaagttttg ttccaaagga aggtaaaaag actggtaata aatttatagt tgtagaacgt     240
caaaaaagat cccttacaac atcaccagta gatatatcaa taattgattc tgtaaatgac     300
cgtacatatc caggagcatt acaacttgca gataaagcct ttgtggaaaa tagacctaca     360
atcttaatgg taaaaagaaa gcctattaac attaatatag atttaccagg attaaagggt     420
gaaaatagta taaaggttga tgatccaacc tatggaaaag tttctggagc aattgatgag     480
ttagtgtcta agtggaatga aaagtattca tctacacata ctttaccagc aagaactcaa     540
tattcagaat ctatggttta tagtaaatca caaatatcaa gtgcccttaa tgttaatgct     600
aaagtccttg aaaactcact tggagtagac tttaatgcag tagcaaacaa tgagaaaaaa     660
gttatgattt tagcatataa acaaatattc tatacagtaa gtgcagactt acctaagaat     720
ccatcagatc tttttgatga cagtgttaca tttaatgatt taaaacaaaa gggagtaagt     780
aatgaagcac ctccacttat ggtttcaaat gtagcttatg gaagaactat atatgttaag     840
ttagaaacta cttctagtag taaagatgta caagctgctt tcaaagctct tataaagaac     900
actgatataa aaaatagtca acaatataaa gatatttatg aaaatagttc cttcacagca     960
gtagttttag gaggagatgc acaagaacat aacaaagttg taactaagga ctttgatgaa    1020
ataagaaaag taattaaaga caatgcaact tttagtacaa aaaacccagc atatccaata    1080
tcttatacta gtgtttttctt aaaagataac tcagttgctg ctgttcacaa taaaacagat    1140
tatatagaaa caacttctac agagtattct aagggaaaaa taaacttaga tcatagtgga    1200
gcctatgttg cacagtttga agtagcatgg gatgaagttt catatgacaa agaaggaaat    1260
gaagttttaa ctcataaaac atgggatgga aattatcaag ataaaacagc tcactattca    1320
acagtaatac ctcttgaagc caatgcaaga aatataagaa taaaggcaag agagtgtaca    1380
ggtcttgctt gggaatggtg gagagatgtt ataagtgaat atgatgttcc attaacaaat    1440
aatataaatg tttcaatatg gggaactact ttatacctg atctagtat tacttacaat    1500
taa                                                                 1503
```

<210> SEQ ID NO 2
<211> LENGTH: 500
<212> TYPE: PRT
<213> ORGANISM: Clostridium perfringens

<400> SEQUENCE: 2

```
Met Ile Arg Phe Lys Lys Thr Lys Leu Ile Ala Ser Ile Ala Met Ala
1               5                   10                  15

Leu Cys Leu Phe Ser Gln Pro Val Ile Ser Phe Ser Lys Asp Ile Thr
            20                  25                  30

Asp Lys Asn Gln Ser Ile Asp Ser Gly Ile Ser Ser Leu Ser Tyr Asn
            35                  40                  45

Arg Asn Glu Val Leu Ala Ser Asn Gly Asp Lys Ile Glu Ser Phe Val
        50                  55                  60

Pro Lys Glu Gly Lys Lys Thr Gly Asn Lys Phe Ile Val Val Glu Arg
65                  70                  75                  80

Gln Lys Arg Ser Leu Thr Thr Ser Pro Val Asp Ile Ser Ile Ile Asp
                85                  90                  95

Ser Val Asn Asp Arg Thr Tyr Pro Gly Ala Leu Gln Leu Ala Asp Lys
                100                 105                 110

Ala Phe Val Glu Asn Arg Pro Thr Ile Leu Met Val Lys Arg Lys Pro
            115                 120                 125

Ile Asn Ile Asn Ile Asp Leu Pro Gly Leu Lys Gly Glu Asn Ser Ile
130                 135                 140

Lys Val Asp Asp Pro Thr Tyr Gly Lys Val Ser Gly Ala Ile Asp Glu
145                 150                 155                 160

Leu Val Ser Lys Trp Asn Glu Lys Tyr Ser Ser Thr His Thr Leu Pro
                165                 170                 175

Ala Arg Thr Gln Tyr Ser Glu Ser Met Val Tyr Ser Lys Ser Gln Ile
                180                 185                 190

Ser Ser Ala Leu Asn Val Asn Ala Lys Val Leu Glu Asn Ser Leu Gly
            195                 200                 205

Val Asp Phe Asn Ala Val Ala Asn Asn Glu Lys Lys Val Met Ile Leu
        210                 215                 220

Ala Tyr Lys Gln Ile Phe Tyr Thr Val Ser Ala Asp Leu Pro Lys Asn
225                 230                 235                 240

Pro Ser Asp Leu Phe Asp Asp Ser Val Thr Phe Asn Asp Leu Lys Gln
                245                 250                 255

Lys Gly Val Ser Asn Glu Ala Pro Pro Leu Met Val Ser Asn Val Ala
                260                 265                 270

Tyr Gly Arg Thr Ile Tyr Val Lys Leu Glu Thr Thr Ser Ser Ser Lys
            275                 280                 285

Asp Val Gln Ala Ala Phe Lys Ala Leu Ile Lys Asn Thr Asp Ile Lys
        290                 295                 300

Asn Ser Gln Gln Tyr Lys Asp Ile Tyr Glu Asn Ser Ser Phe Thr Ala
305                 310                 315                 320

Val Val Leu Gly Gly Asp Ala Gln Glu His Asn Lys Val Val Thr Lys
                325                 330                 335

Asp Phe Asp Glu Ile Arg Lys Val Ile Lys Asp Asn Ala Thr Phe Ser
                340                 345                 350

Thr Lys Asn Pro Ala Tyr Pro Ile Ser Tyr Thr Ser Val Phe Leu Lys
            355                 360                 365

Asp Asn Ser Val Ala Ala Val His Asn Lys Thr Asp Tyr Ile Glu Thr
        370                 375                 380

Thr Ser Thr Glu Tyr Ser Lys Gly Lys Ile Asn Leu Asp His Ser Gly
385                 390                 395                 400

Ala Tyr Val Ala Gln Phe Glu Val Ala Trp Asp Glu Val Ser Tyr Asp
                405                 410                 415
```

-continued

```
Lys Glu Gly Asn Glu Val Leu Thr His Lys Thr Trp Asp Gly Asn Tyr
                420                 425                 430
Gln Asp Lys Thr Ala His Tyr Ser Thr Val Ile Pro Leu Glu Ala Asn
            435                 440                 445
Ala Arg Asn Ile Arg Ile Lys Ala Arg Glu Cys Thr Gly Leu Ala Trp
        450                 455                 460
Glu Trp Trp Arg Asp Val Ile Ser Glu Tyr Asp Val Pro Leu Thr Asn
465                 470                 475                 480
Asn Ile Asn Val Ser Ile Trp Gly Thr Thr Leu Tyr Pro Gly Ser Ser
                485                 490                 495
Ile Thr Tyr Asn
            500
```

<210> SEQ ID NO 3
<211> LENGTH: 1419
<212> TYPE: DNA
<213> ORGANISM: Clostridium perfringens

<400> SEQUENCE: 3

| | | | |
|---|---|---|---|
| aaggatatca ccgacaagaa ccagagcatc gatagcggca tctccagcct gtcgtacaac | 60 |
| cgcaacgaag tgctagcctc gaacggcgac aagatcgaaa gcttcgttcc gaaggagggt | 120 |
| aagaagacgg gtaataagtt catcgtcgta aacgtcaga agcgatcctt gaccacgtcg | 180 |
| ccagtcgata tcagcatcat tgattcggtg aacgaccgga cctatccggg cgcactgcaa | 240 |
| cttgccgaca aagcctttgt ggaaaaccgc ccgaccatcc taatggtgaa gcgcaagccg | 300 |
| atcaacatta acatcgacct gccgcagctg aagggtgaga actcgatcaa ggtggacgac | 360 |
| ccgacctatg gcaaggtgtc cggcgcgatc gacgagctgg tgtcgaagtg aacgagaag | 420 |
| tattcatcca cccatactct cccagcgcgg acccagtatt cagagagcat ggtctactcg | 480 |
| aagtcccaga tatcaagtgc cctgaatgtg aatgctaagg tcctggaaaa ctcgctgggc | 540 |
| gtggacttta acgcagtagc gaacaacgag aagaaggtga tgattttggc ctacaaacaa | 600 |
| atcttctata cggtgtcggc ggacctgccc aagaacccca gcgacctgtt cgacgactcg | 660 |
| gttacgttca acgacctcaa gcagaagggg gtgagcaatg aggcgcctcc gctgatggtc | 720 |
| tcgaacgtgg cctacggacg gacgatctac gtcaagttag aaaccacctc ttcctcgaag | 780 |
| gacgtccagg ccgccttcaa agccctgatc aagaacaccg acatcaagaa ctcccagcag | 840 |
| tacaaggaca tttacgagaa ttcgtccttc accgcggtcg tcttgggcgg cgatgcgcag | 900 |
| gaacacaaca aagtggtcac caaggacttc gatgagatac ggaaagtcat taaggacaac | 960 |
| gcgactttct ccacaaaaaa cccggcatac ccgatcagct ataccagtgt gttcctcaag | 1020 |
| gacaacagcg tcgccgctgt tcacaacaag accgactaca tcgagacgac ctcgaccgag | 1080 |
| tacagcaagg ggaaaatcaa cctggatcac tcgggcgcct acgttgccca gttcgaggtg | 1140 |
| gcctgggacg aagtcagcta tgacaaggag ggcaatgaag tgctcacgca aaaacgtgg | 1200 |
| gacgggaact accaagataa gacagcccac tactcaaccg tgatccccct cgaggccaac | 1260 |
| gcgaggaaca tccgcatcaa ggcgcgggag tgcacgggtc ttgcgtggga gtggtggcgc | 1320 |
| gacgtcatct cggagtacga cgtgccgttg accaacaaca tcaatgtgag catctgggga | 1380 |
| accacccctgt acccggggtc gtcgatcacc tacaactga | 1419 |

<210> SEQ ID NO 4
<211> LENGTH: 19
<212> TYPE: DNA
<213> ORGANISM: Artificial

-continued

```
<220> FEATURE:
<223> OTHER INFORMATION: synthetic forward oligonucleotide primer

<400> SEQUENCE: 4
acggctaccg tctggacat                                                19

<210> SEQ ID NO 5
<211> LENGTH: 18
<212> TYPE: DNA
<213> ORGANISM: Artificial
<220> FEATURE:
<223> OTHER INFORMATION: synthetic reverse oligonucleotide primer

<400> SEQUENCE: 5
cgatggcttc ttcgatgc                                                 18
```

RECOMBINANT BCG STRAINS WITH ENHANCED ABILITY TO ESCAPE THE ENDOSOME

This application is a continuation-in-part of and claims benefit of co-pending U.S. patent application Ser. No. 11/578,124 (Feb. 21, 2009) which is a 371 of International patent application PCT/U.S. 2005/042602 (filed Nov. 23, 2005), which in turn claims priority to U.S. provisional patent application 60/631,973 (filed Dec. 1, 2004). This application is also a continuation-in-part of and claims benefit of U.S. patent application Ser. No. 11/284,895 (Nov. 23, 2005), now abandoned, which also claims priority to U.S. provisional patent application 60/631,973 (filed Dec. 1, 2004). This application is also a continuation-in-part and claims benefit of International patent application PCT/U.S. 2005/042602 (filed Nov. 23, 2005), which in turn claims priority to U.S. provisional patent application 60/631,973 (filed Dec. 1, 2004). The complete contents of each of these applications are hereby incorporated by reference.

BACKGROUND OF THE INVENTION

1. Field of the Invention

The invention provides *Mycobacterium* strains that have an enhanced ability to elicit an immune response. In vivo experiments have demonstrated, for example, a Major Histocompatibility Complex Class I-restricted $CD8^+$ T cell immune response. In particular, the invention provides *Mycobacterium* strains that express a Perfringolysin O (PfoA) protein that permits escape of the *Mycobacterium* from endosomes, and vaccine preparations containing the *Mycobacterium* strains.

2. Background

*Mycobacterium tuberculosis* (M. tb) has infected one-third of the world's population, causing active disease in 8 million and killing 1.6-2.2 million individuals every year, most of whom live in the developing world. Tuberculosis (TB) is an epidemic of global proportions that is growing and becoming even more deadly as it intersects with the spread of HIV. TB is the number one killer of people with AIDS.

Bacille Calmette Guerin (BCG), an attenuated strain of *Mycobacterium bovis* and the current most widely used TB vaccine, was developed over 80 years ago and when tested has had widely variable rates of efficacy against pulmonary tuberculosis, including no efficacy in the last large field trial conducted in India (Fine et al., Vaccine, 16(20): 1923-1928; 1998; Anonymous, Indian J Med Res., August; 110:56-69; 1999. Nonetheless, The World Health Organization currently recommends BCG at birth or first contact with health services for all children (except those with symptoms of HIV disease/AIDS) in high TB prevalent countries. This policy is based on evidence that BCG protects against serious childhood forms of TB (Lanckriet et al., Int J Epidemiol, 24(5): 1042-1049; 1995; Rodrigues et al., J Epidemiol Community Health 45(1): 78-80; 1991. Protection by BCG against TB beyond early childhood is a controversial subject with limited data giving mixed results. The high incidence of pediatric and adult TB in developing countries where infant BCG immunization is widely practiced, however, indicates that BCG as currently administered is not highly efficacious over the many years when people are at risk of TB disease. Thus, BCG is considered to be an inadequate public health tool for the intervention and control of TB.

Approximately 70 percent of humans exposed to TB organisms, and who have normal immune systems, do not become infected, and of those that do become infected only about 5 percent develop disease within the first two years. The majority of infected individuals suppress the infection, which is associated with the development of robust cellular immune responses to M. tb antigens. An additional 5 percent later reactivate when immunity declines. Both primary and reactivation disease are much more common in people with HIV/AIDS, again emphasizing the role of immunity in preventing and controlling infection.

Because most humans are able to control TB, there is good reason to hope that by inducing long lasting immunity of the appropriate kind, it should be possible to develop effective vaccines that prevent initial infection after exposure, prevent early progression to disease, prevent reactivation from the latent state, and prevent relapse after treatment. Ultimately, it is the combination of systematic vaccine use plus chemotherapeutic intervention that will eventually eliminate M. tb as a human pathogen.

In light of the critical role childhood BCG vaccination is thought to play in preventing acute TB, it is difficult to replace BCG in trials to evaluate candidate TB vaccines without overwhelming evidence that the new TB vaccine is a superior product. The problem is that M. tb is a human-specific pathogen and animal models only mimic parts of the host-pathogen interaction. Thus, definitive evidence that a new TB vaccine possesses improved potency can only be obtained from controlled field trials in humans. This reality has led many investigators to conclude that a key step toward an improved TB vaccine will be to enhance the immunogenicity of BCG.

One example of such a strategy is to improve the capacity of BCG to induce or activate T cells for enhancing the immune response. The pivotal role of major histocompatibility complex class I-restricted $CD8^+$ T cells in immunity to M. tb is demonstrated by the failure of $\beta$2-microglobulin ($\beta$2m)-deficient mice to control experimental M. tb infection (Flynn et al., PNAS USA, 89(24): 12013-12017; 1992). The pivotal role of Major Histocompatibility Complex class I-restricted $CD8^+$ T cells was convincingly demonstrated by the failure of $\beta$2-microglobulin ($\beta$2m) deficient mice to control experimental *M. tuberculosis* infection (Flynn et al., supra, 1992). Because these mutant mice lack Major Histocompatibility Complex class I, functional $CD8^+$ T cells cannot develop. In contrast to *M. tuberculosis* infection, $\beta$2m-deficient mice are capable of controlling certain infectious doses of the BCG vaccine strain (Flynn et al., supra, 1992; Ladel C. H., et al., Eur J Immunol, 25:377-384; 1995). Furthermore, BCG vaccination of $\beta$2m-deficient mice only prolonged survival after *M. tuberculosis* infection, whereas BCG-immunized C57BL/6 resisted *M. tuberculosis* (Flynn et al., supra, 1992).

This differential $CD8^+$ T cell dependency between *M. tuberculosis* and BCG may be explained as follows: *M. tuberculosis* antigens gain better access to the cytoplasm than antigens from BCG leading to more pronounced Major Histocompatibility Complex class I presentation (Hess and Kaufmann, FEMS Microbiol. Immunol 7:95-103; 1993). Consequently, a more effective CD8+ T cell response is generated by *M. tuberculosis*. This notion was recently supported by increased Major Histocompatibility Complex class I presentation of an irrelevant antigen, ovalbumin, by simultaneous *M. tuberculosis*, rather than BCG, infection of antigen presenting cells (APC) (Mazzaccaro et al., Proc Natl Acad Sci USA, October 15:93(21): 11786-91; 1996).

Thus, M. tb antigens access the host cell cytoplasm better than antigens from BCG, leading to increased Major Histocompatibility Complex (herein referred to as MHC) class I presentation (Hess et al., supra, 1993) and an elevated $CD8^+$ T cell response to M. tb. Further, M. tb stimulates antigen-specific MHC class II-restricted $CD4^+$ T helper cells as well as Major Histocompatibility Complex class I-restricted CD8+ cytotoxic T cells in mice and humans (Kaufmann, Annu Rev Immunol 11:129-163; 1993). By extension, this fact indicates that M. tb infected cells are susceptible to recognition by MHC class I-restricted CD8+ cytotoxic T cells. Given that 70 percent of immunocompetent humans exposed to TB organisms do not become infected, immunity induced by M. tb infection is highly effective in controlling this organism in the vast majority of instances. It is believed, therefore, that the efficacy of existing TB vaccine strain BCG will be improved by increasing the capacity of BCG to induce MHC class I-restricted CD8+ cytotoxic T cell responses (Kaufmann, Fundamental Immunology, 1997).

As a rule, antigens expressed by pathogens that remain phagosome-bound are primarily presented by MHC class II molecules to CD4+ T cells but are poorly recognized by CD8+ T cells, which normally recognize antigens presented in the context of MHC class I molecules (Kaufmann, supra, 1997). In contrast, intracellular bacteria, such as *Listeria monocytogenes* (e.g. ATCC #13932), that escape the phagosome and replicate in the cytoplasm of host cells are effective at accessing the MHC class I antigen presentation pathway and at eliciting CD8+ T cell responses (Berche et al., J Immunol, 138:2266-2276; 1987). This endosome escape function of *Listeria monocytogenes* was recently transferred into attenuated *Salmonella*, which normally resides in the phagosome, by introducing the sequences encoding listeriolysin (Llo); the resultant strains were shown to escape the endosome and were more effective at inducing CD8+ T cell responses (Bielecki et al., Nature (London), 354:175-176; 1990; Gentschev et al., Infect Immun 63(10): 4202-4205; 1995; Hess et al., Host Response to Intracellular Pathogens, 75-90; 1997). More recently this approach was applied to BCG; thus rBCG strains secreting Llo were constructed to improve the capacity of BCG to induce MHC class I-restricted immune responses (Hess et al., PNAS USA, 95(9): 5299-5304; 1998. Although early evidence suggested that a rBCG-Llo+ strain was more adept at eliciting CD8+ T cells, the strain proved to be incapable of escaping the endosome. Thus, a limitation of this approach is that the hemolytic function of Llo, which is required for endosome escape, is only fully active at pH 5.5 and almost inactive at pH 7.0. Since *Mycobacteria* maintain the pH of the endosome at a value of ca. 7.0, it is logical to surmise that Llo in rBCG-Llo strains thus far reported are dysfunctional because the environment in which they are expressed is suboptimal for hemolytic activity magnitude (Geoffroy et al., Infect Immun 55(7): 1641-1646; 1987). Thus, the immune-enhancing benefit of this approach will not be realized until a strategy is developed that enables Llo to function in BCG-manipulated endosomes.

The prior art has thus far failed to provide a rBCG with an increased capacity for endosomal escape, and which can thereby increase induction of, for example, Major Histocompatibility Complex class I-restricted CD8+ cytotoxic T cell responses.

SUMMARY OF THE INVENTION

An exemplary aspect of the present invention provides recombinant BCG (rBCG) strains that have an enhanced ability to elicit a MHC class I-restricted CD8+ T-cell immune response. These novel rBCG strains have been genetically engineered to express a functional endosomolytic protein that is bioactive at pH values near neutrality (e.g. about pH 6-8 or about 6.5 to 7.5). The endosomolytic protein is therefore active within *Mycobacteria*-containing endosomes, which typically have an internal pH near neutrality. The activity of the endosomolytic protein produced by the rBCG results in disruption of the endosome, permitting the rBCG to escape from the endosome and into the cytoplasm of the cell. The rBCG are thus exposed to the cytoplasm, and elicit a strong T-cell response, particularly a strong MHC-1-restricted CD8+ cytotoxic T cell response. In one embodiment of the invention, the endosomolytic protein that is introduced into the rBCG by genetic engineering is Perfringolysin O (PfoA) from *Clostridium perfringens*.

The invention thus provides a *Mycobacterium* that is genetically engineered to express and secrete a functional endosomolytic protein that is active at neutral pH. In some embodiments, the functional endosomolytic pore-forming protein is PfoA or the mutant PfoA encoded by SEQ ID NO: 3 (herein referred to as $PfoA_{G137Q}$). Expression of the functional endosomolytic protein by the *Mycobacterium* permits escape of the rBCG from endosomes. The *Mycobacterium* that is so genetically engineered may be an attenuated *Mycobacterium* such as BCG. The invention also provides: a *Mycobacterium* that is genetically engineered to express and secrete PfoA; and, a *Mycobacterium* that is genetically engineered to express and secrete a $PfoA_{G137Q}$ encoded by SEQ ID NO: 3.

The present invention further provides a method of enabling a *Mycobacterium* derivative to escape from endosomes. The method comprises the step of genetically engineering the *Mycobacterium* to contain, express and secrete a functional endosomolytic protein such as PfoA or $PfoA_{G137Q}$ such as that encoded by SEQ ID NO: 3. In some embodiments, the *Mycobacterium* is an attenuated *Mycobacterium* such as BCG.

The invention further provides a vaccine preparation, comprising a *Mycobacterium* that is genetically engineered to express and secrete a functional endosomolytic protein that is active at neutral pH. The functional endosomolytic protein may be, for example, PfoA or $PfoA_{G137Q}$ as encoded by SEQ ID NO: 3. Expression of the functional endosomolytic enzyme by the *Mycobacterium* permits escape of the recombinant *Mycobacterium* from endosomes. In some embodiments, the *Mycobacterium* is an attenuated *Mycobacterium* such as BCG.

In addition to the above, the invention also provides a recombinant *Mycobacterium* that is genetically engineered to include a) an expressible and secretable pfo protein; and b) nucleic acid sequences that encode one or more proteins of interest. In one embodiment, the one or more proteins of interest of interest include *Mycobacterium tuberculosis* (Mtb) antigens, examples of which include but are not limited to Ag85A, Ag85B and TB 10.4. In some embodiments, the nucleic acid sequences that encode one or more proteins of interest are present on a plasmid.

The invention also provides a method of enabling a *Mycobacterium* to escape from endosomes and express one or more proteins of interest. The method comprises the step of genetically engineering said *Mycobacterium* to: contain, express and secrete a functional endosomolytic protein; and contain and express one or more proteins of interest. In one embodiment, the one or more proteins of interest of interest include *Mycobacterium tuberculosis* (Mtb) antigens, examples of which include but are not limited to Ag85A, Ag85B and TB 10.4. In some embodiments, the nucleic acid sequences that encode one or more proteins of interest are present on a plasmid.

Figure 14A:
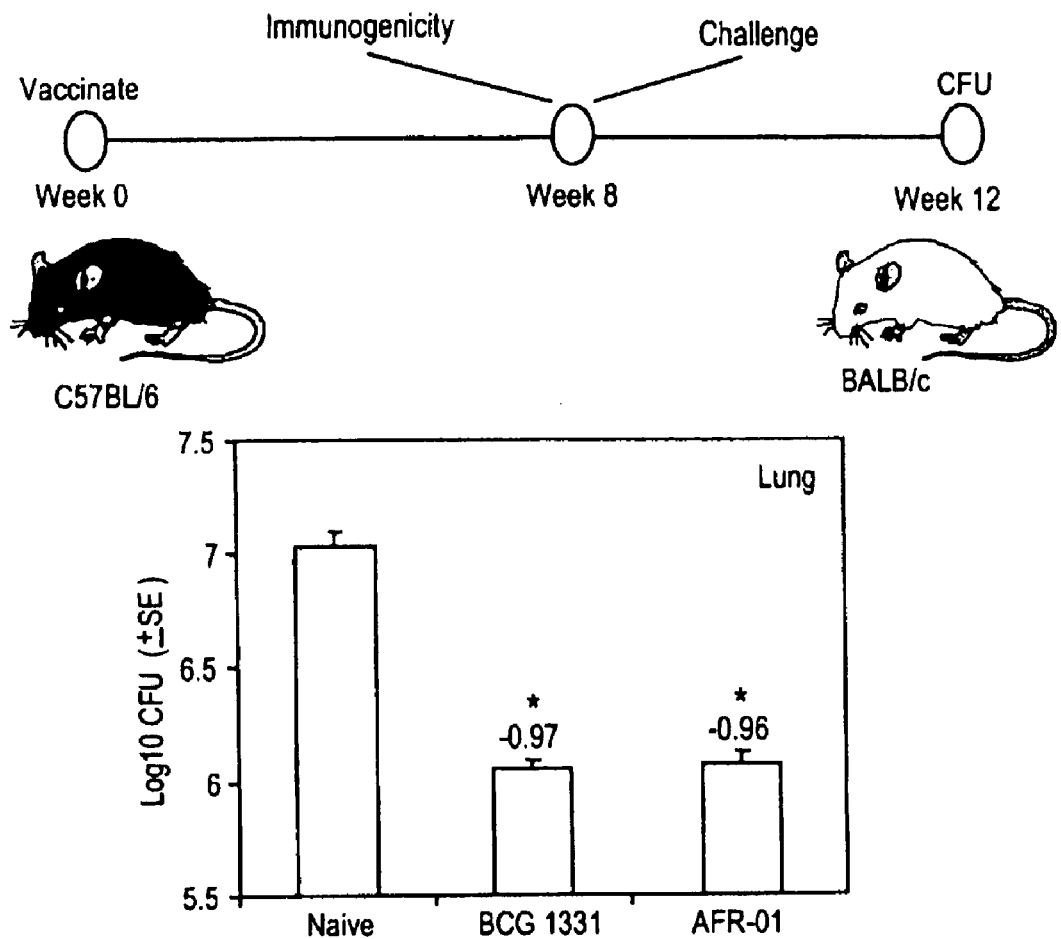
Figure 14B:
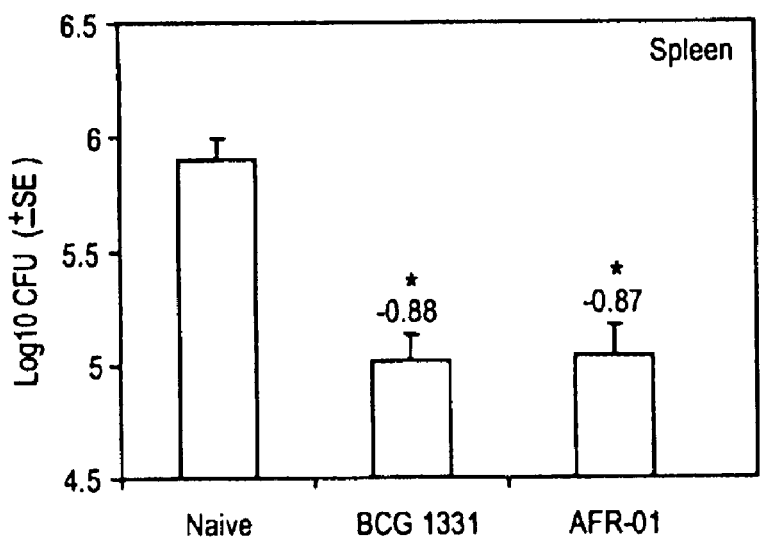
Figure 14C:
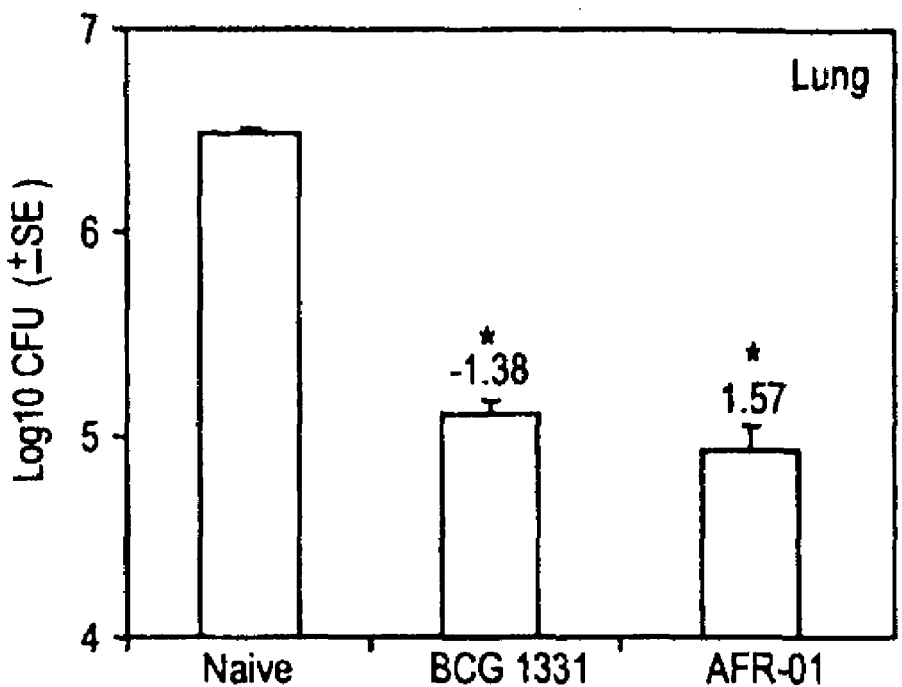
Figure 14D:
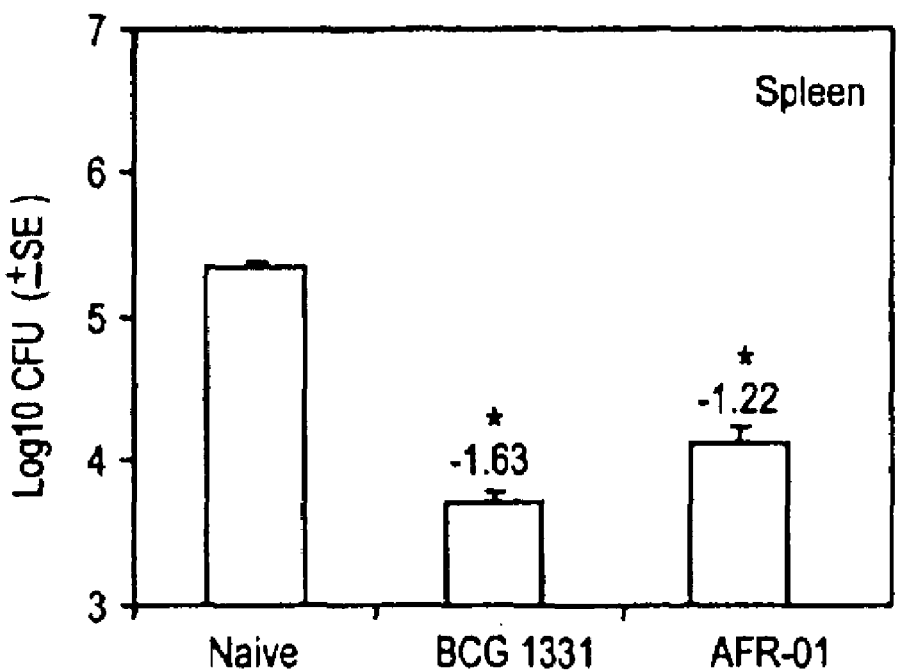

The invention further provides a vaccine preparation, comprising a recombinant *Mycobacterium* genetically engineered to: a) express and secrete a functional endosomolytic protein, wherein said functional endosomolytic protein is active at neutral pH; and b) express one or more proteins of interest. In one embodiment, the one or more proteins of interest include *Mycobacterium tuberculosis* (Mtb) antigens, examples of which include but are not limited to Ag85A, Ag85B and TB 10.4. In some embodiments, the nucleic acid sequences that encode one or more proteins of interest are present on a plasmid.

The invention further provides a method of vaccinating a mammal against *Mycobacterium tuberculosis* (Mtb). The method comprises the steps of administering to the mammal a first Mtb vaccine preparation; and administering to the mammal one or more additional Mtb vaccine preparations, At least one of the one or more additional Mtb vaccine preparations is heterologous (differs from the first vaccine composition), and at least one of the one or more additional Mtb vaccine preparations comprises a recombinant *Mycobacterium* genetically engineered to: a) express and secrete a functional endosomolytic protein (functional endosomolytic protein is active at neutral pH); and b) express one or more Mtb antigens. The one or more Mtb antigens may include but are not limited to Ag85A, Ag85B and TB 10.4.

BRIEF DESCRIPTION OF THE DRAWINGS

FIG. 1. The map for suicide vector pAF102. The denotation for each of the DNA segments as follow: L-flank and R-flank: left and right flanks of ureC gene respectively; pfoA is the gene encoding the mutant form of perfringolysin O (gene back accession number: BA000016) with a single amino acid change at 137G(Q); $LP_{PAg85B}$ is the DNA sequence encoding antigen 85B (i.e. Rv1886c) leader peptide; $P_{Ag85A}$ is the promoter sequence of antigen 85A gene (i.e. Rv3804c); aph is aminoglycoside phosphotransferase gene (gene bank accession number: X06402), which confers Kanamycin resistance for the plasmid; OriE is the pUC origin of replication (gene bank accession number: AY234331); Ble is the gene (gene bank accession number: L36850), which confers resistance to Zeocin for the plasmid; SacB is the gene (gene bank accession number: Y489048) encoding levansucrase, which confers bacterial sensitivity to sucrose; $P_{hsp60}$ is the promoter sequence of heat shock protein gene (i.e. Rv0440); MCS is the multiple cloning sites for the indicated restriction enzymes. Note that the cassette between two PacI sites can be replaced with other endosomolytic enzyme genes when applicable.

FIGS. 2A and B. A, The gene sequence of PfoA from *Clostridium perfringens* (SEQ ID NO: 1); B, the protein sequence of PfoA from *Clostridium* perfringens (SEQ ID NO: 2).

FIG. 3. The gene sequence of a preferred mutant, $PfoA_{G137Q}$ (SEQ ID NO: 3).

FIG. 4. Flow chart for the main steps of allele exchange.

FIG. 5. Restriction enzyme digestion for the allele exchange plasmid pAF102.

Lane 1:1 kb plus DNA ladder; Lane 2: Plasmid pAF102 digested by restriction enzyme EcoRI; Lane 3: Plasmid pAF102 undigested control; Lane 4: Vector plasmid pAF100 without PFO cassette insert digested by restriction enzyme EcoRI. Lane 5: Vector plasmid pAF100 without PFO cassette insert undigested control. From this figure, the plasmid pAF100 is linearized to produce a single band of 4.4 kb in size by the restriction enzyme EcoRI as expected. The plasmid pAF102 produced two bands with size of 2.3 kb and 6.0 kb respectively by restriction enzyme EcoRI as expected.

FIG. 6. PCR analysis of the selected colonies for the genotype of ΔureC::pfoA. The PCR was carried as descried in Materials and Methods. The PCR product was analyzed by gel electrophoresis in 1.2% agarose gel. The DNA ladder used was a 1 Kb plus DNA standard purchased from Invitrogen. Lanes 1-6: PCR for colonies Numbered 105-1 through 105-6 respectively; lane 7 and lane 8: PCR for colonies numbered 142-7 and 142-10, respectively. Lane 9: PCR for BCG Danish 1331 strain.

FIG. 7. Growth and kanamycin sensitivity of AFV-102. Bacteria from AFV-102, BCG Danish 1331 and PfoA construct merodiploid (Pfo105 MI) were inoculated into 7H9 growth media and the growth of each strain was compared by measuring the optical density at 600 nm at different time points. For the kanamycin sensitivity test, antibiotic was added to a final concentration of 50 ug/ml and the growth was measured as above. Abbreviations in the legend: Ctrl: control medium without any bacterial inoculation; +Kan or −Kan: with or without kanamycin in the medium.

FIG. 8. Cytotoxicity test for AFV-102 in J774A.1 cells. The cells were infected with either AFV-102 or BCG Danish 1331. At the indicated time points post infection, cell viability was measured as described in the Materials and Methods by comparison to the uninfected control.

FIG. 9. Testing AFV-102 for its survival ability in macrophages. J774A.1 monolayer cells were infected with AFV-102 or BCG Danish 1331, and at the indicated time points post infection the intracellular bacteria were enumerated as described in Materials and Methods.

FIG. 10. Test of AFV-102 for its ability to secrete Pfo protein with pH independent hemolytic activity. The AFV-102 culture was prepared as described previously and the supernatant was tested for its ability to lyse red cells at pH 7.0 and 5.5. The hemolysin activity was measured as described in Materials and Methods.

FIG. 11A-D. Schematic illustration of results for Example 3. A, The bacterium (darkened oval) invades a macrophage (gray oval) within a cell (hexagon) which stimulates formation of early endosomes; B, BCG halts endosome maturation and BCG is protected inside the early endosome; C, AFV-102 bacteria expressing PfoA are initially found in early endosomes after invasion; however, they will start to secrete PfoA and escape the endosome; D, AFV-102 bacteria expressing PfoA can be seen emerging from the endosome or free in the cell.

FIG. 12. The map for antigen over expression vector pAF105. The denotation for each of the DNA segments is as follows: $P_{Rv3130}$ is the promoter sequence of antigen Rv3130c; $P_{Ag85B}$ is the promoter sequence of antigen Rv1886c. The genes in the expression cassette are Rv0288; Rv1886c and Rv3804c; aph is the aminoglycoside phosphotransferase gene (Gene bank accession number: X06402), which confers kanamycin resistance; OriE is the pUC origin of replication (Gene bank accession number: AY234331); leuD is the gene encoding 3-isopropylmalate dehydratase (i.e. Rv2987c); OriM is the origin of replication in *Mycobacterium* (Gene bank accession no: M23557).

FIG. 13A-F. AFRO-1 rBCG is more immunogenic than BCG in mice. Both C57Bl/6 mice (FIG. 13A-C) and BALB/c mice (FIG. 13D-F) were left unvaccinated (FIG. 13A, D) or were vaccinated subcutaneously with $5\times10^5$ CFU of either BCG 1331 (FIG. 13B, E) or the rBCG AFRO-1 (FIG. 13C, F). Eight weeks after vaccination, 3 mice/group were sacrificed, splenocytes were isolated, pooled and stimulated in vitro for 3 days with Ag85A, Ag85B, TB10.4, Ag85 complex or CFP. IFN-γ in culture supernatants was measured by ELISA. Bars are means ±S.D. from 3 replicate wells.

FIG. 14A-D. Vaccination with AFRO-1 rBCG protects mice as well as BCG. Eight weeks after vaccination of C57Bl/6 (FIG. 14A, B) or BALB/c mice (FIG. 14C, D) with 5×10⁵ CFU of either BCG 1331 or rBCG AFRO-1, the animals were aerogenically infected with ~100 CFU of the virulent *M. tuberculosis* Erdman KO1 strain. Mice were sacrificed and lungs (FIG. 14A, C) and spleens (FIG. 14B, D) were homogenized and plated onto 7H10 agar to determine bacterial loads. Bars represent mean ±SE from 12 mice/group. Numbers above the bars are percent reduction relative to unvaccinated control animals.

FIG. 15A-B. Mice vaccinated with AFRO-1 rBCG remain protected even when challenged 17 weeks later. BALB/c mice (20/group) were vaccinated subcutaneously with $5 \times 10^5$ CFU of either standard, lyophilized BCG 1331, BCG 1331 grown in liquid culture, AFV-102 rBCG or AFRO-1 rBCG. After 17 weeks, these mice were aerogenically infected with virulent *M. tuberculosis* and then sacrificed 13 weeks post infection. Lungs (FIG. 15A) and spleens (FIG. 15B) were homogenized and plated onto 7H10 agar to determine bacterial loads. Bars represent mean ±SE from 20 mice/group. Numbers above the bars are percent reduction relative to unvaccinated control animals.

Figure 16A:
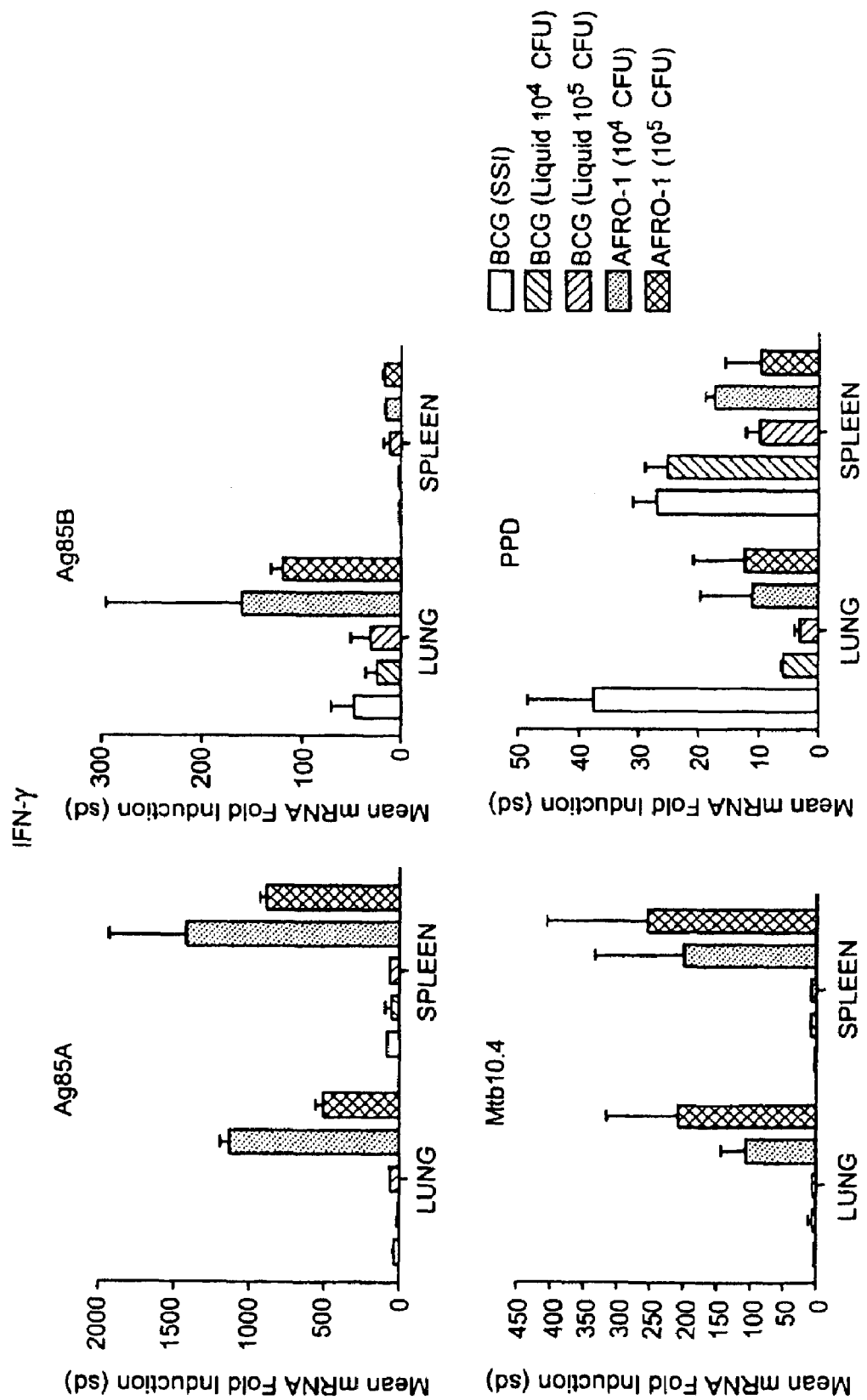
Figure 16B:
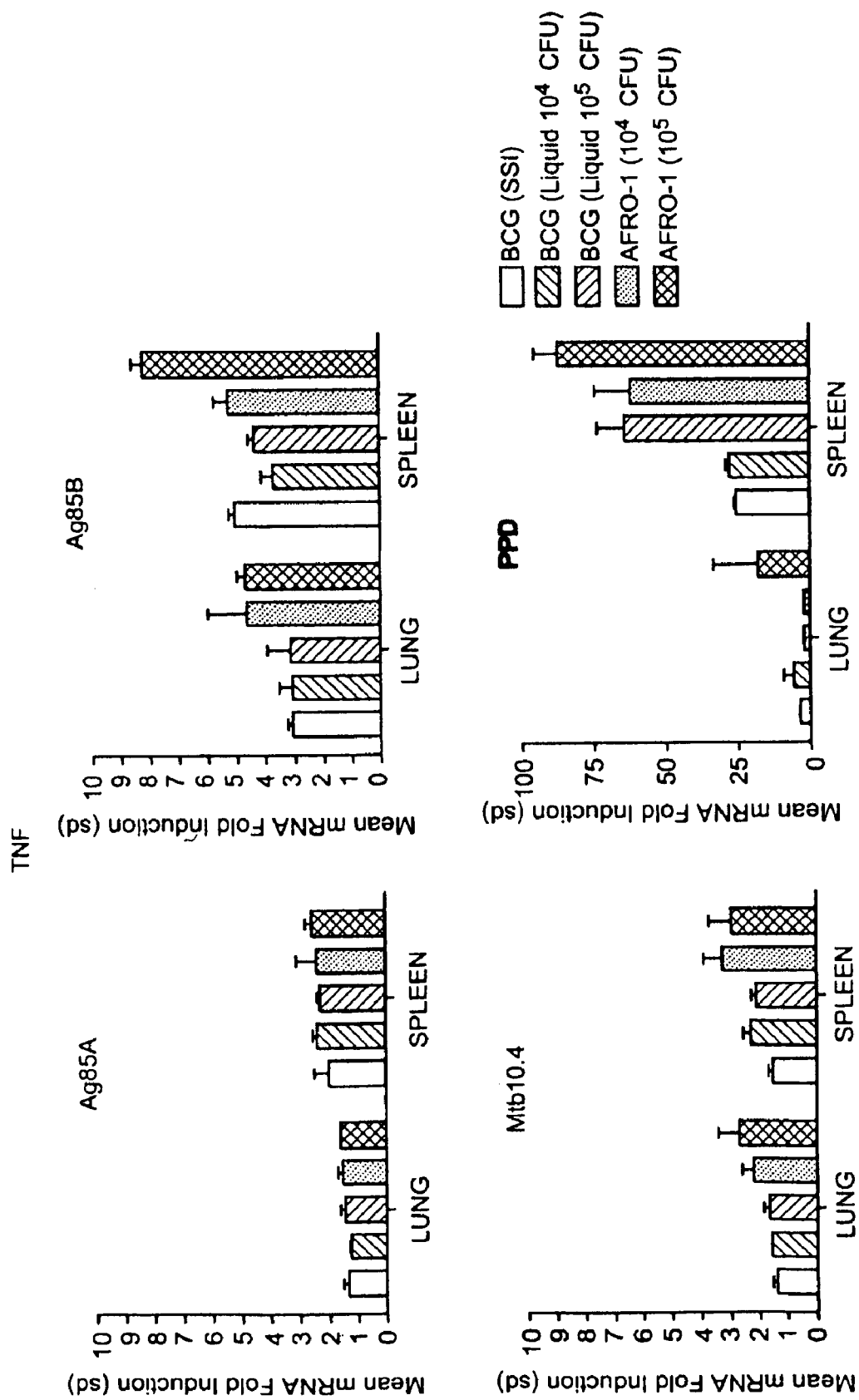
Figure 16C:
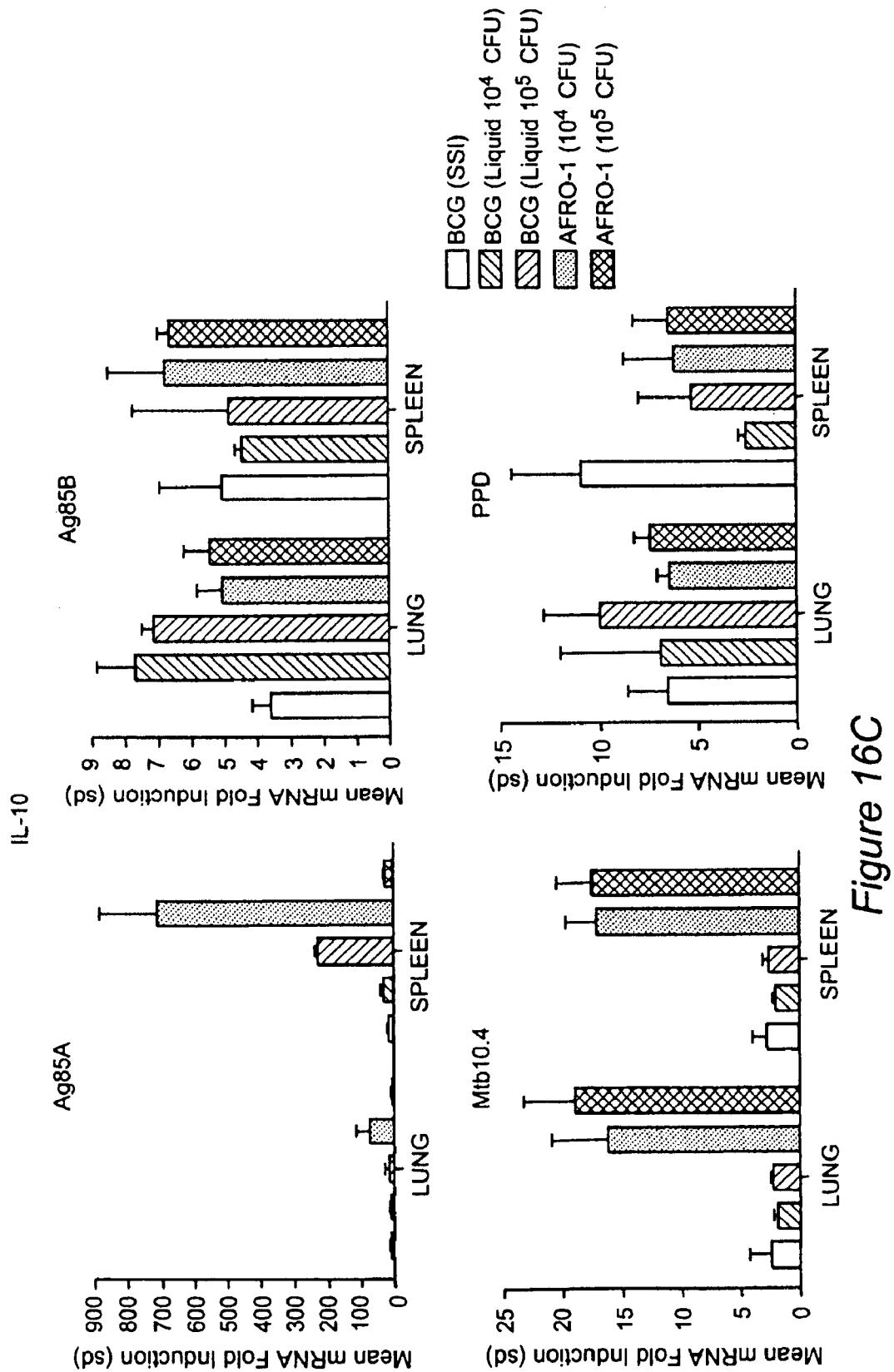

FIG. 16A-C. AFRO-1 rBCG is immunogenic in guinea pigs. Hartly guinea pigs (20 per group) were immunized intradermally with $1 \times 10^4$ CFU of standard, lyophilized BCG 1331 (black bars) or with $1 \times 10^4$ CFU or $1 \times 10^5$ CFU of either BCG 1331 grown in liquid culture or AFRO-1 rBCG. After 10 weeks, 3 animals/group were sacrificed and their lungs and spleens were removed. Single cell suspensions from these tissues were prepared and stimulated in vitro with Ag85A, Ag85B, TB10.4 and PPD for 24 hours. RNA was then purified from these cells, reverse-transcribed to cDNA and was subjected to real-time RT-PCR using primer specific for guinea pig IFN-γ (FIG. 16A), TNF (FIG. 16B) and IL-10 (FIG. 16C). The fold induction of each gene was calculated relative to the expression level of each gene in unstimulated cells. Bars are means ±S.D. from 3 animals. Note that expression levels vary dramatically for different cytokines and different stimuli and necessitate use of the different scales.

Figure 17A:
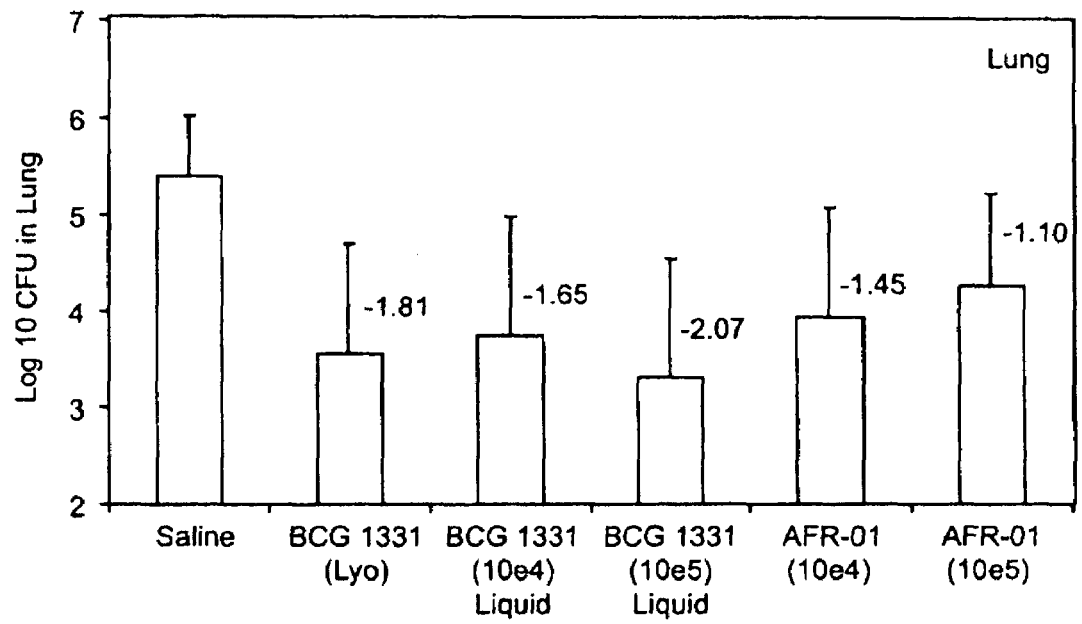
Figure 17B:
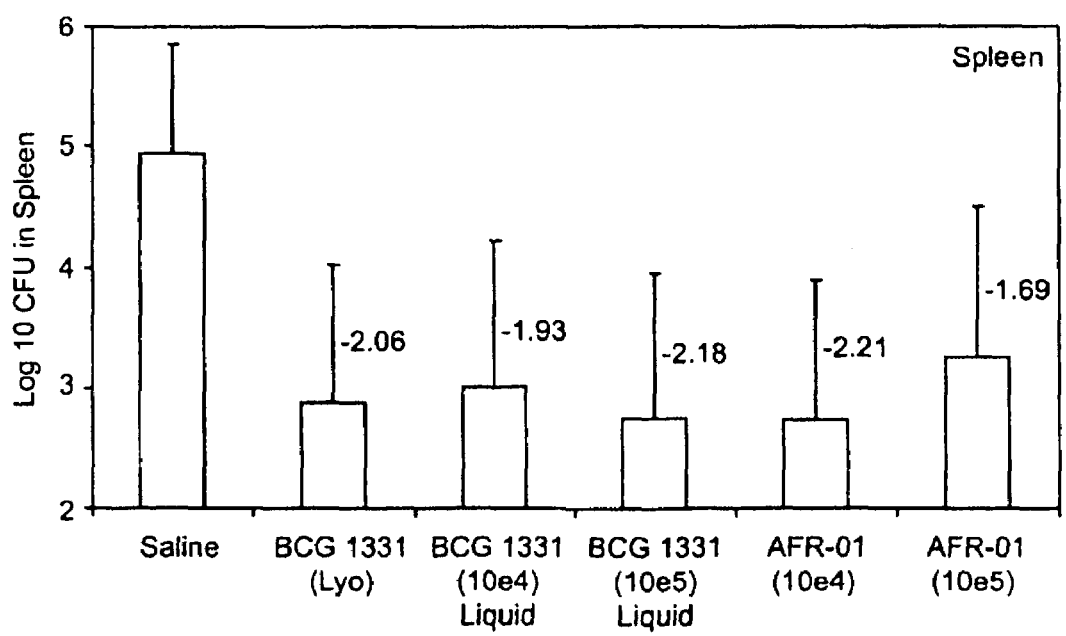

FIG. 17A-B. AFRO-1 rBCG protection in guinea pigs. Ten weeks after vaccination, the remaining 17 guinea pigs/group were challenged by aerosol with *M. tuberculosis* Erdman and 10 weeks post challenge, bacterial loads in the lung (A) and spleen (B) were determined by plating organ homogenates onto 7H10 agar. Bars represent the means ±S.D. of 17 guinea pigs.

Figure 18C:
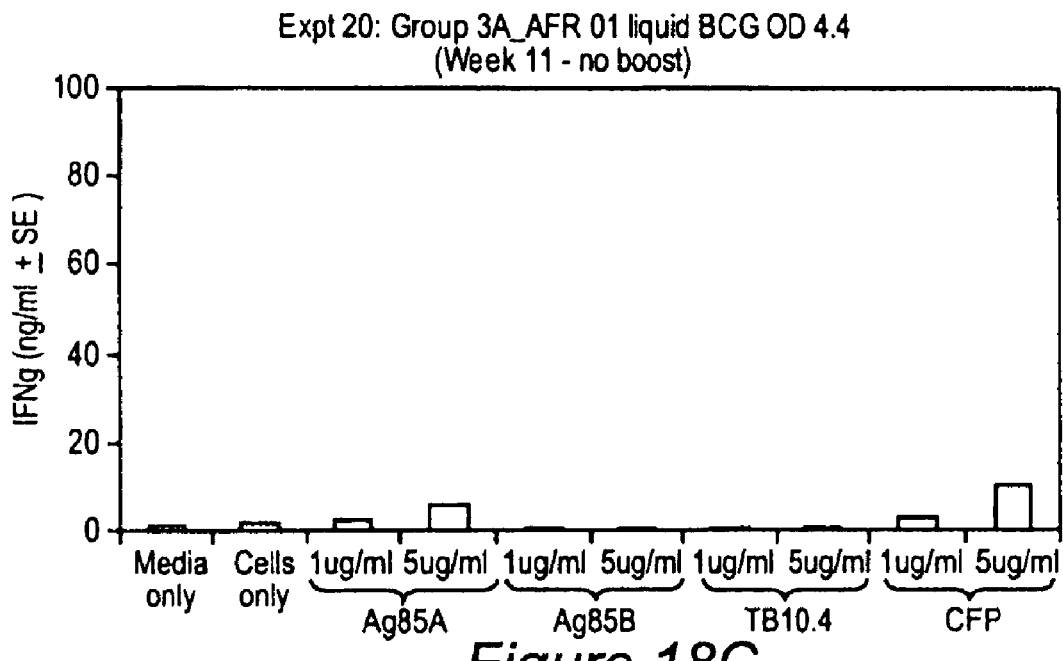
Figure 18D:
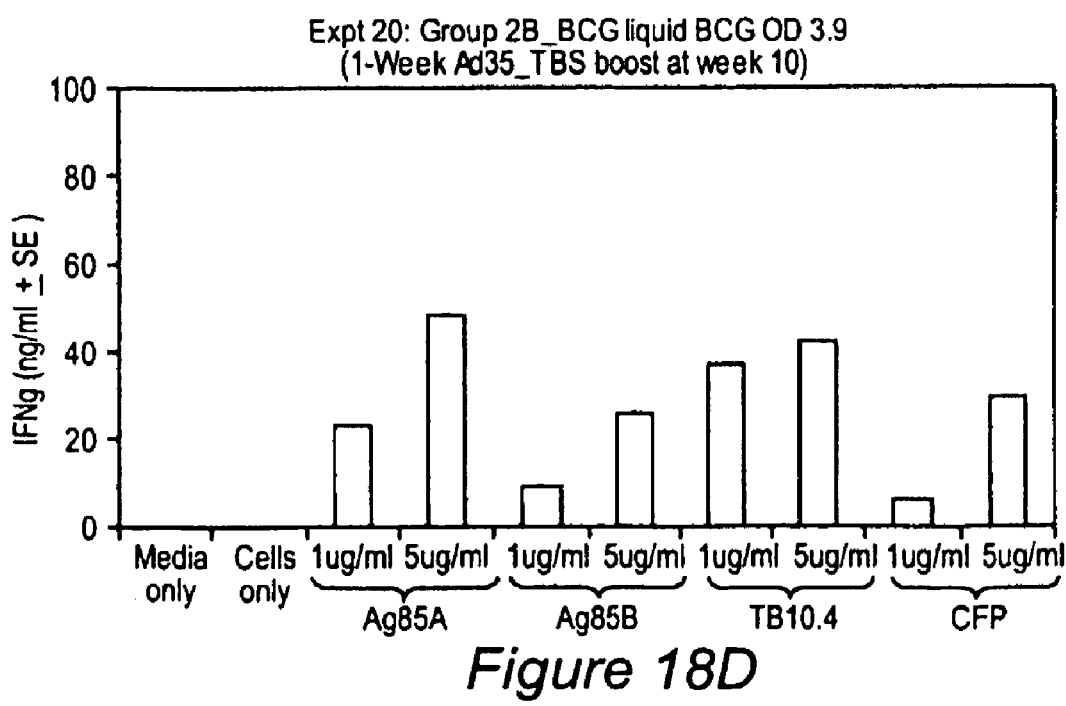
Figure 18E:
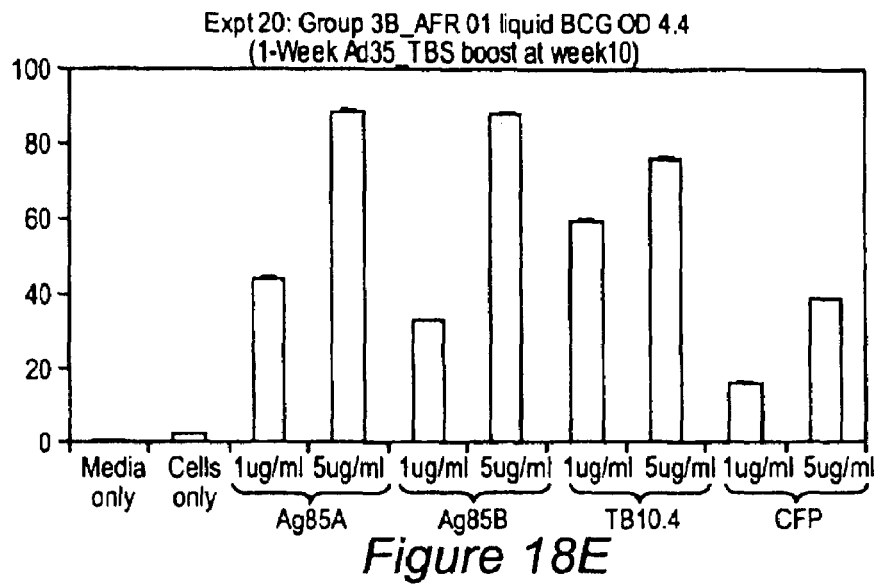

FIG. 18A-E. Enhanced immunogenicity in mice when AFRO-1 rBCG is boosted with Ad35-TBS. BALB/c mice were primed subcutaneously with $5 \times 10^5$ CFU BCG 1331 (FIG. 18 B,D) or AFRO-1 rBCG (FIG. 18C, E) and 10 weeks later some groups were boosted i.m. with $5 \times 10^9$ viral particles of Ad35-TBS (FIG. 18D, E). The unvaccinated control group did not receive any injection (FIG. 18A). Spleens were removed 1 week later from 6 mice/group, splenocytes from each group were pooled and stimulated in vitro with Ag85A, Ag85B, TB10.4 or CFP at 1 and 5 µg/ml for 3 days. IFN-γ was measured in the supernatants by ELISA. Bars are means ±S.D. from 3 replicate wells.

Figure 19A:
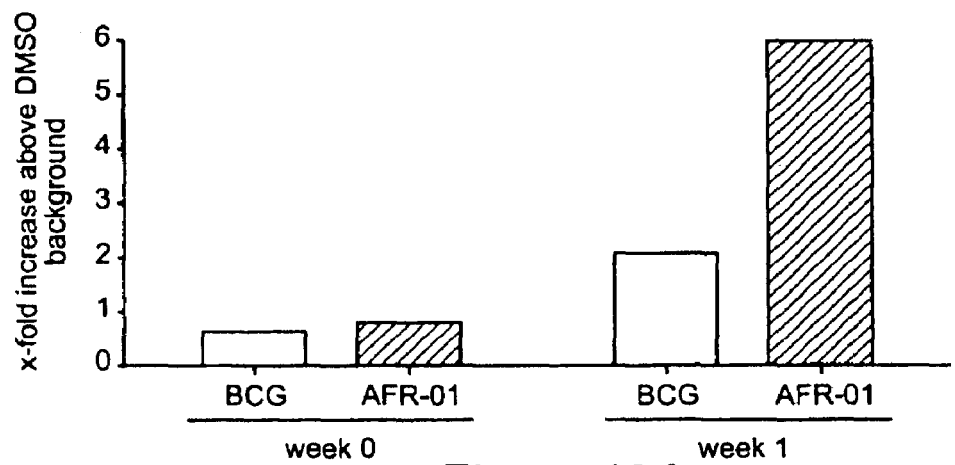
Figure 19B:
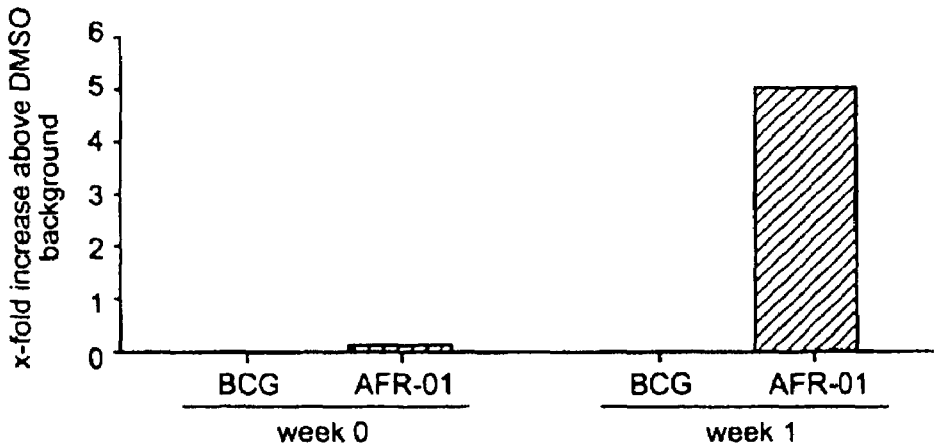

FIG. 19A-B. Priming with AFRO-1 generates more IFN-γ-positive CD8+ T cells than BCG after boosting with Ad35-TBS. BALB/c mice were primed subcutaneously with 5×10 CFU BCG-133 or AFRO-1 and $5 \times 10^9$ viral particles of Ad35-TBS was used to boost the animals 10 (FIG. 19A) or 17 weeks (FIG. 19B) later. Mice were sacrificed 1 week later and splenocytes were stimulated with overlapping mycobacterial peptides for 6 hours and subjected to intracellular staining. Briefly, cells were permeablized and reacted with fluorescently-labeled anti-IFN-γ, fixed and then labeled with anti-CD4 and anti-CD8. Cells were analyzed on a Partec flow cytometer and the percentage of IFN-γ-positive CD8+ T cells following stimulation was calculated relative to the percentage following incubation with DMSO alone. Bars represent mean ±S.D. from 6 mice.

Figure 20:
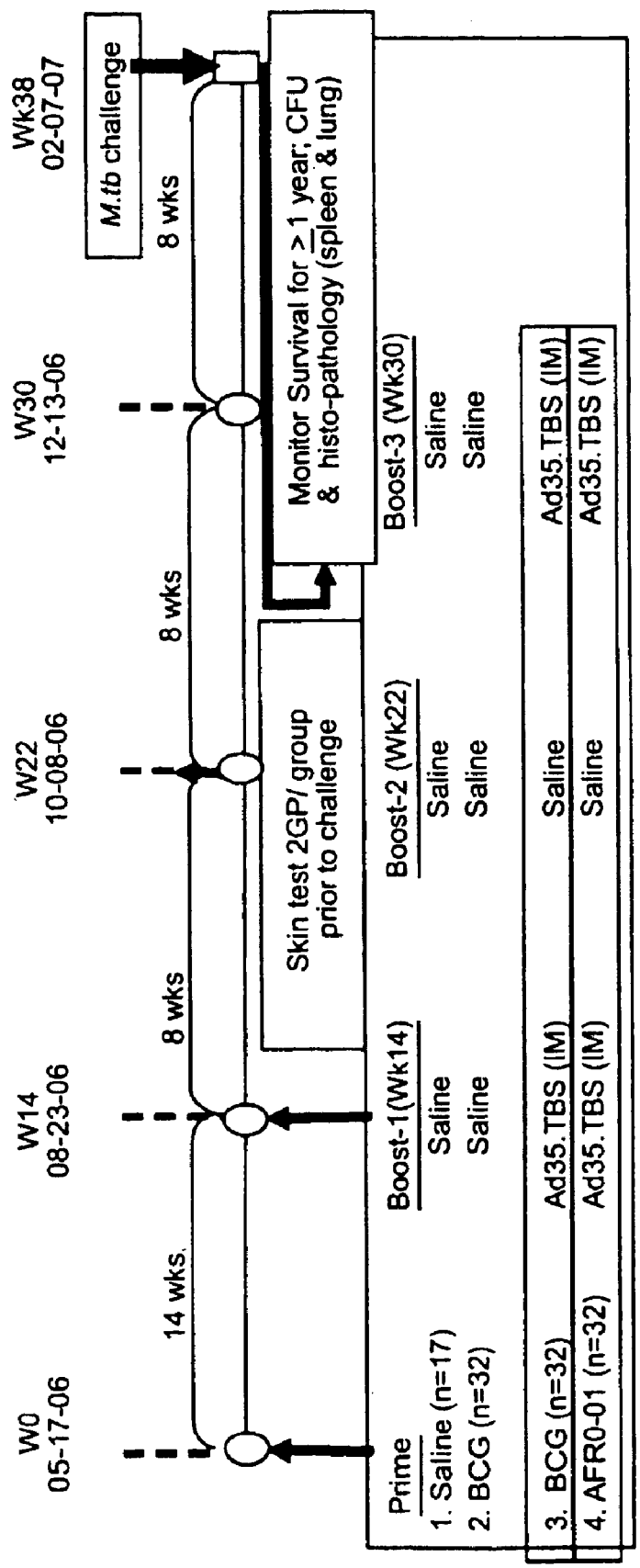

FIG. 20. Comparison of priming guinea pigs with BCG versus AFRO-1 rBCG when boosted with Ad35-TBS. Groups of 32 guinea pigs were primed intradermally with $1 \times 10^4$ CFU of either BCG (reference strain SSI-1331) or rBCG AFRO-1. One control group (#1) of 17 animals received only saline injections. Groups #3 and 4 were boosted i.m. with Ad35-TBS 14 weeks post priming and again 16 weeks later. All animals will be infected by aerosol with *M. tuberculosis* (K01 Erdman strain) 8 weeks after the last boost (38 weeks from the beginning of the study) and will be monitored for survival. Pulmonary histopathology and bacterial burdens will be determined post mortem.

Figure 21B:
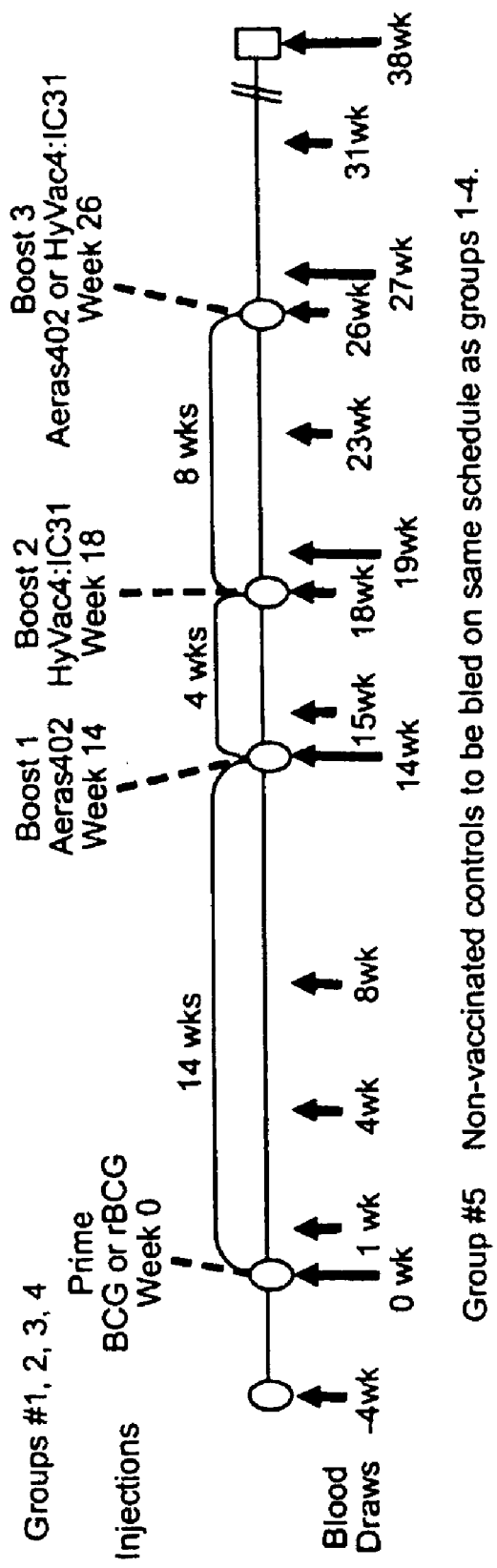

FIG. 21A-B. Immunogenicity of vaccine regimens in non-human primates. Rhesus macaques (33 total) were divided into 6 groups (FIG. 21A). Four groups were primed intradermally with $1 \times 10^4$ CFU of either BCG (reference strain SSI-1331, Groups 1, 3, 4) or AFRO-1 rBCG (Group 2). The naïve control group (#5) received only saline injections. Groups #1 and 2 were boosted i.m. with $3 \times 10^{10}$ vp Ad35-TBS 14 weeks later and then again 12 weeks later. Groups 3, 4 and 6 are components of a separate study. Blood was drawn from all monkeys at regular intervals as indicated by the red arrows (FIG. 21B) and was analyzed for immune responses to mycobacterial antigens.

Figure 22:
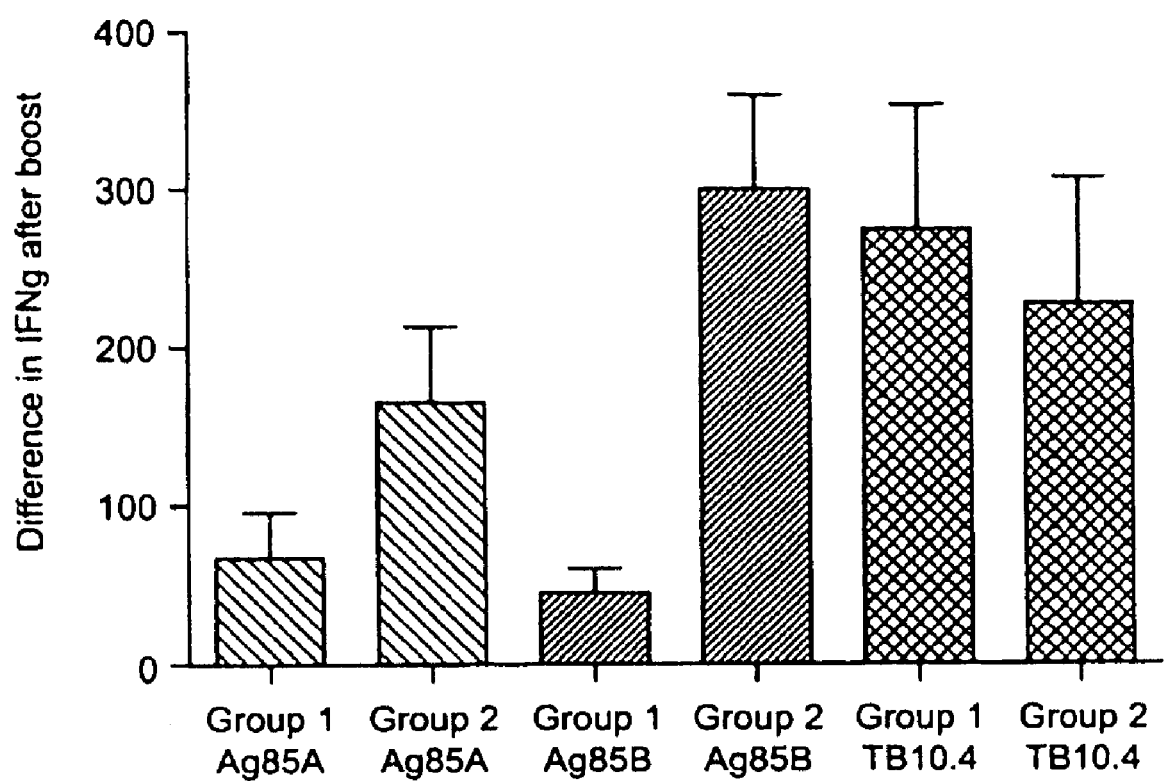

FIG. 22. Difference in antigen-specific IFN-γ proliferative responses before and after boosting with Ad35-TBS. Three day stimulation of cells with specific antigens and the resultant proliferative responses were compared before and after boosting with Ad35-TBS (AERAS-402) to demonstrate the enhanced priming of Class I immune responses in macaques vaccinated with BCG or endosome escape strain AFRO-1.

DETAILED DESCRIPTION OF THE PREFERRED EMBODIMENTS OF THE INVENTION

The present invention provides a rBCG that is capable of escaping from endosomes and accessing the host cell cytoplasm of cells that it infects. As a result, a superior CD8+ T-cell response to the rBCG is elicited in the cells.

The rBCG is genetically engineered to contain a functional endosomalysin that is expressed and secreted by the rBCG, and that mediates endosomal escape of the rBCG. The term endosomalysin herein refers to a protein that is capable of rupturing the endosomal membrane sufficiently to enable a bacterial cell to pass from the endosome into the cytosol. The term endosomolytic herein refers to a protein that has said rupturing activity. The term endosomalysis herein refers to the process of rupturing the endosomal membrane sufficiently to enable a bacterial cell to pass from the endosome into the cytosol. The endosomolytic protein is active in environments with pH values near neutrality, such as within the endosomes of cells infected with mycobacteria, and thus mediates escape of the bacteria into the cytoplasm.

In one embodiment of the present invention, the functional endosomolytic protein that is introduced into the rBCG strains of the present invention is PfoA from *Clostridium perfringens*, or a functional variant thereof. PfoA is a cytolysin secreted by *Clostridium perfringens* that is encoded by the pfoA gene (Genebank Accession #CPE0163). The gene and its protein sequence are shown in FIGS. 2 A and B, respectively. PfoA mediates bacterial escape from phagosomes, both in *Clostridium* and when expressed by *B. subtilis* (Portnoy et al., Infect Immun. July; 60(7): 2710-7; 1992).

Unlike Llo, PfoA is active at both pH 5.0 and pH 7.0 and thus remains active in the cytosol and causes damage to infected host cells (Portnoy et al., supra, 1992). Thus, when PfoA was expressed in *L. monocytogenes* in place of Llo, it enabled the strain to escape from phagosomes (Jones and Portnoy, Infect Immun. December; 62(12): 5608-13; 1994). However, its expression also caused damage to the host cells. Llo displays similar properties to PfoA, except that Llo is optimally active at pH 5.5 and displays little activity at pH 7.0. Thus, Llo mediates endosome escape once the pH of the endosome drops to pH 5.5 but does not affect the host cell because the pH of the cytosol, which is near neutrality, impedes Llo activity.

Portnoy et al. has further demonstrated that when PfoA is expressed in *L. monocytogenes* in a mutant form with a single amino acid change, the mutant form of PfoA is no longer toxic to the host cells, yet is still capable of mediating bacterial escape from a vacuole, and of carrying out intracellular growth (Portnoy et al., supra, 1992). The particular strain DP-12791, with a mutation that changes Gly137 to Gln137 in Pfo (i.e. $PfoA_{G137Q}$), is able to escape from the phagosome in a manner similar to wild type, but without producing a toxic effect on host cells. In addition, $PfoA_{G137Q}$ is active at both pH 5.6 and pH 7.4 with a reduced cytosolic half-life. The gene sequence of $PfoA_{G137Q}$ is shown in FIG. 3 (SEQ ID NO: 3).

The expression of PfoA allows escape from endosomes because the pore-forming activity of PfoA leads to eukaryotic cell membrane damage. PfoA forms pores in cholesterol-containing membranes by the spontaneous insertion of its domains into the bilayer. This happens via binding to cholesterol, which acts as a receptor. After binding, the toxin then forms a monomer-monomer interface (which is required for oligomer assembly), oligomerizes and partitions into the membrane by changing its structure, which is membrane binding-dependent. Formation of the membrane-bound oligomers leads to membrane damage and eventual lysis (Ramachandran et al., Nature Structure and Molecular Biology, 11(8), 697-705 (1995). $PfoA_{G137Q}$ is capable of mediating lysis of the vacuole in this manner. The preferable $PfoA_{G137Q}$ has limited activity in the cytoplasm of the infected host cell, because of its sensitivity to host proteases.

In one embodiment of the invention, the functional endosomolytic enzyme that is expressed by the rBCG is PfoA that is derived or isolated from *C. perfringens*. However, those of skill in the art will recognize that other endosomolytic proteins that are active at or near neutrality also exist that would be suitable for use in the present invention. Examples of such endosomolytic proteins include but are not limited to Pneumolysin (produced by *Streptococcus pneumoniae*), Streptolysin 0 (produced by *Streptococcus pyogenes*), Cerolysin (produced by *Bacilus cereus*), α-hemolysin (produced by *Staphylococcus aureus*), etc., and functional variants thereof.

By "functional endosomolytic protein" or "functional form" of a protein (or the gene product of a gene that is "functionally expressed"), we mean that the form of the protein that is produced by the rBCG bacterium exhibits the characteristic magnitude of activity for which the native or natural ("wild-type") protein is known in its native organism. The magnitude of activity of the functional form of the protein produced by the rBCG is, in general, at least about 50 percent of the usual activity of the wild-type protein when assayed under standard conditions as recognized by those of skill in the art. The magnitude of activity of the protein may be determined by measuring any physical observable, such binding to a ligand, or production of an effect, such as escape of rBCG from endosomes. Preferably, the activity magnitude is at least about 50%, 60%, 70%, 80%, 90%, 100%, or more of the standard magnitude of activity of the wild type protein when assayed under standard conditions as recognized by those of skill in the art.

By "functional variant" of a protein, we mean a polypeptide whose amino acid sequence is at least about 70% homologous to that of a wild type "reference" protein, and which retains the functional magnitude of activity (as described above) of the wild type protein. The amino acid sequence of the reference wild type protein is typically used as a starting point for mutations and alterations that are carried out by genetic engineering.

Preferably, a functional variant is a polypeptide with an amino acid sequence that displays about 75%, 80%, 85%, 90%, 95% or more identity to the reference amino acid sequence. Such functional variants include but are not limited to polypeptide sequences in which one or more conservative amino acid substitutions have been made. Conservative amino acid substitutions are well known to those of skill in the art, and include, for example, the substitution of one positively charged amino acid for another, one negatively charged amino acid for another, one hydrophobic amino acid for another, etc. Variant polypeptides may contain one or more of such substitutions, provided the resulting variant polypeptide retains the functional magnitude of activity as defined herein. "Functional variants" also encompass other changes to the primary sequence of the polypeptide of interest. Examples of changes include but are not limited to deletions and additions of amino acids, or the modification of amino acids (e.g. chemical modifications such as sulfonation, deamidation, phosphorylation, hydroxylation, etc.). Such changes may be the result of genetic engineering of a reference amino acid sequence, or may be the result of post-translational modifications of the protein, or both. Further, functional variants of an enzyme may be the result of natural mutations such as those that occur between analogous proteins with the same or similar activities that are isolated from different strains of a species, or from different species, or from different individual organisms within a species. Proteins from such naturally occurring variants may also serve as the reference protein, and the amino acid sequence of such a natural variant may serve as the reference sequence. In any case, all such functional variants of a reference protein retain the activity magnitude of the protein, as described herein.

Sequence homologies and identities as described herein are not intended to include heterologous amino acid sequences that are derived from sources other than the reference sequence and which are attached to or included in the polypeptide sequence of a protein for various other purposes. Examples of such heterologous sequences include but are not limited to sequences that facilitate polypeptide isolation (e.g. histidine tags), sequences that facilitate secretion or localization of the polypeptide within the cell, (e.g., various leader or targeting sequences), and sequences that code for glycosylation sites (glycosylation sequences), etc.

In any case, the functional variant will retain the activity magnitude of the protein of which it is a variant to the degree that the functional variant exhibits at least about 50 percent, and preferably about 60%, 70%, 80%, 90%, 100% or more, of the activity magnitude of the protein of which it is a variant, when assayed under standard conditions as recognized by those of skill in the art.

Further, the present invention also includes nucleic acid sequences encoding proteins and functional variants of proteins utilized in the present invention. The nucleic acid sequences may be deoxyribonucleotides, ribonucleotides, or modified forms of either, and may be single- or double-stranded. The nucleic acid sequences of the present invention include any that are listed herein, and are also intended to encompass variants thereof. For example, variants of the nucleic acids may not be identical to the listed sequences but may still encode an identical amino acid sequence due to the redundancy of the genetic code. Alternatively, some changes in the sequences of the present invention may be made (e.g. substitutions, deletions or additions) that result in changes in the encoded amino acid sequence, so long as the encoded amino acid sequence is a functional variant of the reference amino acid sequence as described above. Examples include but are not limited to: changes that cause conservative amino acid substitutions in the enzyme; and changes that result in non-conservative substitutions, or deletion or additions in the amino acid sequences. Such changes may be introduced for any reason, e.g. in order to alter post-translational modifications of the enzyme; to increase or decrease solubility; to prevent or introduce steric interactions in the translated polypeptide, etc. In general, variants of the nucleic acid sequences of the present invention will exhibit at least about 50 percent, and preferably about 60%, 70%, 80%, 90%, 95%, or 100% homology to the reference sequences, as determined by comparative procedures that are well known to those of skill in the art. Such variants are also characterized by exhibiting the ability to bind to the sequences utilized the present invention under conditions of high stringency. High stringency binding assays are well-known to those of skill it the art and can readily be applied to test potential variants of sequences of the present invention.

Sequence homologies as described herein are not intended to refer to nucleic acid sequences encoding heterologous amino acid sequences that are derived from sources other than the reference amino acid sequence, and which are attached to or included in the polypeptide sequence of a protein for various other purposes. For example, such nucleic acid sequences may encode heterologous amino acid sequences including but not limited to: sequences that facilitate polypeptide isolation (e.g. histidine tags), sequences that facilitate secretion or localization of the polypeptide within the cell, (e.g., various leader sequences or targeting sequences), and sequences that code for glycosylation sites (glycosylation sequences), etc.

Other variations of the nucleic acid sequences of the present invention that are intended to be encompassed by the present invention are sequences which have been altered for convenience or improvement in genetic engineering of the nucleic acid sequences, or in the expression of the amino acid sequences they encode. In general, such alterations will not affect the sequence of the polypeptide that is ultimately translated from the nucleic acid sequence; or the polypeptide will still fulfill the criteria set forth above for a functional variant. Examples of this type of alteration include but are not limited to: the inclusion of convenient restriction endonuclease sites in a nucleic acid sequence to facilitate manipulation of the sequence (e.g. for insertion of a sequence into a vector); the inclusion, deletion, or other change in a sequence or sequences involved in expression of the amino acid sequence (e.g. inclusion of any of various promoter and/or enhancer sequences, stop signals, super promoters, inducible promoters, and various other sequences that modify expression of the nucleic acid sequence); the inclusion of sequences that facilitate interaction of a vector with the nucleic acid of a host organism; etc.

Further, the nucleic acid sequences of the present invention may be chemically modified or include non-traditional bases for any of many reasons that are well-known to those of skill in the art, for example, to promote stability of the nucleic acid, or to confer a desired steric conformation.

By "active at neutral pH" and "active at a pH of about 7.0" we mean that the enzyme is active at a pH value in the range of from about 6.0 to about 8.0, and preferably in a range of about 6.5 to about 7.5.

The present invention provides recombinant *Mycobacteria*. In a preferred embodiment of the invention, the *Mycobacteria* are attenuated, as exemplified by BCG. However, those of skill in the art will recognize that other attenuated and non-attenuated *Mycobacteria* exist which would also be suitable for use in the present invention. Examples of additional types of *Mycobacteria* include but are not limited to *M. tuberculosis* strain CDC1551 (See, e.g. Griffith et al., *Am. J. Respir. Crit. Care Med. August;* 152(2): 808; 1995), *M. tuberculosis* strain Beijing (Soolingen et al., 1995), *M. tuberculosis* strain H37Ra (ATCC#: 25177), *M. tuberculosis* strain H37Rv (ATCC#: 25618), *M. bovis* (ATCC#: 19211 and 27291), *M. fortuitum* (ATCC#: 15073), *M. smegmatis* (ATCC#: 12051 and 12549), *M. intracellulare* (ATCC#: 35772 and 13209), *M. kansasii* (ATCC#: 21982 and 35775) *M. avium* (ATCC#: 19421 and 25291), *M. gallinarum* (ATCC#: 19711), *M. vaccae* (ATCC#: 15483 and 23024), *M. leprae* (ATCC#:), *M. marinarum* (ATCC#: 11566 and 11567), and *M. microtti* (ATCC#: 11152).

Examples of attenuated *Mycobacterium* strains include but are not restricted to *M. tuberculosis* pantothenate auxotroph strain (Sambandamurthy, *Nat. Med.* 2002 8(10): 1171; 2002), *M. tuberculosis* rpoV mutant strain (Collins et al., *Proc Natl Acad Sci USA.* 92(17): 8036; 1995), *M. tuberculosis* leucine auxotroph strain (Hondalus et al., Infect. Immun. 68(5): 2888; 2000), BCG Danish strain (ATCC #35733), BCG Japanese strain (ATCC #35737), BCG, Chicago strain (ATCC #27289), BCG Copenhagen strain (ATCC #: 27290), BCG Pasteur strain (ATCC #: 35734), BCG Glaxo strain (ATCC #: 35741), BCG Connaught strain (ATCC #35745), BCG Montreal (ATCC #35746).

In a further embodiment of this invention, attenuated *Mycobacterium* strains are modified to enhance apoptosis, wherein such strains induce strong cellular immune responses. Apoptosis is programmed cell death, which differs dramatically from necrotic cell death in terms of its induction and consequences. In fact, the process by which apoptosis of antigen containing cells results in the induction of potent cellular immunity has been called cross-priming (Heath et al., *Immunol Rev* 199; 2004; Gallucci et al., *Nature Biotechnology.* 5:1249; 1999; Albert et al., *Nature* 392:86; 1998). There are several mechanisms for induction of apoptosis which lead to increased antigen specific cell mediated immunity. Caspase 8-mediated apoptosis leads to antigen specific cellular immune protection (Sheridan et al., *Science* 277:818; 1997).

Another embodiment of the present invention, therefore, provides attenuated *Mycobacterium* strains which display enhanced pro-apoptosis properties, such as but not limited to secA1 secreted SodA lacking a leader peptide from the *Salmonella enteriditis* (Genbank accession no. 1068147), *Escherichia coli* (Genbank Accession No. 1250070) or *Shigella flexneri* (Genbank accession no. 1079977) or alternatively a SodA protein that is naturally non-secreted such as the SodA from *Listeria monocytogenes* EGD-e (Genbank Accession No. 986791). Such attenuated *Mycobacterium* strains do not produce extracellular Sod and thus do not suppress host immune responses, yet they do express intracellular Sod, thereby enabling survival of said *Mycobacterium* (Edwards et al., Am. J. Respir. Crit. Care Med. 164(12): 2213-9; 2001). Alternatively, attenuated *Mycobacterium* strains which display enhanced pro-apoptosis properties carry an inactivated Rv3238c gene.

Alternatively, expression of *Salmonella* SopE (Genbank accession #AAD54239, AAB51429 or AAC02071) or caspase-8 (Genbank accession #AAD24962 or AAH06737) in the cytoplasm of host cells by attenuated *Mycobacterium* in the present invention will impart a powerful method for inducing programmed cell death in the context of antigens expressed by said attenuated *Mycobacterium*, invoking high levels of antigen-specific cellular immunity.

Death receptor-5 (DR-5) also known as TRAIL-R2 (TRAIL receptor 2) or TNFR-SF-10B (Tumor Necrosis Factor-Superfamily member 10B) also mediates caspase 8 mediated apoptosis (Sheridan et al., 1997). Reovirus induced apoptosis is mediated by TRAIL-DR5 leading to subsequent clearance of the virus (Clarke et al., *J. Virol.* 74:8135; 2000). Expression of DR-5, such as human DR-5 (Genbank accession #BAA33723), herpesvirus-6 (HHV-6) DR-5 homologue (Genbank accession #CAA58423) etc., by attenuated *Mycobacterium* in the present invention provides a potent adjuvant effect for induction of antigen-specific cellular immunity against Mtb antigens.

In addition, host antigen presenting cells (such as macrophages and dendritic cells) can also be induced to undergo apoptosis through Fas ligation, which is a strong stimulus for induction of antigen specific cellular immune responses (Chattergoon et al., *Nat. Biotechnol.* 18:974; 2000). Thus, attenuated *Mycobacterium* expressing Fas or Fas cytoplasmic domain/CD4 ectodomain fusion protein will induce apoptosis and augmented antigen-specific cellular immune responses.

In summary, attenuated *Mycobacterium* strains which promote the induction of apoptosis provide a powerful tool for the induction of cellular responses that lead to immune mediated cell destruction of Mtb-infected cells, with subsequent elimination, reduction or prevention of the Mtb infection.

In yet another embodiment of the present invention, the two-component TB vaccine can include attenuated *Mycobacterium* strains that over express at least one *Mycobacterium* antigen, including but not restricted to Rv0125, Rv0203, Rv0287, Rv0288, Rv0603, Rv1196, Rv1223, Rv1271c, Rv1733c, Rv1738 Rv1804c, Rv1886, Rv2031c, Rv2032, Rv2253, Rv2290, Rv2389c, Rv2626c, Rv2627c, Rv2779c, Rv2873, Rv2875, Rv3017c, Rv3407, Rv3804c, Rv3810, or Rv3841. Alternatively, the over expressed *Mycobacterium* antigens can be in the form of a fusion protein comprised of one or more said *Mycobacterium* fusion proteins, such as Mtb72f (Brandt et al., *Infect. Immun.*, 72:6622-6632; 2004; Skeiky et al., *J. Immunol.*, 172:7618-7628; 2004), Hybrid-1 (Olsen et al., *Infect, Immun.*, 72:6148-6150; 2004; Langermans et al., *Vaccine*, 23:2740-2750; 2005), Hyvac-4 (Dietrich et al., *J. Immunol.*, 174:6332-6339; 2005), etc.

This invention has utility in the development of vaccines against pathogenic *Mycobacterium* species and in the development of antigen delivery vaccine vectors. A *Mycobacterium* vector is defined herein as any *Mycobacterium* strain engineered to express at least one passenger nucleotide sequence (herein referred to as "PNS") comprised of DNA or RNA and encoding any combination of antigens, immunoregulatory factors or adjuvants, as set forth below. The PNS can be introduced into the chromosome or as part of an expression vector using compositions and methods well known in the art (Jacobs et al., *Nature* 327:532-535; 1987; Barletta et al., Res Microbiol. 141:931-939; 1990; Kawahara et al., *Clin Immunol.* 105:326-331; 2002; Lim et al., *AIDS Res Hum Retroviruses.* 13:1573-1581; 1997; Chujoh et al., *Vaccine*, 20:797-804; 2001; Matsumoto et al., *Vaccine*, 14:54-60; 1996; Haeseleer et al., *Mol Biochem Parasitol.*, 57:117-126; 1993).

In the present invention, the *Mycobacterium* vector may carry a PNS encoding an immunogen, which may be either a foreign immunogen from viral, bacterial and parasitic pathogens, or an endogenous immunogen, such as but not limited to an autoimmune antigen or a tumor antigen. The immunogens may be the full-length native protein, chimeric fusions between the foreign immunogen and an endogenous protein or mimetic, a fragment or fragments thereof of an immunogen that originates from viral, bacterial and parasitic pathogens.

As used herein, "foreign immunogen" means a protein or fragment thereof, which is not normally expressed in the recipient animal cell or tissue, such as, but not limited to, viral proteins, bacterial proteins, parasite proteins, cytokines, chemokines, immunoregulatory agents, or therapeutic agents.

An "endogenous immunogen" means a protein or part thereof that is naturally present in the recipient animal cell or tissue, such as, but not limited to, an endogenous cellular protein, an immunoregulatory agent, or a therapeutic agent. Alternatively or additionally, the immunogen may be encoded by a synthetic gene and may be constructed using conventional recombinant DNA methods known to those of skill in the art.

The foreign immunogen can be any molecule that is expressed by any viral, bacterial, or parasitic pathogen prior to or during entry into, colonization of, or replication in their animal host; the *Mycobacterium* vector may express immunogens or parts thereof that originate from viral, bacterial and parasitic pathogens. These pathogens can be infectious in humans, domestic animals or wild animal hosts.

The viral pathogens, from which the viral antigens are derived, include, but are not limited to, Orthomyxoviruses, such as influenza virus (Taxonomy ID: 59771; Retroviruses, such as RSV, HTLV-1 (Taxonomy ID: 39015), and HTLV-II (Taxonomy ID: 11909), Herpes viruses such as EBV Taxonomy ID: 10295); CMV (Taxonomy ID: 10358) or herpes simplex virus (ATCC #: VR-1487); Lentiviruses, such as HIV-1 (Taxonomy ID: 12721) and HIV-2 Taxonomy ID: 11709); Rhabdoviruses, such as rabies; Picomoviruses, such as Poliovirus (Taxonomy ID: 12080); Poxviruses, such as vaccinia (Taxonomy ID: 10245); Rotavirus (Taxonomy ID: 10912); and Parvoviruses, such as adeno-associated virus 1 (Taxonomy ID: 85106).

Examples of viral antigens can be found in the group including but not limited to the human immunodeficiency virus antigens Nef (National Institute of Allergy and Infectious Disease HIV Repository Cat. #183; Genbank accession #AF238278), Gag, Env (National Institute of Allergy and Infectious Disease HIV Repository Cat. #2433; Genbank accession #U39362), Tat (National Institute of Allergy and Infectious Disease HIV Repository Cat. #827; Genbank accession #M13137), mutant derivatives of Tat, such as Tat-Δ3145 (Agwale et al., *Proc. Natl. Acad. Sci. In press.* Jul. 8, 2002), Rev (National Institute of Allergy and Infectious Disease HIV Repository Cat. #2088; Genbank accession #L14572), and Pol (National Institute of Allergy and Infectious Disease HIV Repository Cat. #238; Genbank accession #AJ237568) and T and B cell epitopes of gp120 (Hanke and McMichael, AIDS Immunol Lett., 66:177; 1999); (Hanke, et al., *Vaccine*, 17:589; 1999); (Palker et al., *J. Immunol.*, 142: 3612-3619; 1989) chimeric derivatives of HIV-1 Env and gp120, such as but not restricted to fusion between gp120 and CD4 (Fouts et al., *J. Virol.*, 74:11427-11436; 2000); truncated or modified derivatives of HIV-1 env, such as but not restricted to gp140 (Stamatos et al., *J Virol,* 72:9656-9667; 1998) or derivatives of HIV-1 Env and/or gp140 thereof (Binley, et al., *J Virol,* 76:2606-2616; 2002); (Sanders, et al., *J*

Virol, 74:5091-5100; 2000); (Binley, et al., *J Virol*, 74:627-643; 2000), the hepatitis B surface antigen (Genbank accession #AF043578); (Wu et al., *Proc. Natl. Acad. Sci., USA*, 86:4726-4730; 1989); rotavirus antigens, such as VP4 (Genbank accession #AJ293721; Mackow et al., *Proc. Natl. Acad. Sci., USA*, 87:518-522; 1990) and VP7 (Genbank accession #AY003871) (Green et al., *J. Virol.*, 62:1819-1823; 1988), influenza virus antigens such as hemagglutinin or (Genbank accession #AJ404627); (Pertmer and Robinson, *Virology*, 257:406; 1999); nucleoprotein (Genbank accession #AJ289872); (Lin et al., *Proc. Natl. Acad. Sci.*, 97: 9654-9658; 2000) herpes simplex virus antigens such as thymidine kinase (Genbank accession #AB047378); (Whitley et al., *New Generation Vaccines*, 825-854; 2004).

The bacterial pathogens, from which the bacterial antigens are derived, include but are not limited to, *Mycobacterium* spp., *Helicobacter pylori*, *Salmonella* spp., *Shigella* spp., *E. coli*, *Rickettsia* spp., *Listeria* spp., *Legionella pneumoniae*, *Pseudomonas* spp., *Vibrio* spp., and *Borellia burgdorferi*.

Examples of protective antigens of bacterial pathogens include the somatic antigens of enterotoxigenic *E. coli*, such as the CFA/I fimbrial antigen (Yamamoto et al., *Infect. Immun.*, 50:925-928; 1985) and the nontoxic B-subunit of the heat-labile toxin (Klipstein et al., *Infect. Immun.*, 40:888-893; 1983); pertactin of *Bordetella pertussis* (Roberts et al., Vacc., 10:43-48; 1992), adenylate cyclase-hemolysin of *B. pertussis* (Guiso et al., *Micro. Path.*, 11:423-431; 1991), fragment C of tetanus toxin of *Clostridium tetani* (Fairweather et al., *Infect. Immun.*, 58:1323-1326; 1990), OspA of *Borellia burgdorferi* (Sikand, et al., *Pediatrics*, 108:123-128; 2001); (Wallich, et al., *Infect Immun*, 69:2130-2136; 2001), protective paracrystalline-surface-layer proteins of *Rickettsia prowazekii* and *Rickettsia typhi* (Carl, et al., *Proc Natl Acad Sci USA*, 87:8237-8241; 1990), the listeriolysin (also known as "Llo" and "Hly") and/or the superoxide dismutase (also know as "SOD" and "p60") of *Listeria monocytogenes* (Hess, et al., *Infect. Immun.* 65:1286-92; 1997; (Hess, et al., *Proc. Natl. Acad. Sci.* 93:1458-1463; 1996); (Bouwer, et al., *J. Exp. Med.* 175:1467-71; 1992), the urease of *Helicobacter pylori* (Gomez-Duarte, et al., *Vaccine* 16, 460-71; 1998); Corthesy-Theulaz, et al., *Infection & Immunity* 66, 581-6; 1998), and the receptor-binding domain of lethal toxin and/or the protective antigen of *Bacillus anthrax* (Price, et al., *Infect. Immun.* 69, 4509-4515; 2001).

The parasitic pathogens, from which the parasitic antigens are derived, include but are not limited to, *Plasmodium* spp., such as *Plasmodium falciparum* (ATCC#: 30145); *Trypanosome* spp., such as *Trypanosoma cruzi* (ATCC#: 50797); *Giardia* spp., such as *Giardia intestinalis* (ATCC#: 30888D); *Boophilus* spp., *Babesia* spp., such as *Babesia microti* (ATCC#: 30221); *Entamoeba* spp., such as *Entamoeba histolytica* (ATCC#: 30015); *Eimeria* spp., such as *Eimeria maxima* (ATCC#40357); *Leishmania* spp. (Taxonomy ID: 38568); *Schistosome* spp., *Brugia* spp., *Fascida* spp., *Dirofilaria* spp., *Wuchereria* spp., and *Onchocerea* spp.

Examples of protective antigens of parasitic pathogens include the circumsporozoite antigens of *Plasmodium* spp. (Sadoff et al., *Science* 240:336-337; 1988), such as the circumsporozoite antigen of *P. bergerii* or the circumsporozoite antigen of *P. falciparum*; the merozoite surface antigen of *Plasmodium* spp. (Spetzler et al., *Int. J. Pept. Prot. Res.*, 43:351-358; 1994); the galactose specific lectin of *Entamoeba histolytica* (Mann et al., Proc. Natl. Acad. Sci., USA, 88:3248-3252; 1991), gp63 of *Leishmania* spp. (Russell et al., J. Immunol., 140:1274-1278; 1988); (Xu and Liew, Immunol., 84: 173-176; 1995), gp46 of *Leishmania major* (Handman et al., *Vaccine*, 18: 3011-3017; 2000), paramyosin of *Brugia malayi* (Li et al., *Mol. Biochem. Parasitol.*, 49:315-323; 1991), the triose-phosphate isomerase of *Schistosoma mansoni* (Shoemaker et al., *Proc. Natl. Acad. Sci.*, USA, 89:1842-1846; 1992); the secreted globin-like protein of *Trichostrongylus colubriformis* (Frenkel et al., *Mol. Biochem. Parasitol.*, 50:27-36; 1992); the glutathione-S-transferase's of *Frasciola hepatica* (Hillyer et al., *Exp. Parasitol.*, 75:176-186; 1992), *Schistosoma bovis* and *S. japonicum* (Bashir et al., *Trop. Geog. Med.*, 46:255-258; 1994); and KLH of *Schistosoma bovis* and *S. japonicum* (Bashir et al., supra, 1994).

As mentioned earlier, the *Mycobacterium* vector may carry a PNS encoding an endogenous immunogen, which may be any cellular protein, immunoregulatory agent, or therapeutic agent, or parts thereof, that may be expressed in the recipient cell, including but not limited to tumor, transplantation, and autoimmune immunogens, or fragments and derivatives of tumor, transplantation, and autoimmune immunogens thereof. Thus, in the present invention, *Mycobacterium* vector may carry a PNS encoding tumor, transplant, or autoimmune immunogens, or parts or derivatives thereof. Alternatively, the *Mycobacterium* vector may carry synthetic PNS's (as described above), which encode tumor-specific, transplant, or autoimmune antigens or parts thereof.

Examples of tumor specific antigens include prostate specific antigen (Gattuso et al., *Human Pathol.*, 26:123-126; 1995), TAG-72 and CEA (Guadagni et al., *Int. J. Biol. Markers*, 9:53-60; 1994), MAGE-1 and tyrosinase (Coulie et al., *J. Immunothera.*, 14:104-109; 1993). Recently, it has been shown in mice that immunization with non-malignant cells expressing a tumor antigen provides a vaccine effect, and also helps the animal mount an immune response to clear malignant tumor cells displaying the same antigen (Koeppen et al., *Anal. N.Y. Acad. Sci.*, 690:244-255; 1993).

Examples of transplant antigens include the CD3 molecule on T cells (Alegre et al., *Digest. Dis. Sci.*, 40:58-64; 1995). Treatment with an antibody to CD3 receptor has been shown to rapidly clear circulating T cells and reverse cell-mediated transplant rejection (Alegre et al, supra, 1995).

Examples of autoimmune antigens include IAS β chain (Topham et al., *Proc. Natl. Acad. Sci.*, USA, 91:8005-8009; 1994). Vaccination of mice with an 18 amino acid peptide from IAS β chain has been demonstrated to provide protection and treatment to mice with experimental autoimmune encephalomyelitis (Topham et al., supra, 1994).

*Mycobacterium* Vectors which Express an Adjuvant

It is feasible to construct *Mycobacterium* vectors that carry PNS encoding an immunogen and an adjuvant, and are useful in eliciting augmented host responses to the vector and PNS-encoded immunogen. Alternatively, it is feasible to construct *Mycobacterium* vectors that carry PNS encoding an adjuvant, which are administered in mixtures with other *Mycobacterium* vectors that carry PNS encoding at least one immunogen to increase host responses to said immunogen encoded by the partner *Mycobacterium* vector.

The particular adjuvant encoded by PNS inserted in said *Mycobacterium* vector is not critical to the present invention and may be the A subunit of cholera toxin (i.e. CtxA; Genbank accession no. X00171, AF175708, D30053, D30052), or parts and/or mutant derivatives thereof (E.g. the A1 domain of the A subunit of Ctx (i.e. CtxA1; Genbank accession no. K02679)), from any classical *Vibrio cholerae* (E.g. *V. cholerae* strain 395, ATCC #39541) or El Tor *V. cholerae* (E.g. *V. cholerae* strain 2125, ATCC #39050) strain. Alternatively, any bacterial toxin that is a member of the family of bacterial adenosine diphosphate-ribosylating exotoxins (Krueger and Barbier, Clin. Microbiol. Rev., 8:34; 1995), may be used in place of CtxA, for example the A subunit of heat-labile toxin (referred to herein as EltA) of enterotoxigenic *Escherichia coli* (Genbank accession #M35581), pertussis toxin S1 sub-unit (E.g. ptxS1, Genbank accession #AJ007364, AJ007363, AJ006159, AJ006157, etc.); as a further alternative the adjuvant may be one of the adenylate cyclase-hemolysins of *Bordetella pertussis* (ATCC #8467), *Bordetella bronchiseptica* (ATCC #7773) or *Bordetella parapertussis* (ATCC #15237), E.g. the cyaA genes of *B. pertussis* (Genbank accession no. X14199), *B. parapertussis* (Genbank accession no. AJ249835) or *B. bronchiseptica* (Genbank accession no. Z37112).

*Mycobacterium* vector which express an immunoregulatory agent

Yet another approach entails the use of *Mycobacterium* vector that carry at least one PNS encoding an immunogen and a cytokine, which are used to elicit augmented host responses to the PNS-encoded immunogen *Mycobacterium* vector. Alternatively, it is possible to construct a *Mycobacterium* vector that carries a PNS encoding said cytokine alone, which are used in admixtures with at least one other *Mycobacterium* vector carrying a PNS encoding an immunogen to increase host responses to PNS-encoded immunogens expressed by the partner *Mycobacterium* vector.

The particular cytokine encoded by the *Mycobacterium* vector is not critical to the present invention includes, but not limited to, interleukin-4 (herein referred to as "IL-4"; Genbank accession no. AF352783 (Murine IL-4) or NM_000589 (Human IL-4)), IL-5 (Genbank accession no. NM_010558 (Murine IL-5) or NM_000879 (Human IL-5)), IL-6 (Genbank accession no. M20572 (Murine IL-6) or M29150 (Human IL-6)), IL-10 (Genbank accession no. NM_010548 (Murine IL-10) or AF418271 (Human IL-10)), $1'-12_{p40}$ (Genbank accession no. NM_008352 (Murine IL-12 p40) or AY008847 (Human IL-12 p40)), $IL-12_{p70}$ (Genbank accession no. NM_008351/NM_008352 (Murine IL-12 p35/40) or AF093065/AY008847 (Human IL-12 p35/40)), TGFβ (Genbank accession no. NM_011577 (Murine TGFβ1) or M60316 (Human TGFβ1)), and TNFα Genbank accession no. X02611 (Murine TNFα) or M26331 (Human TNFα)).

The specific method used to introduce a gene encoding a Pfo gene into the genome of BCG is not a critical feature of the invention and may be selected from methods well known to those skilled in the art (Parish et al., *Microbiology*, 145: 3497-3503; 1999). A preferred method entails targeting the Pfo gene to the ureC locus, thereby resulting in inactivation of the latter gene and creating a marker for selection of modified strains (Qadri et al., *J Clinic Micro.* 20(6), 1198-1199; 1984). To accomplish the same, a synthetic allelic exchange plasmid, such as the plasmid described in the Examples section below, can be modified to harbor 1 kb sequences that flank the 5-prime and 3-prime ends of the ureC gene (Genome Database #Mb1881). The PfoA gene (Genome Database #CPE0163) is then inserted in between the flanking sequences under control of Ag85B promoter. To secrete the PfoA protein, an Ag85B leader peptide sequence is used in place of the native PfoA signal sequence to ensure efficient secretion from recombinant BCG strains.

The method by which allelic exchange plasmids are introduced into target BCG strains is not a crucial feature of the present invention and can be accomplished by standard electroporation protocols for *Mycobacterium*. Similarly, the specific method to affect allelic exchange and introduce the Pfo allele into the ureC locus is not a crucial feature of the invention and can be selected from methods well known to those skilled in the art. A suicide vector such as that depicted in FIG. 1 provides a preferred method, as this plasmid contains two antibiotic selection markers, thus minimizing the selection of spontaneous antibiotic-resistant mutants. During allele exchange, the PfoA gene segment replaces the ureC gene as a result of homologous recombination of left and right flanking sequences, thereby resulting in stable chromosomal integration and expression of PfoA. An advantage of this approach is that no antibiotics are required to maintain the final product, and no antibiotic resistant genotype or phenotype is present in the final strain. This is the preferred embodiment for products for human use (they are "antibiotic free"). A UreC-negative phenotype will mark strains that have undergone the allelic exchange and replaced ureC with Pfo, it being understood that the UreC positive phenotype might also be employed in certain applications.

In the present invention, the location of the pfoA in the BCG is not restricted to ureC. Other locations include but are not limited to pfoA integrated into a plasmid, and the attB site on the chromosome. Those skilled in the art will know other locations of the chromosome that are potential sites for pfoA integration and expression.

The present invention also provides vaccine preparations for use in eliciting an immune response against tuberculosis. The vaccine preparations include at least one rBCG strain as described herein, and a pharmacologically suitable carrier. The preparation of such compositions for use as vaccines is well known to those of skill in the art. Typically, such compositions are prepared either as liquid solutions or suspensions, however, solid forms such as tablets, pills, powders and the like are also contemplated. Solid forms suitable for solution in, or suspension in, liquids prior to administration may also be prepared. The preparation may also be emulsified. The active ingredients may be mixed with excipients that are pharmaceutically acceptable and compatible with the active ingredients. Suitable excipients are, for example, water, saline, dextrose, raffinose, glycerol, ethanol and the like, or combinations thereof. In addition, the composition may contain minor amounts of auxiliary substances such as wetting or emulsifying agents, pH buffering agents, and the like. In addition, the composition may contain other adjuvants.

If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of rBCG bacteria in the formulations may vary. However, in general, the amount in the formulations will be from about 1-99 percent. The vaccine preparations of the present invention may further comprise an adjuvant, suitable examples of which include but are not limited to Seppic, Quil A, Alhydrogel, etc. Further, the vaccine preparations of the present invention may contain a single type of rBCG. Alternatively, more than one type of rBCG may be utilized in a vaccine.

The present invention also provides methods of eliciting an immune response to tuberculosis and methods of vaccinating a mammal against tuberculosis. By eliciting an immune response, we mean that administration of the vaccine preparation of the present invention causes the synthesis of specific antibodies (at a titer in the range of 1 to $1 \times 10^6$, preferably $1 \times 10^3$, more preferable in the range of about $1 \times 10^3$ to about $1 \times 10^6$, and most preferably greater than $1 \times 10^6$) and/or cellular proliferation, as measured, e.g. by $^3$H thymidine incorporation. The methods involve administering a composition comprising a rBCG strain of the present invention in a pharmacologically acceptable carrier to a mammal. The vaccine preparations of the present invention may be administered by any of the many suitable means which are well known to those of skill in the art, including but not limited to by injection, orally, intranasally, by ingestion of a food product containing the rBCG, etc. In preferred embodiments, the mode of administration is subcutaneous or intramuscular.

The following examples are to be considered as exemplary of various aspects of the present invention and are not intended to be limiting with respect to the practice of the invention. Those of ordinary skill in the art will appreciate that alternative materials, conditions, and procedures may be varied and remain within the skill of the ordinarily skilled artisan without departing from the general scope of the invention as taught in the specification.

EXAMPLES

The pivotal role of MHC class I-restricted CD8+ T cells in TB immune protection has been demonstrated (Flynn et al., supra, 1992). In an effort to improve the CD8+ T cell response, a recombinant BCG strain has been engineered to express listeriolysin of *Listeria monocytogenes*. However, this recombinant BCG (rBCG) failed to display an increased capacity for endosomal escape, and therefore does not cause increased induction of, for example, MHC class I-restricted CD8+ cytotoxic T cell responses. When examined, the strain displays less than 1% escape from the endosome. This is not surprising because listeriolysin's activity is highly pH sensitive, thus the enzyme is likely not active at the pH within the endosome. Despite this drawback, the protection and safety of this recombinant strain were both dramatically improved. Based on this observation, we have constructed a new rBCG strain by introducing $PfoA_{G137Q}$, derived from *Clostridium perfringens* into the chromosome of BCG. $PfoA_{G137Q}$ has one amino acid change at position 137 from G to Q. This single amino acid change results in loss of toxicity of wild-type PfoA in mammalian cells, yet the enzyme retains its endosomolytic function. The resultant strain has been shown to be safe and immunogenic in a mouse model.

Materials and Methods: General

For each experiment described in the following sections, restriction endonucleases (herein "REs"); New England Biolabs Beverly, Mass.), T4 DNA ligase (New England Biolabs, Beverly, Mass.) and Taq polymerase (Life Technologies, Gaithersburg, Md.) were used according to the manufacturers' protocols; Plasmid DNA was prepared using small-scale (Qiagen Miniprep$^R$ kit, Santa Clarita, Calif.) or large-scale (Qiagen Maxiprep$^R$ kit, Santa Clarita, Calif.) plasmids DNA purification kits according to the manufacturer's protocols (Qiagen, Santa Clarita, Calif.); Nuclease-free, molecular biology grade milli-Q water, Tris-HCl (pH 7.5), EDTA pH 8.0, 1M $MgCl_2$, 100% (v/v) ethanol, ultra-pure agarose, and agarose gel electrophoresis buffer were purchased from Life Technologies, Gaithersburg, Md. RE digestions, PCRs, DNA ligation reactions and agarose gel electrophoresis were conducted according to well-known procedures (Sambrook, et al., *Molecular Cloning: A Laboratory Manual*. 1, 2, 3; 1989); (Straus, et al., Proc Natl Acad Sci USA. March; 87(5): 1889-93; 1990). Nucleotide sequencing to verify the DNA sequence of each recombinant plasmid described in the following sections was accomplished by conventional automated DNA sequencing techniques using an Applied Biosystems automated sequencer, model 373A.

PCR primers were purchased from commercial vendors such as Sigma (St. Louis, Mo.) or synthesized using an Applied Biosystems DNA synthesizer (model 373A). PCR primers were used at a concentration of 150-250 µM and annealing temperatures for the PCR reactions were determined using Clone manager software version 4.1 (Scientific and Educational Software Inc., Durham, N.C.). PCRs were conducted in a Strategene Robocycler, model 400880 (Strategene, La Jolla, Calif.). The PCR primers for the amplifications were designed using Clone Manager® software version 4.1 (Scientific and Educational Software Inc., Durham N.C.). This software enables the design of PCR primers and identifies RE sites that are compatible with the specific DNA fragments being manipulated. PCRs were conducted in a thermocycler device, such as the Strategene Robocycler, model 400880 (Strategene), and primer annealing, elongation and denaturation times in the PCRs were set according to standard procedures (Straus et al, supra 1990). The RE digestions and the PCRs were subsequently analyzed by agarose gel electrophoresis using standard procedures (Straus et al, supra 1990; and Sambrook et al., supra 1989). A positive clone is defined as one that displays the appropriate RE pattern and/or PCR pattern. Plasmids identified through this procedure were further evaluated using standard DNA sequencing procedures, as described above.

*Escherichia coli* strains, such as DH5α and Stable2$^R$, were purchased from Life Technologies (Bethesda, Md.) and served as initial host of the recombinant plasmids. Recombinant plasmids were introduced into *E. coli* strains by electroporation using an high-voltage electropulse device, such as the Gene Pulser (BioRad Laboratories, Hercules, Calif.), set at 100-200Ω, 15-25 µF and 1.0-2.5 kV, as described (Straus et al, supra 1990). Optimal electroporation conditions were identified by determining settings that resulted in maximum transformation rates per mcg DNA per bacterium.

Bacterial strains are typically grown on tryptic soy agar (Difco, Detroit, Mich.) or in tryptic soy broth (Difco, Detroit, Mich.), which was made according to the manufacturer's directions. Unless stated otherwise, all bacteria were grown at 37° C. in 5% (v/v) $CO_2$ with gentle agitation. When appropriate, the media was supplemented with antibiotics (Sigma, St. Louis, Mo.). Bacterial strains were typically stored at −80° C. suspended in (Difco) containing 30% (v/v) glycerol (Sigma, St. Louis, Mo.) at ca. $10^9$ colony-forming units (herein referred to as "cfu") per ml.

Allelic exchange in BCG. The prior art teaches methods for introducing altered alleles into *Mycobacterium* strains and those skilled in the art will be capable of interpreting and executing the methods (Parish et al., *Microbiology*, 146:1969-1975; 2000). A novel method to generate an allelic exchange plasmid entails the use of synthetic DNA. The advantage of this approach is that the plasmid product will have a highly defined history and will be compliant, with federal regulations, whereas previously used methods, although effective, have poorly documented laboratory culture records and thus are unlikely to be compliant with federal regulations. Compliance with these regulations is essential if a product is to be licensed for use in humans by United States and European regulatory authorities.

A suicide vector for allelic exchange in *Mycobacterium* is a plasmid that has the ability to replicate in *E. coli* strains but is incapable of replication in *Mycobacterium* spp., such as M. tb and BCG. The specific suicide vector for use in allelic exchange procedures in the current invention is not important and can be selected from those available from academic (Parish et al., supra, 2000) and commercial sources. A preferred design of a suicide plasmid for allelic exchange is shown in FIG. 1. The plasmid is comprised of the following DNA segments: an oriE sequence for the plasmid to replicate in *E. coli* (Genebank accession #L09137), a Kanamycin-resistant sequence for selection in both *E. coli* and *Mycobacterium*

(Genebank accession #AAM97345), and an additional antibiotic selection marker, e.g. the zeocin-resistance gene (Genebank Accession #AAU06610), which is under the control of a *Mycobacterium* promoter (e.g. the hsp60 promoter). The second antibiotic selection marker is not essential but may be included to enable double selection to prevent outgrowth of spontaneous kanamycin-resistant isolates during the allelic exchange process.

Construction of such suicide vectors can be accomplished using standard recombinant DNA techniques. However, current regulatory standards (e.g. federal regulations) have raised the specter of introducing prion particles acquired from products exposed to bovine products containing BSE-infected material. To avoid introducing materials (e.g. DNA sequences) into the target strain of unknown origin, therefore, it is preferable that all DNAs in the suicide vector be made synthetically by commercial sources (e.g. Picoscript, Inc.). Accordingly, a preferred method for constructing suicide vectors is to assemble a plan of the DNA sequences using DNA software (e.g. Clone Manager), and then to synthesize the DNA on a fee-for-service basis by any commercial supplier that offers such a service (e.g. Picoscript Inc.). This procedure was used to design and obtain the suicide vector utilized in the Examples section below.

The configuration suicide vector described above (FIG. 1) has advantages, as this plasmid contains two antibiotic selection markers, thus minimizing selection of spontaneous mutants that display resistance to one antibiotic, which occurs at ca. $1/10^8$ per generation. Spontaneous resistance to two antibiotics is extremely rare and only occurs at ca. $1/10^{16}$ per generation. Thus, there is less that $1/10^6$ probability of double resistant strains emerging in the cultures used to execute the allelic exchange procedure.

For negative selection during allelic exchange process, a sacB gene (Genebank Accession #NT01BS4354), which imparts a sucrose-sensitive phenotype, can be included to enrich cultures with strains that have undergone the final DNA recombination step and completed the allelic exchange.

Cultivation of *Mycobacterium*. Selected BCG strains are cultured in liquid media, such as Middlebrook 7H9 or Saulton Synthetic Medium, preferably at 37° C. The strains can be maintained as static or agitated cultures. In addition, the growth rate of BCG can be enhanced by the addition of oleic acid (0.06% v/v; Research Diagnostics Cat. No. 01257) and detergents such as Tyloxapol (0.05% v/v; Research Diagnostics Cat. No. 70400). The purity of BCG cultures can be evaluated by evenly spreading 100 mcl aliquots of the BCG culture serially diluted (e.g. 10-fold steps from Neat—$10^{-8}$) in phosphate buffered saline (herein referred to PBS) onto 3.5 inch plates containing 25-30 ml of solid media, such as Middlebrook 7H10. In addition, the purity of the culture can be further assessed using commercially available medium such as thioglycolate medium (Science Lab, catalogue number 1891) and soybean-casin medium (BD, catalogue number 211768).

BCG seed lots are stored at −80° C. at a density of $0.1-2\times10^7$ cfu/ml. Typically, the liquid cultures are harvested at an optical density (600 nm) of 0.2-4.0 relative to a sterile control; the cultures are placed into centrifuge tubes of an appropriate size and the organisms are subjected to centrifugation at 8,000×g for 5-10 min. The supernatant is discarded and the organisms are resuspended in storage solution comprised of Middlebrook 7H9 containing 10-30% (v/v) glycerol at a density of $0.1-2\times10^7$ cfu/ml. These suspensions are dispensed into sterile 1.5 ml boron silicate freezer vials in 1 ml aliquots and then placed at −80° C.

Example 1

Construction of rBCG-PfoA Strains Capable of Escaping Endosome

Construction of rBCG-PfoA strains capable of escaping the endosome was carried out by allelic exchange of the flanking regions of the ureC gene. As a result, the PfoA gene segment replaced the ureC gene, allowing stable chromosomal expression of PfoA. Specific details are described below.

Figure 5:
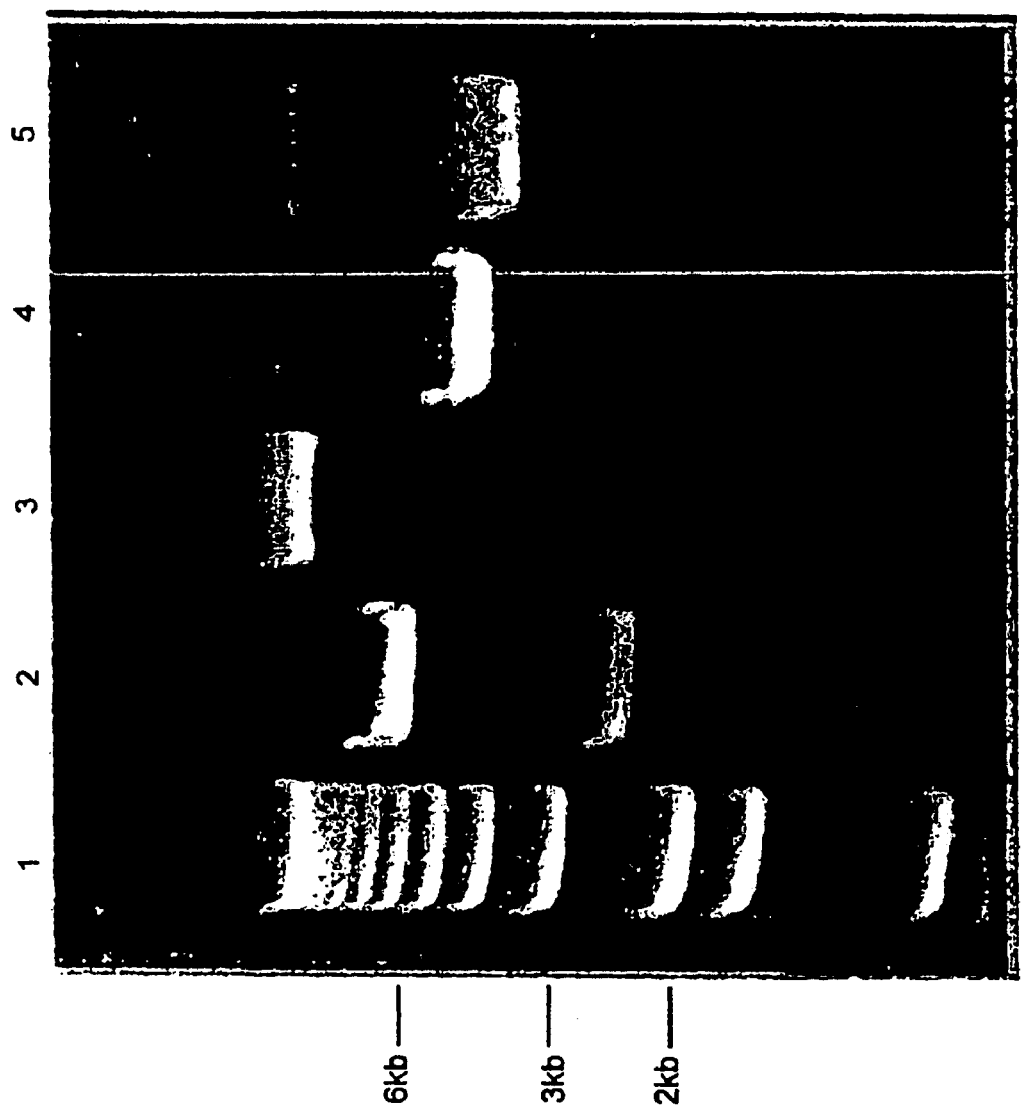

Construction of the Allelic Exchange Plasmid:

The allelic exchange plasmid is composed of the following DNA segments: An oriE sequence for the plasmid to replicate in *E. coli*, a kanamycin resistant gene sequence for selection in both *E. coli* and *Mycobacterium*, and an additional antibiotic selection marker (zeocin resistant gene), which is expressed by the Hsp60 promoter. The second marker was used to make a double selection, thus preventing spontaneous resistance to kanamycin during the process. For negative selection during the allelic exchange process, a sucrose sensitive gene was used. Finally, the left and right 1 kb flanking sequences of the ureC gene for the target BCG Danish 1331 strain were included with the PfoA gene in between. The PfoA gene is expressed under control of the Ag85B promoter. The Ag85B leader peptide sequence was used in place of the PfoA original secretion signal sequence for the secretion of PfoA. Finally, all these components were synthesized and assembled by Picoscript Inc (Houston, Tex.). The resultant plasmid is a mycobacterial suicide vector and the map for the plasmid that was obtained is as shown is FIG. 1. The resultant plasmid construct was confirmed as shown in FIG. 5.

Figure 4:
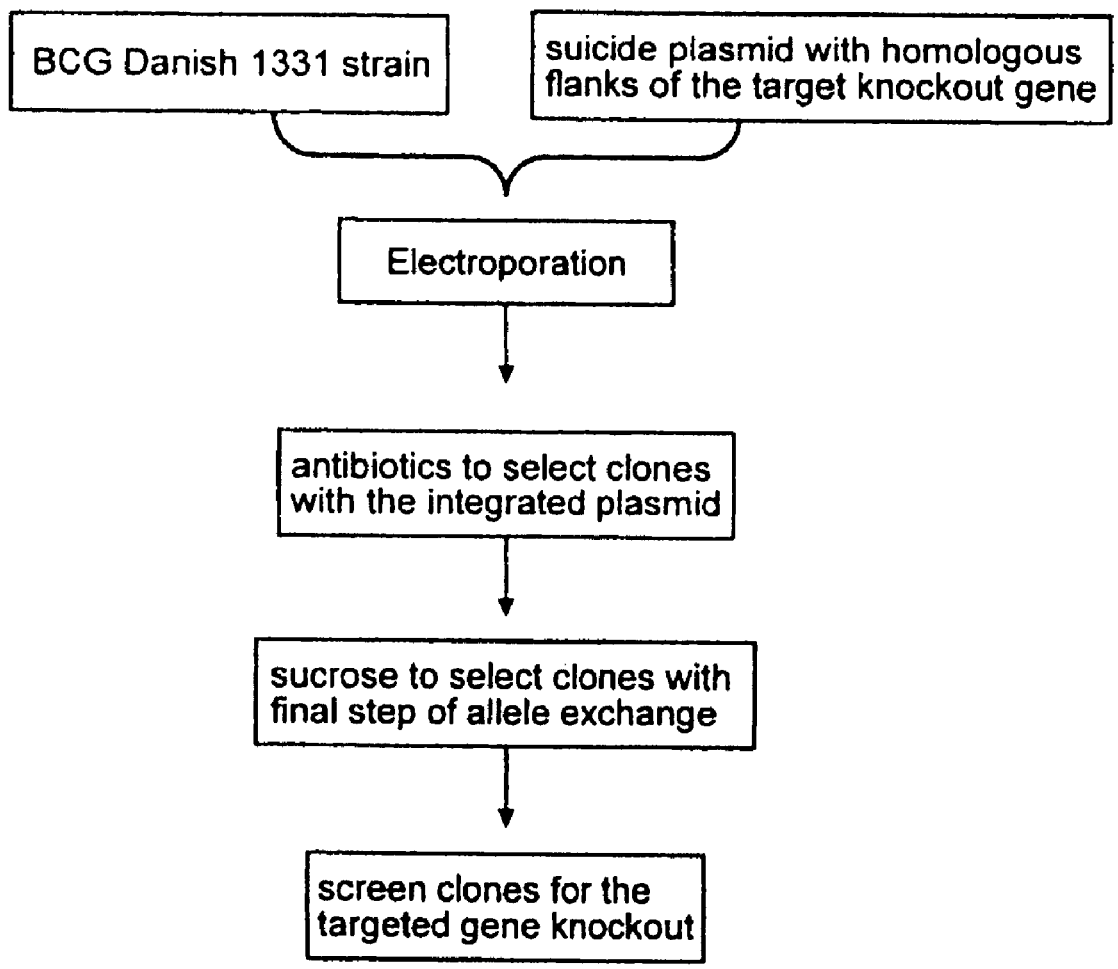

Introducing the Allele Exchange Plasmid into *Mycobacterium bovis* BCG Danish 1331 Strain The process of allele exchange is illustrated schematically in FIG. 4, which outlines the major steps of the procedure. Those steps are described in detail below.

BCG Danish 1331 was cultured in 7H9 medium with 10% of OADC (oleic acid-albumin-dextrose-catalase) (BD Gibco) and 0.05% (v/v) of Tyloxapol (research and diagnostic lab) supplementation. When the culture reached log phase, the bacteria were collected and prepared as described previously (Sun et al., 2004) for electroporation. Five micrograms of the allele exchange plasmid was introduced into freshly prepared electrocompetent cells using standard methodologies.

The above-constructed allelic exchange plasmid was introduced into *M. bovis* BCG Danish 1331 strain by the standard mycobacterial electroporation protocol for *Mycobacterium*. After electroporation, the cells were cultured overnight in 7H9 medium with 10% (v/v) OADC and 0.05% (v/v) of Tyloxapol supplementation. Then the cells were plated on 7H10 plates containing 50 ug/ml of both kanamycin and zeocin. The resultant colonies were picked and cultured in 7H9 medium containing 10% (v/v) of sucrose. The obtained culture was plated on 7H10 plates for cloning to obtain individual colonies, which were identified for the presence of PfoA gene in place of ureC. A flow chart outlining the main steps of this procedure is given in FIG. 4, and Table 1 describes the suicide vector, pAF 102, which is also depicted in FIG. 1.

TABLE 1

| Suicide vector used in the invention | | |
|---|---|---|
| Name | Backbone | Specific allele for allele exchange |
| pAF102 | pAF 100 | PfoA gene flanked by 1 kb flanks of ureC gene |

Example 1 shows that shows that the *Mycobacterium* BCG strain is genetically engineered to express a selected endosomolytic protein that is active at neutral pH, permitting escape of the *Mycobacterium* from endosomes into the cytoplasm of the cell.

Example 2

Validation of rBCG-PfoA Strain

Materials and Methods for Example 2.

Cultivation of *Mycobacterium*: For the following experiments, BCG strains were cultured at 37° C. in Middlebrook 7H9 media (BD biosciences) with 10% OADC supplementation. Tyloxapol (0.05% v/v, Research Diagnostics Cat. No. 70400) was used to disperse the bacteria. In experiments in which growth was compared between different strains, the optical density (600 nm) was measured at different times post inoculation. For testing sensitivity to kanamycin, the culture was prepared and growth was measured as above except kanamycin was added to a final concentration of 50 ug/ml. When solid medium was used to culture the bacteria, Middlebrook 7H10 agar (BD biosciences) was used. When appropriate, kanamycin was added to a final concentration of 50 ug/ml, and sucrose was added to a final concentration of 3%.

Urease activity test: The resultant colonies from the sucrose plates described in Example 1 were first screened for a lack of urease activity using a urease testing kit (BD Difico) according to the manufacture's instructions. Briefly, a loop full of bacteria was resuspended in the manufacture supplied test buffer in a transparent tube. BCG Danish 1331 strain was used as a urease positive control. Buffer alone was used as the negative control. The reaction mixture was incubated at room temperature for 30 minutes and the result was judged based on the manufacture's instruction.

Genotype analysis of rBCG strains carrying ΔureC:pfoA. PCRs with forward primer [acggctaccgtctggacat] (SEQ ID NO: 4) and reverse primer [cgatggcttcttcgatgc] (SEQ ID NO: 5) were performed to amplify the DNA sequence of the Pfo-specific insertion allele and BCG genomic DNA sequences flanking the ureC gene. The PCR parameters were as follows: Step 1: 95° C. 4 minutes one cycle; Step 2: 95° C. one minute, 60° C. 1 minute, and then 72° C. one minute for a total 30 cycles; Step 3: 72° C. 10 minutes with one cycle. Step 4: 4° C. storage. The resultant PCR products were analyzed by agarose gel electrophoresis and sequenced by automated dideoxynucleotide sequencing techniques, and the presence of a full-length PfoA gene in place of the ureC gene (i.e. ΔureC::PfoA) was confirmed.

Growth of AFV-102 in Macrophages: The growth of the rBCG strain AFV-102 in situ was tested in J774A.1 macrophage-like cells by determining mycobacterial colony-forming units (CFUs) in the infected macrophages. The efficacy of mycobacterial phagocytosis was determined by testing the intracellular CFU three hours after infection of J774A.1 cells. Subsequent long-term intracellular survival was performed by lysis of the cells to release the intracellular bacteria for numerating the CFU after washing with PBS five times, as previously described (Sun et al., 2004).

Analysis of the hemolytic activity of the expressed Pfo by AFV-102: To assess the secretion of PfoA by AFV-102, the strain was grown to mid-logarithmic phase as described above. Then the culture supernatants and the bacteria were collected. The AFV-102 bacterial pellet was re-suspended in 100 μl of PBS (pH 7.0) containing 0.1% BSA in a 96 well V-bottomed plate. To test if the PfoA protein was secreted into the culture supernatant, the liquid culture was spun down and the supernatant was used for the test. For testing the expressed PfoA for its pH independent hemolysis activity, the samples were prepared as above except PBS buffer with different pH values was used as the reaction buffer. 100 μl of 1% washed sheep erythrocytes was added to each well. The reaction was mixed gently and incubated at 37° C. for 1 h with agitation. BCG Danish 1331 strain bacterium was used as the hemolysis negative control. α-hemolysin (Sigma) with known units of hemolysin activity was used in serial dilution as the hemolysis positive control. At the end of incubation, the reaction was pelleted by centrifugation at 500 g for 15 minutes, and then the supernatant from the V-bottom plate was transferred into equivalent locations in a flat bottom 96-well plate and the optical density was measured (absorbance at 450 nm minus the absorbance at 540 nm). The hemolytic activity of the PfoA molecule was quantified by measuring the optical density of the color change after red cell lysis. The intensity of the color measured is in proportion to the amount of red cell lysis, which is then in proportion to the quantity of hemolysin. The sample values are then read off a standard curve through the use of known standards. Hemolytic units were defined as the dilution of the sample at which 50% of the sheep red blood cells were lysed.

Cytotoxicity of AFV-102 to macrophages: The cytotoxicity of the recombinant strain on J774A.1 macrophages (ATCC No. A TIB-67) was determined by measuring the Lactate Dehydrogenase (LDH) released from infected cells using a "Cell Titer 96 Aqueous One Solution Cell Proliferation Assay" kit (Promega, cat #: G3580) according to the manufacture's instruction. Briefly, the cells were infected with AFV-102 bacteria at the multiplicity of infection of 10. At different times post infection, the supernatant was measured for the amount of LDH released from the cells, which was then compared with that of the BCG Danish 1331 strain. Uninfected normal cells were used as the negative control. The percentage of viable cells was calculated based on the amount of LDH released from the infected cells to that of the negative control cells (100% cell viability).

Results for Example 2.

AFV-102 construction: During the construction of AFV-102, the selected merodiploid bacteria, which harbor the entire knockout plasmid on its chromosome via allelic exchange of its homologous DNA segment with that on the knockout plasmid, were cultured on sucrose-containing Middlebrook 7H10 plates for the final allelic exchange to replace the ureC gene by the PfoA expression cassette. Of the colonies produced on the sucrose plates, one colony Pfo-105-5 (renamed as AFV-102) was found to be urease negative, suggesting that the ureC gene had been replaced by the PfoA expression cassette. This bacterial colony was further subjected to genotype analysis by PCR for the genotype of ΔureC::ΩpfoA. The resultant PCR reaction was analyzed by gel electrophoresis on a 1.2% agarose gel, and the results are presented in FIG. 6. As can be seen, PCR using this bacterium as the template produced a PCR product of the expected size, which is larger than that of parental BCG Danish 1331 strain.

The expected size of the DNA band for the genotype of ΔureC::ΩpfoA is 2180 bps, while for parental BCG Danish 1331 strain is the size is 1967 bps. The PCR product for colony 105-5 was further gel purified and sequenced by the commercial sequencing facility of Johns Hopkins University (Baltimore, Md.). The sequencing result showed that this colony has the expected genotype of ΔureC::ΩpfoA. In addition, PCR targeted to amplify the Kanamycin gene and the sacB gene from the AFV-102 strain failed to produce any PCR product (data not shown). These findings suggest that AFV-102 has undergone the final allelic exchange step and has the desired genotype of ΔureC::ΩpfoA.

Figure 7:
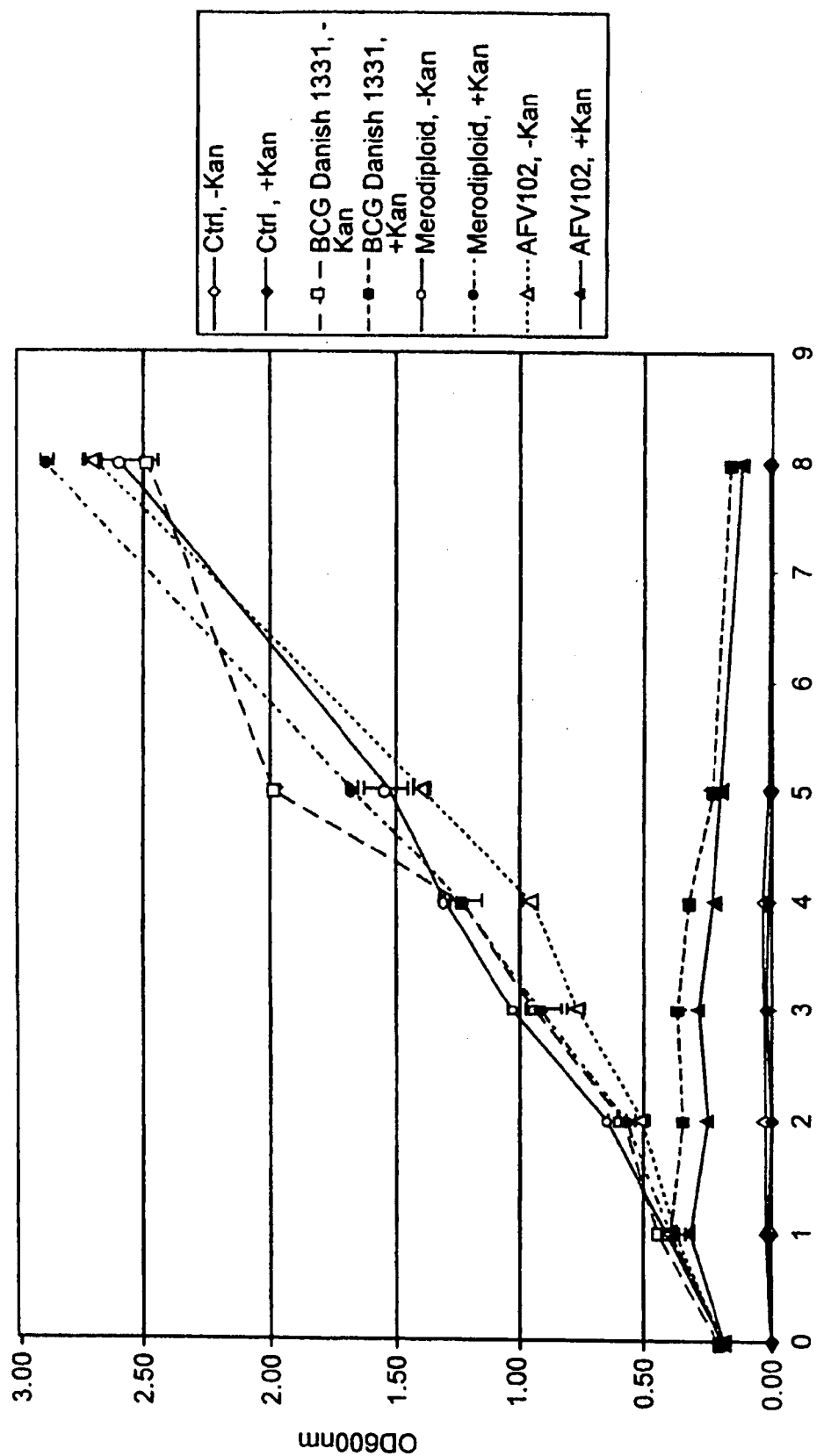

Growth characterization and kanamycin sensitivity test for AFV-102: Based on the urease activity test and genotyping results, clone 105-5 (renamed AFV-102) exhibited the expected phenotype and desired genotype of ΔureC::ΩpfoA. AFV-102 was then further tested for its ability to grow in 7H9 growth medium compared to that of the parental BCG Danish 1331 strain. The result is shown in FIG. 7. As can be seen, the AFV-102 construct has a very similar proliferation curve in 7H9 growth medium to that of the parental strain. In addition, in the presence of kanamycin, AFV-102 growth declined to a similar extent as that of the parental BCG Danish 1331 stain, suggesting that, as expected, it has a similar sensitivity to kanamycin.

Figure 8:
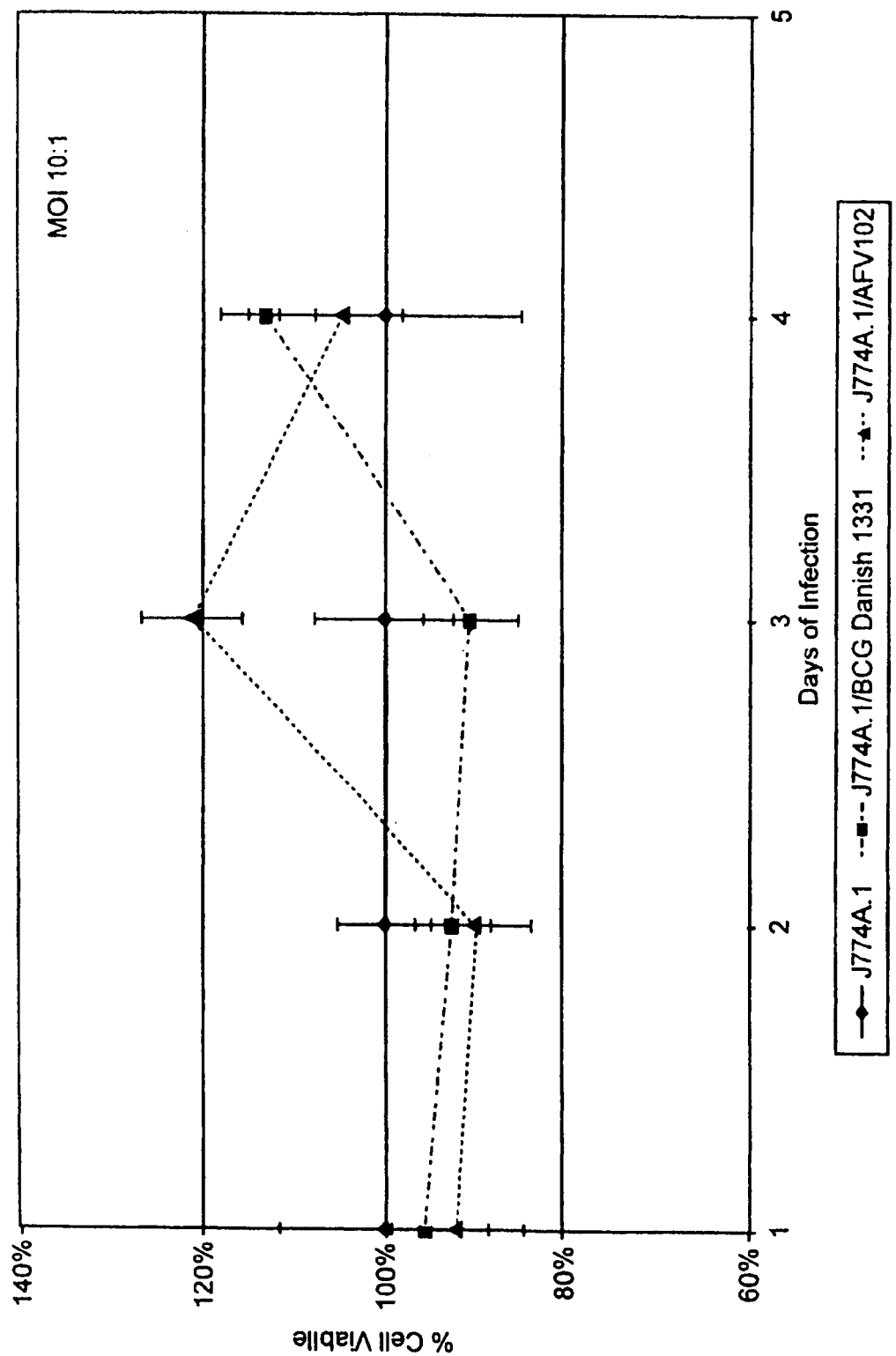

Cytotoxicity of AFV-102: It has been reported that a single amino acid change in the PfoA protein (codon 137 substitution mutation from gga, encoding Gly, to cag, encoding Gln) results in the loss of toxicity to mammalian cells. Yet the protein retains the capability of mediating bacterial escape from a vacuole (Portnoy supra, 1996). The toxicity of the protein expressed from AFV-102 was assessed by infecting J7741A cells with AFV-102 bacteria. When compared with the uninfected normal cell control at different time points after infection, AFV-102 did not cause any more significant cell death than the currently used BCG Danish 1331 vaccine strain (FIG. 8).

Figure 9:
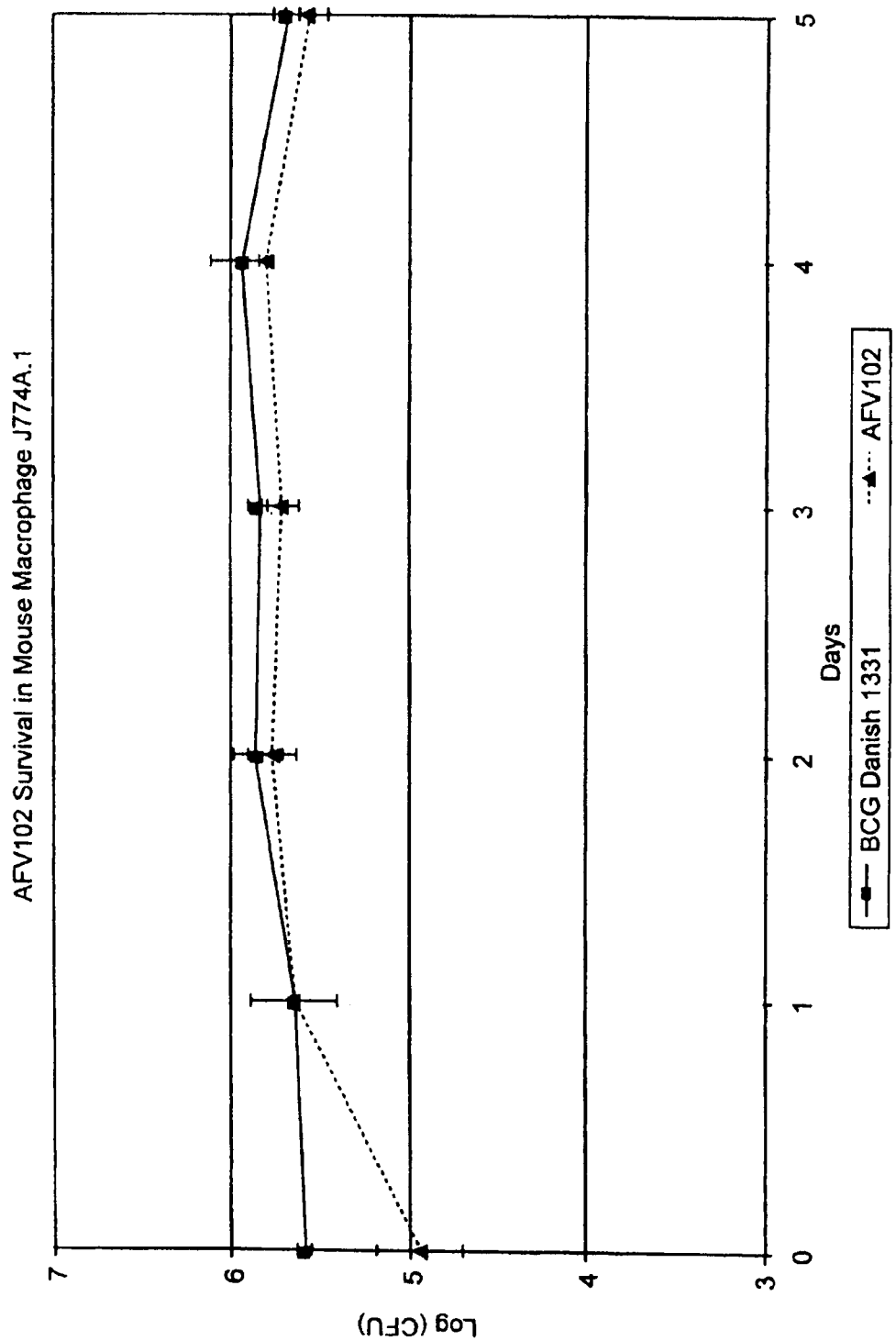

Survival in an alveolar macrophage cell line: To investigate if the construct is able to survival within macrophages, mid-log phase cultures were used to infect J774A.1 alveolar macrophages. Cells were infected with a multiplicity of infection (MOI) of 1:1. Intracellular survival of the *Mycobacterium* was monitored by plate counting the bacterium at various time intervals after infection. As may be seen in FIG. 9, the AFV-102 construct showed a persistence phenotype similar to that of the parental strain, suggesting no defect in intracellular survival for this construct in J774A.1 cells.

Figure 10:
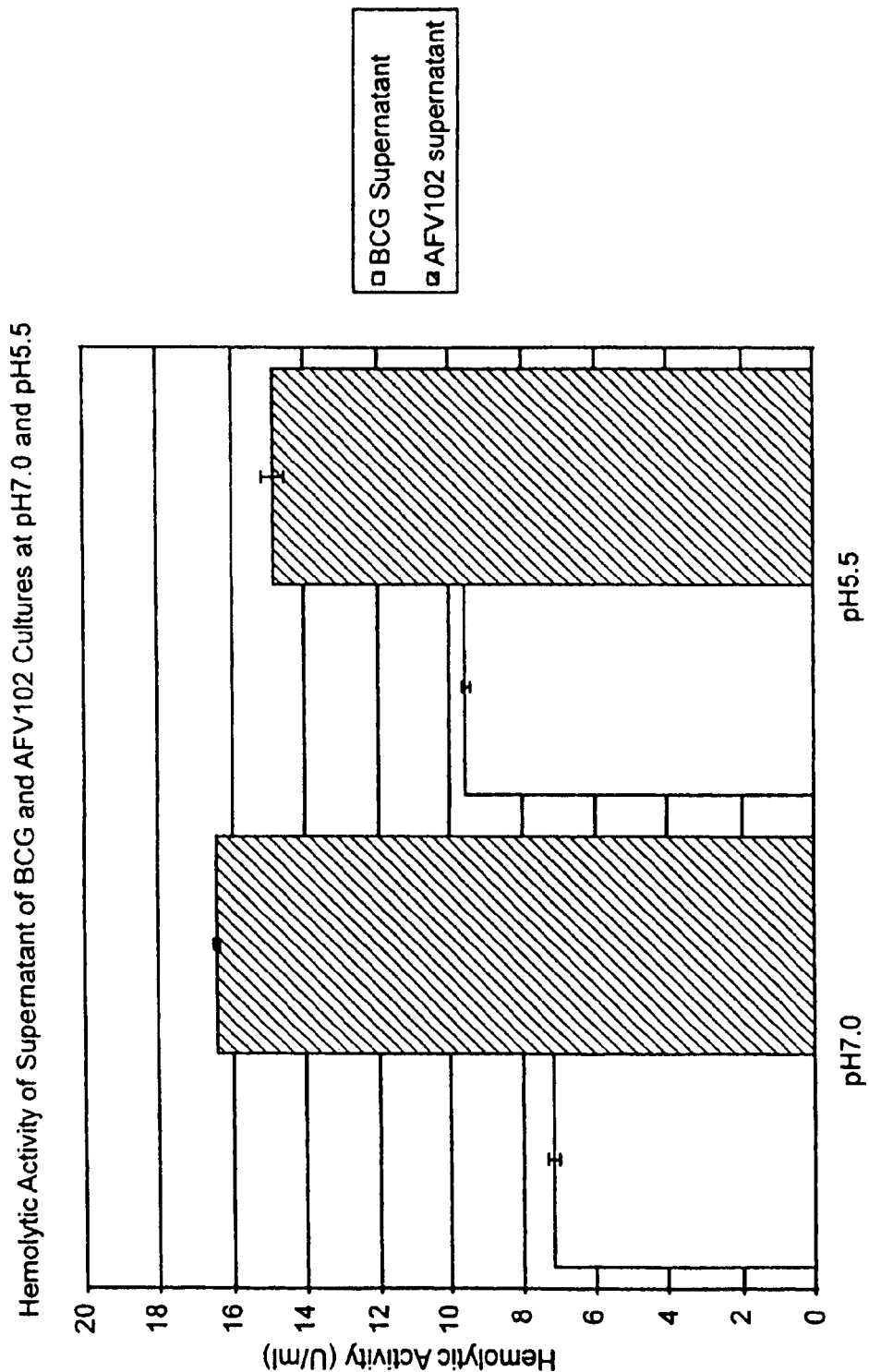

Secretion of the PfoA protein by AFV-102: Secretion of the PfoA protein by bacteria containing the AFV-102 construct was tested by measuring the bacterial culture supernatant for enhanced hemolytic activity compared to that of the BCG Danish 1331 strain. Culture supernatants for both AFV-102 and BCG Danish 1331 strain were harvested at the same optical density and compared for the ability to lyse red blood cells. The results are shown in FIG. 10. Consistent with the previous report, the BCG culture supernatant displayed a base-line level of hemolytic activity as a result of the bacteria releasing metabolites during growth, which may result in red cell lysis (Grode et al., *Journal of Clinical Investigation*, 115:2472-2479; 2005). In contrast, the AFV-102 culture supernatant had a significant higher level of hemolytic activity compared to that of the BCG Danish 1331 strain, consistent with the secretion of PfoA molecules into the culture supernatant. In addition, the pH independent hemolytic activity of the PfoA was further tested and compared at both pH 5.5 and 7.0, and the results are shown in FIG. 10. As can be seen, the supernatant from AFV-102 has a similar hemolytic capacity at both pH 5.5 and 7.0, suggesting that the hemolytic activity secreted by the PfoA protein is pH independent, as expected.

Example 2 shows that the constructed strain has the predicted biological activities, and that the Pfo that is manufactured by the strain is secreted and has pH independent activity.

Example 3 rBCG-PfoA Endosomal Escape and Animal Immunogenicity Test

A central paradigm of *Mycobacterium tuberculosis* pathogenesis is the arrest of phagosomal maturation. Armstrong and Hart (1971) established that *M. tuberculosis* phagosomes do not mix with ferritin-labelled lysosomes, referred to as the inhibition of phagosome-lysosome fusion. The vaccine strain *M. bovis* (BCG) was also found to reside in the phagosomal compartment, sequestered from the terminal endocytic organelles (Clemens and Horwitz, 1995; Hasan et al., 1997; Via et al., 1997). Clemens and Howitz (1995) found that the mycobacterial phagosomes persistently stain for transferrin receptor (TfR) at densities similar to those on the plasma membrane. The transferrin receptor is typically removed rapidly (t ½ in minutes) from endosomes and transported back to the plasma membrane; however, in mycobacterial phagosomes this process is halted and the phagosomes will contain the transferrin receptor. It is this phenomenon that allowed us to visualize phagosomes that contain mycobacteria. The phagosomes were labeled with antibodies to the transferrin receptor. At the same time, the mycobacteria were stained with a fluorescent dye that allows visual monitoring of the fate of the bacteria once inside the phagosome. The results showed that the rBCG-Pfo construct was able escape the endosome after infecting the cells.

Materials and Method for endosomal escape test: Bacteria and cells: BCG Danish 1331 and rBCG-ΔureC::ΩpfoA$_{G137Q}$ (AFV-102) were grown in 7H9 medium with 10% (v/v) OADC and 0.05% (v/v) of Tyloxapol supplementation (of the growth medium) to an OD$_{600}$ of about 0.8-1.0. Before infection, the bacterial cells were labeled with Alexa Fluor 568 succinimidyl ester (Molecular Probes, Eugene, Oreg.) in PBS at room temperature for 1-1.5 hours according to the manufacture's instruction. This dye forms very stable amide bonds to the primary amines located on proteins on the bacterial surface Briefly, 10 ml of the bacterial culture were pelleted and resuspended in 25 mls of 0.625 ug/ml of Alexa Fluor 568 in PBS (pH7.2) and incubated at room temperature for 1-1.5 hours to label the bacteria. The labeled bacterial cells were then washed three times with PBS and resuspended in 7H9 growth medium and stored in the refrigerator overnight. J774A.1 cells were cultured in DMEM medium as previously described (Sun et al, 2004) in 6 well cell culture plates on human fibronectin coated coverslips. The cells were plated at a density of 3×10$^6$ cells/well and cultured for 2 days in a 37° C. incubator with 5% CO$_2$ and humidity. During the infection, the labeled bacteria were pelleted and resuspended in DMEM+10% FBS medium and added directly to J774A.1 cells with a multiplicity of infection (MOI) of 10 for each cell. After 20 min, 8 hours and 24 hours, the cells were washed with room temperature (RT) phosphate buffered saline (PBS, pH 7.2). The cells were then fixed for 20 minutes at RT with 2% paraformaldehyde in PBS (pH 7.2). The fixed cells were then permeabilized with 0.1% Triton X-100 in PBS (pH 7.2) for 10 minutes at RT followed by washing twice with PBS (pH 7.2). Blocking was done for at least 2 hours at RT or overnight at 4° C. with 3% bovine serum albumin (BSA), 5% normal goat serum (NGS), and 0.5% sodium azide in PBS (pH7.2). Blocking buffer was removed and then rat anti-mouse transferring receptor-FITC (US Biological, Swampscott, Mass.) was added at a dilution of 1:50 in PBS (pH 7.2) containing 1% BSA, 3% NGS, and 0.5% sodium azide followed by incubation at RT for at least 1 hour. Cells were then washed 2-3 times with PBS and mounted with vectshield mounting media on glass slides. Analysis was done at a magnification of 1500 using a Nikon TE2000 inverted microscope equipped with a Retiga EXI Mono, 12 bit cooled, IR filtered digital camera for imaging.

Figure 11:
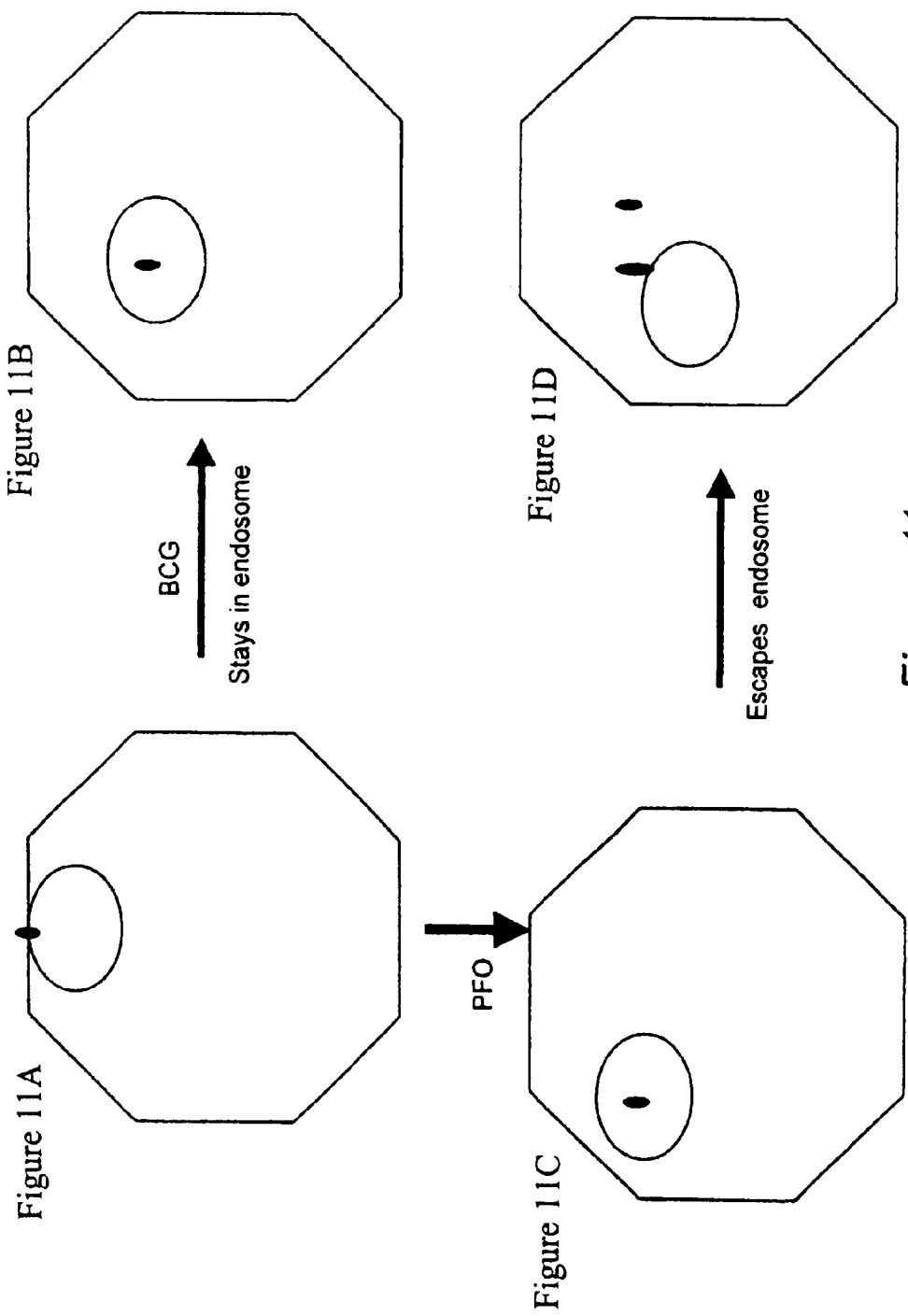

Result: When examined under the microscope, both BCG and rBCG-PfoA bacteria were found internalized by the host cells fifteen minutes after the infection, However, at 8 hours post infection, rBCG-PfoA bacteria were found outside the endosome, in contrast to BCG bacteria, which were found mostly located inside the host phagosome. These results are illustrated schematically in FIGS. 11A-D, which illustrate bacterial invasion of a macrophage (FIG. 11A), persistence of BCG within the endosome (FIG. 11B), AFV-102 bacterium within an early endosome (FIG. 11C) and AFV-102 bacteria escaping from the endosome into the cytoplasm of the cell (FIG. 11D) due to secretion of recombinant PfoA. Enumeration of the bacteria showed that 100 AVF102 out of 138 had escaped the endosome (72%) after 8 hours post infection, while only 29 BCG out of 100 (26%) had escaped the phagosome. Examination of the bacteria in the 24 hours post infection sample yielded a similar result. This finding shows that expression of PfoA increases the release of AVF 102 from phagosomes.

Further confirmation of this result was carried out using a different system in which a pH sensitive dye was used to label endosomes and lysozomes (Lysotracker-Red, Molecular probes, catalog number L-7528) under a similar experimental setting and procedure as above. Bacteria were visualized at wavelength emissions of 568, while phagosomes were visualized at wavelength emissions of 488. The result was consistent with the above observations.

Example 3 shows that recombinant strain AVF102 was capable of escaping the endosome while the BCG strain was much less efficient at escaping the endosome. Thus, strain AVF102 is much more likely to elicit a MHC-Class I immune response than is BCG, and would be useful in vaccine applications.

References for Example 3

Armstrong J, Hart P D. 1971. Response of cultured macrophages to *Mycobacterium tuberculosis*, with observations on fusion of lysosomes with phagosomes. *J Exp Med.* 134: 713-40.

*Mycobacterium tuberculosis* and *Legionella pneumophila* phagosomes exhibit arrested maturation despite acquisition of Rab7. *Infect Immun.* 68(9): 5154-66.

Hasan Z, Schlax C, Kuhn L, Lefkovits I, Young D, Thole J, Pieters J. 1997. Isolation and characterization of the mycobacterial phagosome: segregation from the endosomal/lysosomal pathway. *Mol Microbiol* 25(2): 427

Via L E, Deretic D, Ulmer R J, Hibler N S, Huber L A, Deretic V. Arrest of mycobacterial phagosome maturation is caused by a block in vesicle fusion between stages controlled by rab5 and rab7. *J. Biol. Chem.* 1997. 272(20): 13326-31.

Sun R, Converse P J, Ko C, Tyagi S, Morrison N E, Bishai W R. 2004. *Mycobacterium tuberculosis* ECF sigma factor sigC is required for lethality in mice and for the conditional expression of a defined gene set. *Mol. Microbiol.* 52(1): 25-38

Example 4

Formulation and Vaccination Strategies

The strategy for vaccine formulation is based on studies to determine maximum viability and stability throughout the manufacturing process. This includes determination of maximum organism viability (live to dead) during culture utilizing a variety of commonly used medium for the culture of *Mycobacteria* to include the addition of glycerol, sugars, amino acids, and detergents or salts. After culture, cells are harvested by centrifugation or tangential flow filtration and resuspended in a stabilizing medium that allows for protection of cells during freezing or freeze drying. Commonly used stabilizing agents include sodium glutamate, amino acids or amino acid derivatives, glycerol, sugars and commonly used salts. The final formulation will provide sufficient viable organisms to be delivered by intradermal, percutaneous injection, perfusion or oral delivery with sufficient stability to maintain an adequate shelf-life for distribution and use.

Preclinical Evaluation of TB Vaccines

General safety test BALB/c mice in groups of 6 are infected intraperitoneally with $2\times10^6$ CFU of the rBCG strain (s) of interest and the analogous parental strains. The animals are monitored for general health and body weight for 14 days post infection. Animals that receive the BCG and rBCG strains remain healthy, and neither lose weight nor display overt signs of disease during the observation period.

Virulence of novel rBCG strains in immunocompetent mice. Groups of 15 immunocompetent BALB/c mice are infected intravenously with $2\times10^6$ rBCG and BCG parental strains, respectively. At day 1 post infection, three mice in each group are sacrificed and CFUs in spleen, lung and liver are analyzed to ensure that each animal has an equal infection dose. At weeks 4, 8, 12, and 16 post-infection, three mice in each group are sacrificed and CFUs in spleen, liver and lung are obtained to assess the in vivo growth of the rBCG strains as compared to the parental BCG strain.

Stringent safety test in immunocompromised mice. Immunocompromised mice possessing the SCID (severe combined immunodeficiency) phenotype in groups of 10 are infected intravenously with $2\times10^6$ cfu rBCG and the parental BCG strain. At day 1 after infection, three mice in each group are sacrificed and cfu in spleen, liver and lung are assessed to verify the inoculation doses. The remaining seven mice in each group are monitored for general health and body weight. The survival of these mice is followed and the survival of rBCG-infected mice is compared to that of the parental strain infected animal during the entire observation period.

Guinea pig safety test. The safety of rBCG strains is also assessed in the guinea pig model in comparison to the parental BCG vaccine, which has a well-established safety profile in humans. First, the effect of the vaccine on the general health status of the animals, including weight gain, is examined. Guinea pigs are immunized intramuscularly with $10^7$ (100× of vaccination dose) CFU of the recombinant and parental strains, and the animals are monitored for general health and body weight for six weeks. Post mortem examination is performed for animals that die before the six weeks period. All animals are sacrificed at the end of six weeks post infection and gross pathology is performed. For confirmation under this test, no body weight loss and no abnormal behavior is observed, and all organs appear normal at six weeks necropsy, and/or no adverse health effects are observed for rBCG-PfoA vaccine, and rBCG-PfoA-vaccinated animals gain weight at the normal rate compared to the parental strain inoculated animals.

At the same time, bacterial levels in animal organs are monitored. Guinea pigs immunized with either the parental or recombinant vaccine are euthanized at various intervals after inoculation, after which the lungs, spleens, and regional (inguinal) lymph nodes are assayed for CFU of BCG or rBCG.

Toxicity test. To evaluate the toxicity of the rBCG strains, guinea pigs (12 in each group) are vaccinated intradermally with 1 dose, four times higher than the single dose or four times lower than the single dose of human use rBCG strains, BCG parental strain or saline. At day 3 post vaccination, six animals are sacrificed to access the acute effects of the vaccine on these animals. At day 28 post vaccination, the remaining six animals are sacrificed to evaluate the chronic effects on the animals. At both time points, the body weight of each animal is obtained, and gross pathology and appearance of the injection sites are examined. Blood is taken for blood chemistry, and the histopathology of the internal organs and injection sites is performed.

Murine protection study. C57Bl/6 mice (female, 5-6 weeks of age) in groups of 13 are immunized subcutaneously with $10^6$ CFU of rBCG, parental BCG or saline. Another group of mice is used as healthy controls. Eight weeks after immunization, mice are challenged with M. tb Erdman strain (or H37Rv Kan-resistant strain) by an aerosol generated from a 10-ml single-cell suspension containing a total of $10^7$ CFU of the challenge strain, a dose that delivers ~100 live bacteria to the lungs of each animal, as described previously (Brodin et al., J Infect Dis., 190(1): 115-122; 2004). The inoculated animals are monitored for survival along with unchallenged animals. Following the challenge, the animals are monitored for weight loss and general health. At day 1 after challenge, three mice in each group are sacrificed for lung CFU to confirm the challenge dose and one animal is sacrificed for spleen and lung histopathology. Five weeks after challenge, nine animals in each group are sacrificed, and histopathology and microbiology analysis of the animal is performed. Lung and spleen tissues from six mice are evaluated for CFU counts (plates with selection supplements are used to distinguish the vaccine strain from the challenge strain). If challenged with the H37Rv-kan resistant strain, Kan or TCH (thiophene-2-carboxylic acid hydrazide) is used to distinguish the challenge strain from the vaccine strain. If the M. tb Erdman strain is used to challenge, TCH is used to distinguish the vaccine strain from the challenge strain (BCG is susceptible, but M. tb is naturally resistant).

Induction of cutaneous delayed-type hypersensitivity (DTH). Specific pathogen free (SPF) guinea pigs are immunized intradermally with $10^3$ rBCG or BCG parental strains. Nine weeks after immunization, the animals are shaved over the back and injected intradermally with 10 μg of PPD (protein purified derivative) in 100 μl of phosphate buffered saline. After 24 hours, the diameter of hard induration (DTH) will be measured. rBCG strains induce DTH equal to or greater than that induced by parental BCG strains.

Guinea pig challenge study. To determine the efficacy of the rBCG vaccines against M. tb challenge, guinea pigs (young adult SPF Hartley, 250-300 grams, male) are immunized in groups of 12, each with rBCG, parental BCG strain or saline. The vaccines and controls are administered intradermally with $10^6$ cfu. At 10 weeks after immunization, the rBCG-, BCG- and sham-immunized animals are challenged by aerosol with the M tb by an aerosol generated from a 10-ml single-cell suspension containing a total of $10^7$ cfu of M tb; this procedure delivers ~100 live bacteria to the lungs of each animal, as described previously (Brodin et al., 2004). Following challenge, the animals are monitored for survival, weight loss and general health along with a healthy group of unvaccinated, unchallenged animals. Six animals in each group are sacrificed at 10 weeks post challenge and the remaining six in each group at 70 weeks post challenge for long-term evaluation. At both time points, histopathology and microbiology analysis of the animal are performed. Lung and spleen tissues are evaluated for histopathology and CFU count (plates with selection supplements are used to distinguish the vaccine strain from the challenge strain). If challenged with H37Rv-kan resistant strain, then Kan or TCH is used to distinguish the challenge strain from the vaccine strain. If the M. tb Erdman strain is used to challenge, TCH is then used to distinguish the vaccine strain from the challenge strain (BCG is susceptible but M tb is naturally resistant). For a successful challenge study, sham immunized animals die most rapidly after challenge, and the rBCG-immunized animals survive longer than the BCG parental strain immunized animals.

Primate safety and challenge study. More recently, non-human primates have been used for evaluation of vaccines against M tb. The evolutionary relationship between humans and non-human primates and the similar clinical and pathologic manifestations of tuberculosis in these species has made the non-human primate model attractive for experimental studies of TB disease and vaccine efficacy.

This model, characterized by the development of lung cavitation, appears to be applicable to human TB. The course of infection and disease is followed by X-ray and weight loss, as well as a variety of hematological tests, including erythrocyte sedimentation rate (ESR), peripheral blood mononuclear cell (PBMC) proliferation and cytokine production, cytotoxic T lymphocyte (CTL) activity, and antibody responses. Following infection, the cynomolgus monkey develops lung pathology with characteristic lesions, and, depending on the challenge doses, death from acute respiratory infection occurs within four-to six months after infection. Lower infection doses can lead to chronic infections without disease, much like in humans.

The study directly compares varying doses of the BCG parental strain versus recombinant BCG administered either alone or followed by two subsequent boosters with the vaccine comprising sequences that are over expressed in rBCG constructs. The latter is delivered by any of several known means, including but not limited to: as a recombinant protein based in a suitable adjuvant formulation, as DNA or as an Ad35 construct.

The first study evaluates the protective efficacy of the parental BCG vs rBCG constructs without a booster. This study comprises three groups with 10 animals in each group: one group each comprising BCG, rBCG and saline. Two animals from each group are skin tested with the over expressed antigens in the rBCG constructs as well as with standard PPD and saline as controls. A positive and larger induration in the rBCG group compared with the BCG is indicative of in vivo vaccine take and the elicitation of an immune response. The remaining eight animals from each group are aerosol challenged with low dose M. tb Erdman strain and protection is measured by reduction of bacterial burden at 16 weeks post challenge or with survival as the end point.

The follow up BCG prime protocol is essentially the same as above except that the animals are first vaccinated with BCG, rBCG and saline followed by two boosters with the over-expressed antigens.

The immunogenicity and protection study in the non-human primate model investigates immunobiological and immunopathological aspects of tuberculosis in macaques for efficacy studies on rBCG constructs. The animals are juvenile to young adults raised in captivity with an average weight of 2 to 3 kg that have been thoroughly conditioned prior to the start of the experiment. Pre-inoculation studies include baseline blood tests that include routine hematological studies and erythrocyte sedimentation rates as well as lymphocyte proliferation assays. Skin testing is done with PPD to ensure lack of sensitivity to tuberculin and chest x-rays are obtained as part of the pre-infection profile. The immunization period lasts 21 weeks in total, covering primary vaccination with BCG or rBCG at week=0, and antigen boosts at weeks 12 and 16. Antigen-specific immunity is assessed by measuring proliferation and interferon γ (IFN γ) secretion in lymphocyte stimulation tests. The frequency of IFN γ producing lymphocytes is determined by enzyme-linked immunosorbent assay (ELISPOT) or fluorescence-activated cell sorter (FACS). To this end, blood samples are drawn at weeks 0, 4, 8, 12, 16 and 20 weeks relative to primary vaccination.

Four to six weeks after the last immunization, animals are challenged by intratracheal installation of 3 ml (1,000 cfu) of the M. tuberculosis Erdman strain on the same day and with the same preparation. The course of the infection is assessed for weight loss, fever, elevated erythrocyte sedimentation rate (ESR), DTH to PPD, in vitro proliferative response of PBMC stimulated with PPD and antigen over-expression in rBCG followed by measurements of the levels of IFN-g production. Chest x-rays are performed to detect abnormalities consistent with pulmonary TB, and finally, necropsy at 12-16 weeks post challenge.

Clinical Evaluation of TB Vectors and Vaccines

Safety and toxicity studies Preclinical safety and toxicity studies as mandated by federal regulations are performed according to preclinical toxicology and safety studies as described above. Following these studies, human safety studies are performed. These studies are performed initially in healthy Quantiferon negative adults, followed by age de-escalation into children and neonates.

Immunogenicity studies: Immunogenicity studies in mice and primates utilize but are not limited to standard methods of evaluating cellular immunity such as INFγ, ELISPOT, flow cytometry with short and long term antigen or peptide stimulation, etc. Similar methodologies are utilized for evaluation of human responses. Tetramer studies are employed for evaluation of CD4 and CD8 responses following vaccination of humans.

Optimization of prime-boost strategies: rBCG performs well as a stand-alone vaccine against TB or other diseases for which it has been engineered to express relevant antigens. rBCG as described here as a vaccine for TB or expressing antigens to protect against other diseases also performs extremely well to prime the immune system for booster immunization with recombinant proteins mixed with adjuvants, or viral or bacterial vectored antigens. Both in animal preclinical studies and human studies the BCG primes followed by recombinant protein/adjuvant or vector boosts are optimized in terms of regimens and doses. These prime boost strategies are the most potent means for inducing immunity in humans because of the potency of the BCG prime embodied in the present invention, followed by focusing and enhancing the booster response of the immune system by recombinant protein or vector.

Post-exposure therapeutic vaccine studies in animals: C57BL/6 mice but not limited to this animal will be used for establishing latent infection; therapeutic vaccines will be given to the mice at the point when only negligible M. tb specific immunity has been induced by low dose infection and a later time point when M. tb specific immunity induced and has subsided and is predominated by memory T cells. Then, the therapeutic benefit of the vaccines will be assessed in mice 2 and 5 months after the last therapeutic vaccine delivery by enumerating cfu counts in lungs and spleens of individual mice. The cfu counts will be analyzed by standard statistical methods in the groups of mice and the results will be used to address whether therapeutic vaccination significantly reduces latent M. tb infection in mice. Similar methodologies are utilized for evaluation of responses of other animals when necessary.

Clinical evaluation of BCG vectors: oral administration of rBCG vaccines. Oral vaccination of the target animal with the rBCG of the present invention is achieved using methods previously described (Miller et al., *Can Med Assoc J.* 121(1): 45-54; 1979). The amount of the rBCG of the present invention administered orally will vary depending on the species of the subject, as well as the disease or condition that is being treated. Generally, the dosage employed is about $10^3$ to $10^{11}$ viable organisms, and preferably about $10^5$ to $10^9$ viable organisms.

The rBCG are generally administered along with a pharmaceutically acceptable carrier or diluent. The particular pharmaceutically acceptable carrier or diluent employed is not critical to the present invention. Examples of diluents include a phosphate buffered saline, buffer for buffering against gastric acid in the stomach, such as citrate buffer (pH 7.0) containing sucrose, bicarbonate buffer (pH 7.0) alone (Levine et al., J. Clin. Invest, 79:888-902; 1987; and Black et al., J. Infect. Dis., 155:1260-1265; 1987), or bicarbonate buffer (pH 7.0) containing ascorbic acid, lactose, and optionally aspartame (Levine et al., supra, 1989; Lancet, II: 467-470; 1988). Examples of carriers include proteins, e.g., as found in skim milk, sugars, e.g., sucrose, or polyvinylpyrrolidone. Typically these carriers would be used at a concentration of about 0.1-90% (w/v) but preferably at a range of 1-10% (w/v).

Example 5

Safety in Severe Combined Immunodeficiency (SCID) Mice

As mentioned earlier, expression of Llo in BCG proved relatively ineffective at promoting endosome escape, probably due to the low activity of Llo at neutral pH of the microenvironment of the modified endosome in which BCG resides (Hess, et al., Proc Natl Acad Sci 95:5299; 1998; Grode et al., J. Clin. Invest, J Clin Invest. 115(9): 2472; 2005). Nonetheless, the expression of Llo apparently modified the endosome sufficiently to reduce the virulence of BCG-Llo+ in SCID mice (Grode et al., 2005). This observation suggests that retargeting BCG to the cytoplasm of host cells has the potential of improving both the immunogenicity and safety of this antique live TB vaccine. The goal of this study, therefore, is to determine the safety of endosome-escape strain AFV-102 which express $PfoA_{G137Q}$ in SCID mice.

To this end, parent strains BCG Danish 1331 ($BCG_{1331}$) and the derivative of $BCG_{1331}$ that expresses $PfoA_{G137Q}$, strain AFV-102 were grown in 2 L flasks with agitation (150 oscillations per minute) to late-log phase (Optical density at 540 nm of 6.5-7.5). The bacteria were harvested by harvest by centrifugation and store at $1.5\times10^9$ cfu/ml at −80° C. in saline+0.05% (v/v) tyloxapol+10% (v/v) glycerol.

Inocula were prepared by thawing the above bulk vials on ice and making sets of serial dilutions in endotoxin-free (<0.05 EU/ml) normal saline (0.85% w/v NaCl). These dilutions were used to inoculate groups of 6 SCID mice subcutaneously with the respective doses shown in Table 2 suspended in a volume of 0.1 ml.

TABLE 2

Design of SCID mouse safety study

| Group | Vaccine | Dose |
|---|---|---|
| 1 | PBS | |
| 2 | $BCG_{1331}$ | $3 \times 10^4$ |
| 3 | $BCG_{1331}$ | $3 \times 10^5$ |
| 4 | $BCG_{1331}$ | $3 \times 10^6$ |
| 5 | $BCG_{1331}$ | $3 \times 10^7$ |
| 6 | AFV-102 | $3 \times 10^5$ |
| 7 | AFV-102 | $3 \times 10^6$ |
| 8 | AFV-102 | $3 \times 10^7$ |
| 9 | AFV-102 | $3 \times 10^8$ |

After inoculation, the mice are monitored for survival over a period of 100 days post-inoculation. The results of this study show that mice inoculated with AFV-102 survive longer than mice that receive the analogous dose of $BCG_{1331}$.

The use of a heterologous booster vaccine to bolster immunity elicited by BCG has gained attention recently. Thus, BCG-primed laboratory animals and humans develop impressive cellular immune responses following a heterologous boost comprised of modified vaccinia Ankara (MVA) encoding Mtb antigen 85A (herein "Ag85A"; also known as Rv3804c; Vordemeier et al., Immunol. 112(3): 461; 2004; McShane et al., Nature Med. 10(11): 1240; 2004); in contrast, naïve individuals develop relatively unimpressive responses to the MVA-Ag85A vector (McShane et al., 2004). Furthermore, there are independent studies showing that laboratory animals primed with BCG and boosted with either MVA-Ag85A (Williams et al., Infect Immun. 73(6): 3814; 2005) or subunit vaccine Mtb72f (Brandt et al., Infect. Immun. 72(11): 6622; 2004) develop greater levels of resistance to an Mtb challenge than that achieved by vaccination with BCG alone bolstered support for this approach. Although these studies did not define the correlates of protection, it is clear that heterologous prime-boost vaccination strategies offer an effective means to invoke protection against Mtb.

The goal of this and the following example, therefore, is to evaluate endosome-escape strain AFV-102 in a prime-boost vaccination regimen. The aim of the experiment in this example is to optimize the interval in a prime-boost regimen in which endosome-escape strain AFV-102 is used as the prime and a replication-deficient adenovirus serotype 35 vaccine vector (Vogels et al., J Virol. 77(15): 8263-71; 2003; Barouch et al., J. Immunol. 172(10): 6290; 2004) which harbors an expression cassette encoding a fusion protein comprised of Mtb genes Rv3804c-Rv1886-Rv0288 under the control of the cytomegalovirus early promoter (Vogels et al., J Virol. 77(15): 8263-71; 2003) is used as the boost. The boost is administered by the intranasal (in) route, since adenoviruses expressing TB antigens are more effective by this route than by conventional parenteral routes of administration (Wang et al., J. Immunol. 173(10): 6357; 2004).

Accordingly, groups of 10 SPF male Hartley guinea pigs (250-300 grams) are immunized as shown in table 3 so as to evaluate 14, 18 and 21 week prime-boost intervals.

TABLE 3

Guinea pig regimen study design

| Group | Prime I (Day 1) | Prime II (Week 3) | Prime III (Week 7) | Boost (Week 21) |
|---|---|---|---|---|
| 1 | Saline (id) | — | — | — |
| 2 | AFV-102 (id) | — | — | Ad35-TBS (in) |
| 3 | — | AFV-102 (id) | — | Ad35-TBS (in) |
| 4 | — | — | AFV-102 (id) | Ad35-TBS (in) |
| 5 | — | — | — | Ad35-TBS (in) |

Note:
Ad35-TBS denotes a replication-deficient adenovirus serotype 35 vaccine vector (Vogels et al., J Virol. 77(15): 8263-71; 2003; Barouche et al., J. Immunol. 172(10): 6290; 2004) which harbors an expression cassette encoding a fusion protein comprised of Mtb genes Rv3804c-Rv1886-Rv0288 under the control of the cytomegalovirus early promoter (Vogels et al., J Virol. 77(15): 8263-71; 2003).

The primes are administered intradermally at a dose of $10^6$ cfu in 0.1 ml of 10% glycerol. Control mice are given 0.1 ml 10% glycerol intradermally alone. At 14 weeks after the prime the guinea pigs are given a boost comprised of Ad35-TBS and are administered by intranasally at a dose of $10^9$ plaque forming units (i.e. Vogels et al., 2003; Barouch et al. 2004) suspended in 10 μl of PBS.

At 14 weeks after the boost, the animals are challenged by aerosol with Mtb strain Erdman by an aerosol generated from a 10-ml single-cell suspension containing a total of $10^7$ cfu of Mtb; this procedure delivers ~100 live bacteria to the lungs of each animal, as described previously (Brodin et al., 2004). At 5 weeks after the challenge, the animals in each group are sacrificed and the lungs and spleens are collected for histological and microbiological analysis. In the latter instance, lung and spleen tissues from the guinea pigs are evaluated for cfu counts. Since Mtb Erdman strain is used to challenge, TCH is added to the media to distinguish vaccine strain, which is sensitive to TCH, from the challenge strain.

The results of this study identify the optimal interval between the rBCG prime and the Ad35-TBS boost.

Example 6

Immunization Challenge

To measure the potency of candidate TB vaccine strain AFV-102 against Mtb challenge, groups of 8 (young-adult SPF Hartley guinea pigs (250-300 grams) are immunized as shown in Table 4.

TABLE 4

Guinea pig challenge study design

| Group | Prime (Day 1) | Boost (Week n*) | Challenge (Boost + 14 weeks) |
|---|---|---|---|
| 1 | Saline (id) | — | 100 cfu Erdman |
| 2 | BCG Danish 1331 (id) | — | 100 cfu Erdman |
| 3 | Saline (id) | Ad35-TBS (in) | 100 cfu Erdman |
| 4 | AFV-102 (id) | AFV-102 (id) | 100 cfu Erdman |
| 5 | AFV-102 (id) | Ad35-TBS (in) | 100 cfu Erdman |

Note:
1. n* denotes the interval between the prime and the boost will be the value defined in the preceding example.
2. Ad35-TBS denotes a replication-deficient adenovirus serotype 35 vaccine vector ((Vogels et al., J Virol. 77(15): 8263-71; 2003; Barouche et al., J. Immunol. 172(10): 6290; 2004) which harbors an expression cassette encoding a fusion protein comprised of Mtb genes Rv3804c-Rv1886-Rv0288 under the control of the cytomegalovirus early promoter (Vogels et al., J Virol. 77(15): 8263-71; 2003).

The primes in groups 4 and 5 are administered intradermally at a dose of $10^6$ cfu in 0.1 ml of 10% glycerol. Control mice in group 1 and 3 are given 0.1 ml 10% glycerol intradermally alone. Control mice in group 2, $10^6$ cfu of BCG Danish 1331 in 0.1 ml of 10% glycerol.

At 14 weeks after the prime the guinea pigs are boosted. In group 5, the boost is comprised of AFV-102 and is administered intradermally at a dose of $10^6$ cfu in 0.1 ml of 10% glycerol. In groups 4 and 6 the boosts are comprised of Ad35-TBS and are administered by intranasally at a dose of $10^9$ plaque forming units (i.e. Vogels et al., 2003; Barouch et al. 2004) suspended in 10 μl of PBS.

At 14 weeks after the final immunization, the animals are challenged by aerosol with the Mtb by an aerosol generated from a 10-ml single-cell suspension containing a total of $10^7$ cfu of Mtb; this procedure delivers ~100 live bacteria to the lungs of each animal, as described previously (Brodin et al., 2004). Following challenge, the animals are monitored for survival along with a healthy group of unvaccinated, unchallenged animals. The animals are also monitored for weight loss and general health.

The results of this study demonstrate that sham-immunized animals die most rapidly after challenge, animals vaccinated with BCG intradermally without a boost display an intermediate mean time to death and animals immunized with AFV-102 and boosted intranasally with Ad35-TBS survive the longest.

Example 7

Apoptosis

Apoptosis is programmed cell death that differs dramatically from necrotic cell death in terms of its induction and consequences. Apoptosis of cells containing foreign antigens is a powerful known stimulus of cellular immunity against such antigens. The process by which apoptosis of antigen containing cells leads to cellular immunity has sometimes been called cross-priming.[1, 2, 3] There are several mechanisms for induction of apoptosis which lead to increased antigen specific cell mediated immunity. Caspase 8 mediated apoptosis leads to antigen specific cellular immune protection.[4] Production of Caspase 8 in the cell cytoplasm by recombinant BCG who escape the endosome will be a powerful additional method for inducing programmed cell death in the context of foreign antigens expressed by the recombinant BCG, against BCG and other tuberculosis antigens over-expressed by the recombinant BCG as well as against antigens of BCG itself leading to high levels of antigen specific cellular immunity. Death receptor-5 (DR-5) also known as TRAIL-R2 (TRAIL receptor 2) or TNFR-SF-10B (Tumor Necrosis Factor-Superfamily member 10B) also mediates caspase 8 mediated apoptosis.[4] Reovirus induced apoptosis is mediated by TRAIL-DR5 leading to subsequent clearance of the virus.[5] Expression of DR-5 by recombinant BCG which escape the endosome should provide a potent adjuvant effect for induction of antigen specific cellular immunity against rBCG expressed antigens. Antigen expressing cells can also be induced to undergo apoptosis through Fas ligation, which is a strong stimulus for induction of antigen specific cellular immune responses.[6] Recombinant BCG escaping the endosome expressing Fas or Fas cytoplasmic domain/CD4 ectodomain fusion protein will induce apoptosis and antigen specific cellular immune responses.

The enhancement of cellular immunity by rBCG endosome escape strains or by rBCG endosome escape strains which produce additional enhancers of apoptosis described above is not limited to BCG antigens or antigens specifically coded for over-expression by rBCG but includes any antigen in the eukaryotic cell where the aforementioned rBCG can invade. As an example if such an rBCG is delivered to tumor cells where apoptosis is induced then cellular immunity against important tumor antigens will be induced with elimination, reduction or prevention of the tumor and/or metastasis. This anti-tumor effect will be in addition to the general anti-tumor effect that BCG generates when given locally such as the case with bladder cancer.

In a further embodiment of this invention, rBCG with endosome escape or rBCG with endosome escape enhanced by production of specific mediators of apoptosis, delivered inside tumor or other cells wherein such rBCG also produce foreign antigens against which strong cellular immune responses will be mounted will induce the production of strong cellular responses against those tumor cells or other eukaryotic cells containing these antigens. These cellular responses will lead to immune mediated tumor cell destruction, further cross priming and induction of cellular immunity against tumor or other important antigens with subsequent elimination, reduction or prevention of the tumor and/or metastasis. An example of such a foreign antigen is an HLA antigen different from the host cell HLA against which a strong heterologous cellular response will be mounted.

rBCG with endosome escape or rBCG with endosome escape whose apoptotic induction properties are enhanced by expression of specific mediators of apoptosis that also deliver specific tumor antigens will induce strong antigen specific cellular responses against these tumor antigens, including breaking of some tolerance for these antigens leading to elimination, reduction or prevention of tumors and/or metastasis without the need for direct delivery of the rBCG into the tumor itself.

Apoptosis following DNA damage or caspase 9 induces tolerance to certain antigens. Induction of tolerance is important in controlling or preventing autoimmune diseases such as but not limited to diabetes, rheumatoid arthritis, Crohns disease, inflammatory bowel disease and multiple sclerosis. Production of caspase 9 or other apoptosis mediated tolerance inducing proteins by rBCG escaping the endosome in cells such as but not limited to β pancreatic cells, colorectal and nerve cells will produce limited apoptosis which will induce tolerance against the antigen targets of autoimmunity in those cells thereby treating or preventing the autoimmune disease condition. Identification of specific antigens involved in autoimmune reactions will allow induction of tolerance against these autoimmune target antigens through endosome escape rBCG production of both these antigens and of caspase 9 or other molecules capable of inducing apoptotic mediated tolerance. Such rBCG will treat and/or prevent these autoimmune diseases.

References for Example 7

1. Heath, W. R., G. T. Belz, G. M. Behrens, C. M. Smith, S. P. Forehan, I. A., Parish, G. M. Davey, N. S. Wilson, F. R. Carbone, and J. A. Villandangos. 2004. Cross-presentation, dendritic cell subsets, and the generation of immunity to cellular antigens. *Immunol Rev* 199:9.
2. Gallucci, S., M. Lolkema, and P. Matzinger. 1999. Natural adjuvants: Endogenous activators of dendritic cells. *Nature Biotechnology.* 5:1249.
3. Albert, M. L., B. Sauter, and N. Bhadrdwaj. 1998. Dendritic cells acquire antigen from apoptotic cells and induce class I-restricted CTLs. *Nature* 392:86
4. Sheridan, J. P., S. A. Marsters, R. M. Pitti, A. Gruney, M. Skutbatch, D. Baldwin, L. Ramakrishnan, C. L. Gray, K. Baker, W. I. Wood, A. D. Goddard, P. Godowski, and A.

Ashkenazi. 1997. Control of Trail induced apoptosis by a family of signaling and decoy receptors. *Science* 277:818.
5. Clarke, P., S. M. Meintzer, S. Gibson, C. Widmann, T. P. Garrington, G. L. Johnson, and K. L. Tyler. 2000. Reovirus-induced apoptosis is mediated by TRAIL. *J Virol* 74:8135.
6. Chattergoon, M. A., J. J. Kim, J. S. Yang, T. M. Robbinson, D. J. Lee, T. Dentchev, D. M. Wilson, V. Ayyavoo, and D. B. Weiner. 2000. Targeted antigen delivery to antigen-presenting cells including dendritic cells by engineered Fas-mediated apoptosis. *Nat Biotechnology* 18:974.
7. Hugues, S., E. Mougneau, W. Ferlin, D. Jeske, P. Hofman, D. Homann, L. Beaudoin, D. Schrike, M. Von Herrath, A. Lehuen, and N. Glaichenenhaus. 2002. Tolerance to islet antigens and prevention from diabetes induced by limited apoptosis of pancreatic beta cells. *Immunity* 16:169.

Example 8

Figure 12:
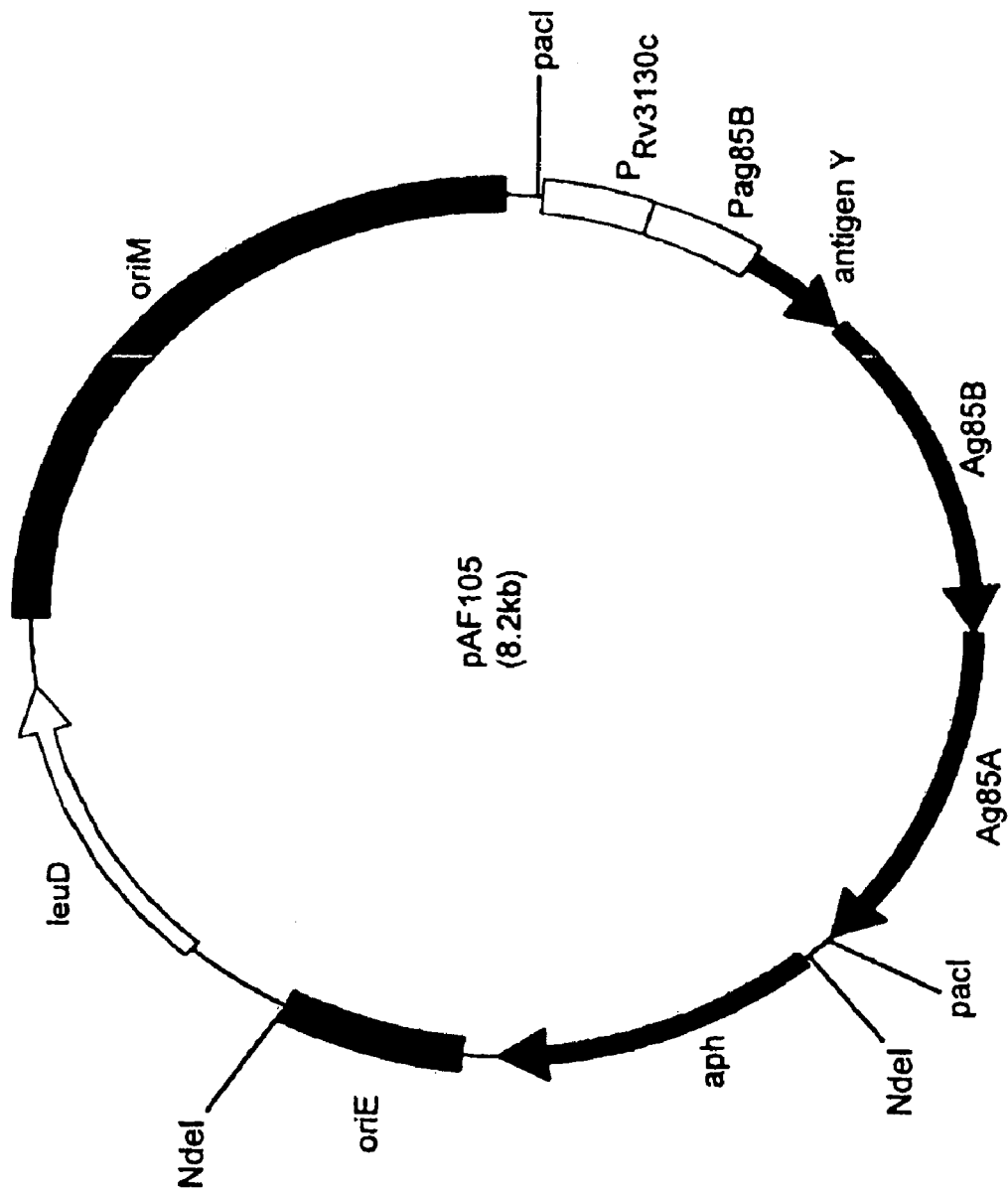

Over-Expression of Vaccine Antigens in an rBCG Strain Capable of Escaping the Endosome To over-express TB antigens into rBCG strain AFV-102, sequences encoding the Rv3031 promoter functionally linked to sequences encoding Rv3804c (also known as Ag85A), Rv1886 (also known as Ag85B) and Rv0288 (also known as TB10.4) were inserted into the PacI site of pAF100. The resulting plasmid, pAF105 (FIG. 12), was subsequently digested with restriction endonuclease NdeI to remove the *E. coli* replicon and kanamycin-resistance gene, and re-circularized by ligation with T4 ligase. This DNA (1-2 μg) was introduced into rBCG strain AFV-102 by electroporation. The bacteria were cultured in 8.75 cm plates containing 25-30 ml of solid media (Middlebrook 7H10). Following a pre-screen by PCR to detect colonies which harbor the antigen expression plasmid, a selected rBCG colony, which is both PfoA-positive and contains the TB antigen expression cassette, is designated AFV112 and is expanded to 500 ml in agitated liquid media (Middlebrook 7H9) at 37° C. Once the culture reaches late-log phase, glycerol is added to the 500 ml culture to a final concentration of 10% (v/v) and the premaster seed is stored in 5 ml aliquots at −80° C.

The purity of BCG and rBCG cultures are evaluated by evenly spreading 100 μl aliquots of the BCG culture serially diluted (e.g. 10-fold steps from Neat-$10^{-8}$) in phosphate buffered saline (PBS) onto 8.75 cm plates containing 25-30 ml of solid media (Middlebrook 7H10). PCR and restriction endonuclease analysis of plasmid DNA is used to confirm that the desired genotype is present in each rBCG isolate. In addition, PCR-generated DNA fragments are sequenced by automated dideoxynucleotide sequencing techniques to confirm the presence of full-length genes.

To assess the secretion of PfoA by AFV-102 and AFV112 harboring the TB antigen expression plasmid, both strains are grown to mid-logarithmic phase, as described above. The culture supernatants of these cultures are collected and filtered through 0.2-mm membrane filters, as previously described (Hess et al., Proc. Natl. Acad. Sci., 95:5299-304; 1998). The culture filtrate proteins then are assessed for hemolytic activity, as described above. The results show that AFV-102 and AFV112 display similar levels of hemolytic activity and that AFV112 retains the ΔureC::ΩpfoA$_{G137Q}$ allele and expresses a functional PfoA protein.

Finally, expression of the TB antigens is assessed in culture supernatants proteins separated on 10-15% SDS-PAGE gels. The results show increased expression of Rv3804c and Rv1886. Since Rv0288 is not expected to be over expressed in the culture supernatant, over expression of this 10 kDa protein, which is expressed on the same mRNA as Rv3804c and Rv1886, is inferred by the observation that Rv3804c and Rv1886 are over expressed.

Taken as a whole, this example demonstrates that it is possible to generate and rBCG strain which both expresses PfoA and over expresses TB antigens. Such as strain has potential to serve as a second generation TB vaccine.

Example 9

Further Comparative Studies

Based on the observations that individuals and animals with defects in IL-12, IFN-γ, and CD8+ T cell production are more susceptible to *Mycobacterium tuberculosis* infection and that presentation of antigens in the context of MHC I elicits the specific cellular immunity desired, we have created an improved rBCG that possesses carefully selected genetic modifications designed to alter and enhance its engendered cellular immune response and protective efficacy. This strain, designated AFV-102, takes a cue from the limited ability of BCG to escape the phagosomal compartments of infected cells as compared to Mtb and encodes a recombinant mutated perfringolysin (pfoA) allele introduced into the ureC locus of the chromosome. The pfoA gene encodes a G137Q substitution that dramatically reduces the cytosolic half life of the protein product and effectively eliminates cytotoxic activity as originally shown by Portnoy et al in *L. monocytogenes*. The mutant Pfo protein produced by AFV-102 similarly lacks cytotoxic activity, but retains the ability to perforate endosomal membranes, allowing the organism and its native or passenger antigens access to the cytosol such that its immunogenic molecules can be processed and loaded in a more desirable MHC class I manner. Perforation of the membrane may also release phagolysosomal proteases into the cytosol, leading to apoptosis and presentation of AFV-102 antigens by cross-priming, thus enhancing CD8+ cellular immune responses.

Immunofluorescent imaging of Aeras endosome escape rBCG AFV-102 revealed that it does indeed escape the phagosomal compartment of infected macrophages at a rate at least 40% greater than the parental BCG (not shown). CET studies further delineate the subsequent subcellular localization and interactions of AFV-102 after endosome escape.

SCID mouse studies conducted with antigen overexpressing derivatives of AFV-102 have shown the strain to be at least as safe as the parental BCG Danish 1331. Further, immunogenicity studies in mice and non-human primates have demonstrated the superior priming capacity of AFV-102 compared to the parental BCG Danish 1331. An rBCG strain with the ΔureC::pfo genotype carrying a plasmid encoding the overexpression of Ag85A, Ag85B, and TB 10.4, (designated AFRO-1) elicited a five-fold higher cellular immune response in a prime-boost animal model than the parental strain indicating its enhanced class I immune priming capacity as detailed below.

Figure 13A:
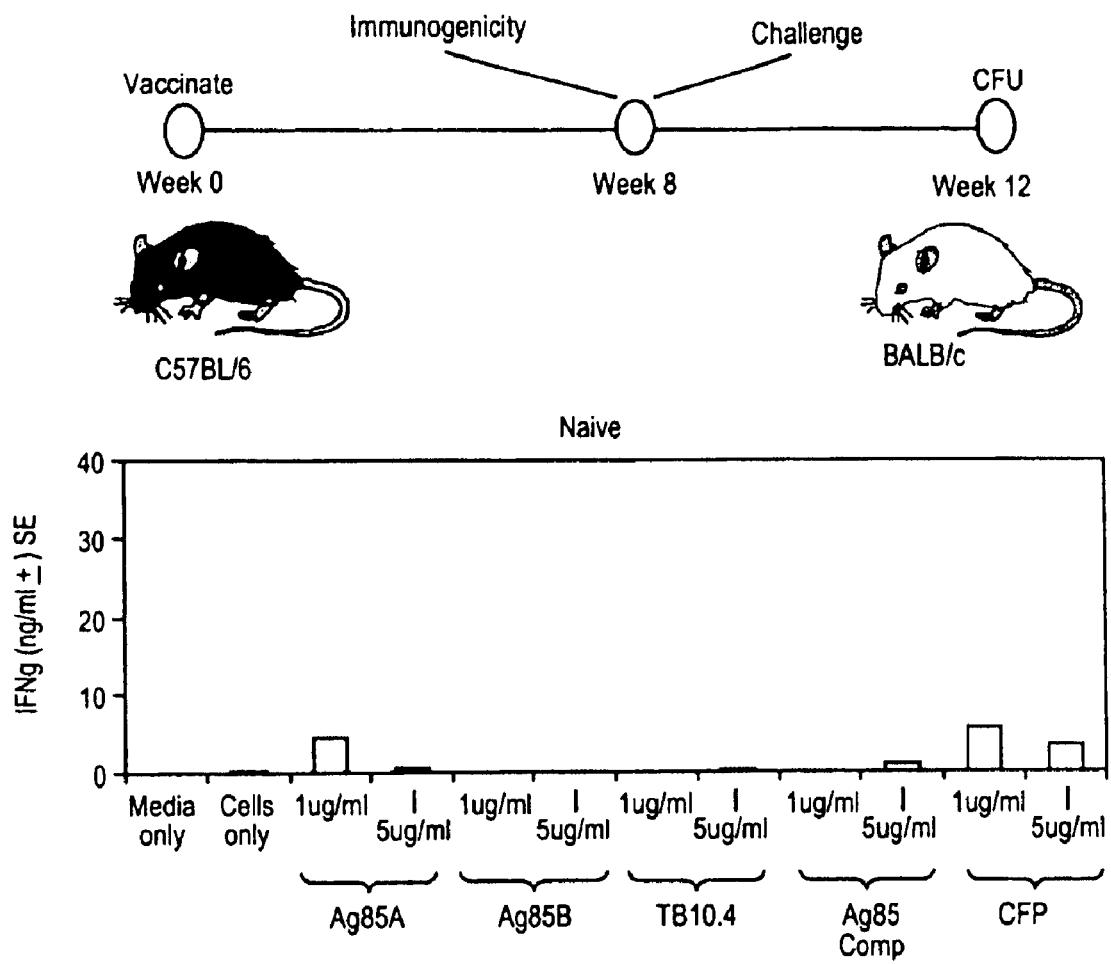
Figure 13B:
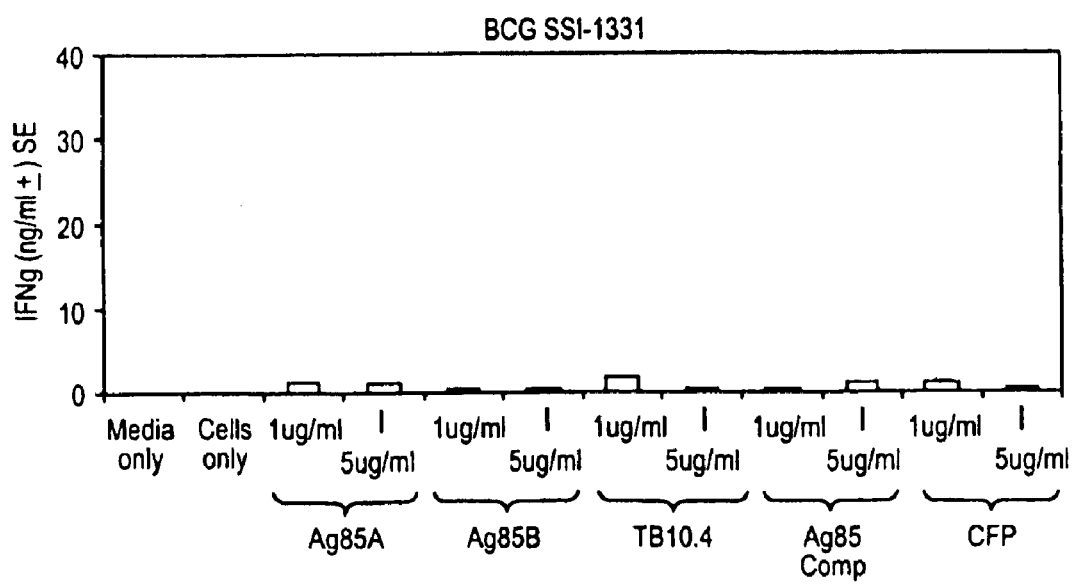
Figure 13C:
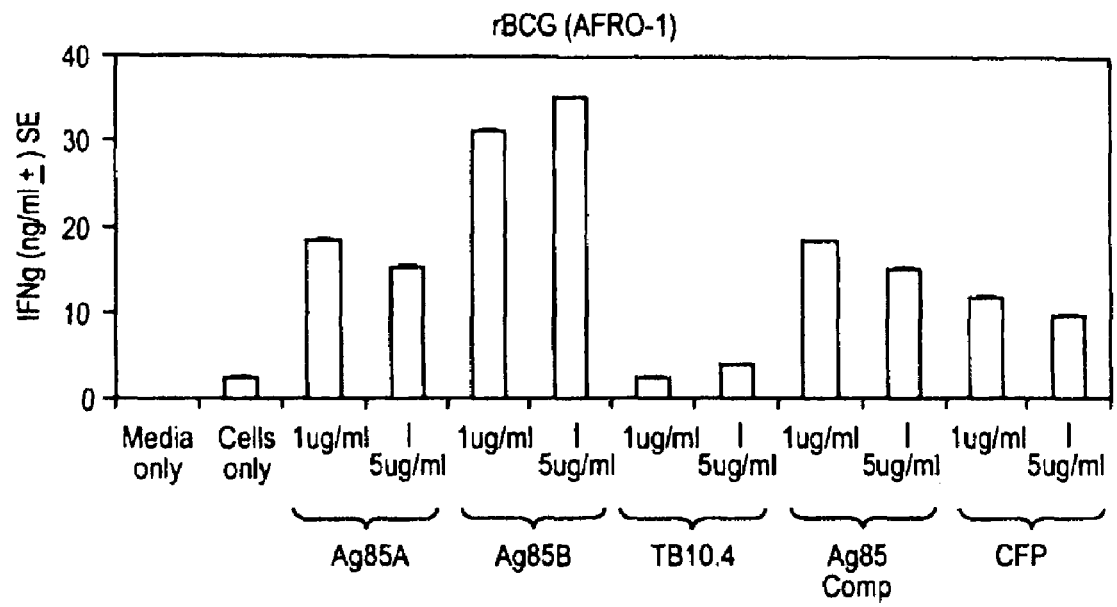
Figure 13D:
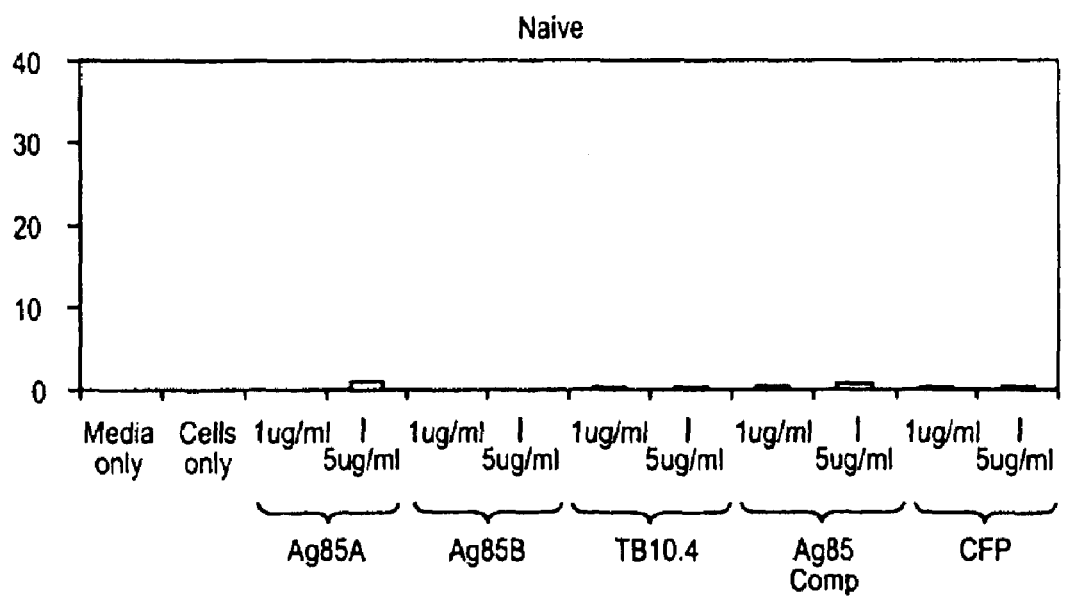
Figure 13E:
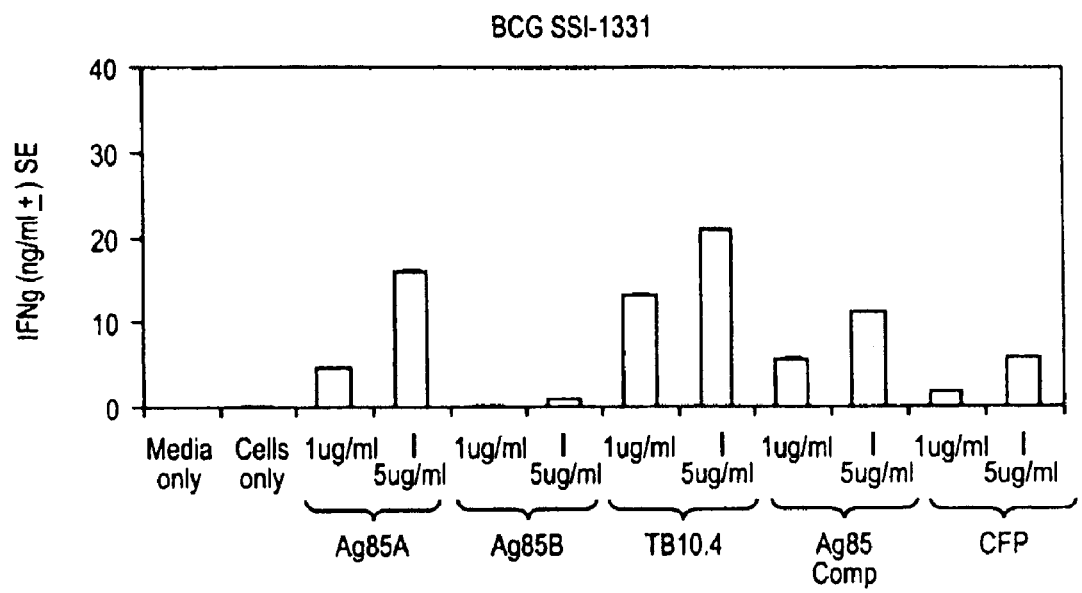
Figure 13F:
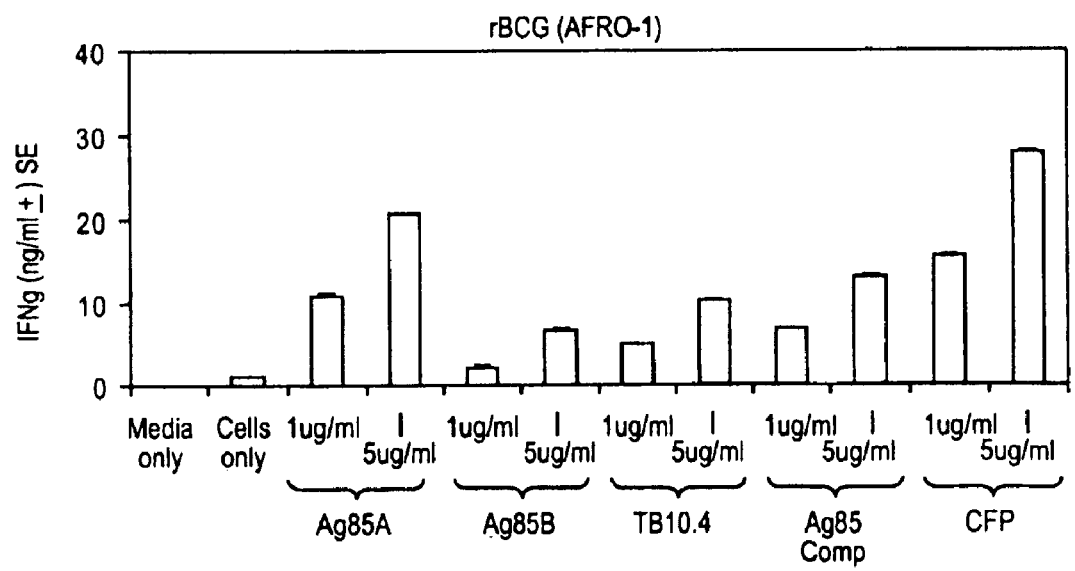

To compare the immunogenicity and protection of a derivative of AFV-102, AFRO-1, with BCG, both C57Bl/6 and BALB/c mice (15 mice/group) were immunized subcutaneously with 5×10 CFU of one or the other vaccine. Splenocytes were prepared from 3 mice/group 8 weeks later and evaluated for recall response to mycobacterial antigens by measuring IFN-γ in the supernatants after 3 days in culture (FIG. 13). The immune response to BCG was undetectable in C57Bl/6 mice (FIG. 13B). However, AFRO-1 elicited substantial IFN-γ responses to mycobacterial antigens in splenocytes from both C57Bl/6 as well as BALB/c mouse strains (FIGS. 13C and 13F). While BCG induced a substantial IFN-γ response in BALB/c mice (FIG. 13E), unlike in C57Bl/6 mice (FIG. 13B), AFRO-1 enhanced the response to CFP in particular, perhaps due to the more complex makeup of CFP compared to that of individual antigens.

The remaining 12 mice/group from this experiment (FIG. 14) were challenged with virulent *M. tuberculosis* by aerosol 8 weeks after vaccination with either BCG or AFRO-1 rBCG. Despite the enhanced immunogenicity of AFRO-1 over BCG, both BCG and AFRO-1 vaccinations resulted in a significant and roughly equivalent reduction in mycobacterial load in the lungs (FIG. 14A, C) and the spleen (FIG. 14B, D) in both C57Bl/6 and BALB/c mouse strains.

We also compared the protective effect of AFRO-1 and AFV-102 with that of BCG in BALB/c mice when the interval between vaccination and challenge was extended from 8 to 17 weeks (FIG. 15). After 17 weeks, the vaccinated mice were challenged with aerosolized *M. tuberculosis* and sacrificed 13 weeks later to determine bacterial burdens (FIG. 15). All vaccine strains elicited equivalent protection in both the lungs (FIG. 15A) and the spleens (FIG. 15B), with each reducing the number of mycobacteria by approximately 1 log compared to that in unvaccinated animals. Although there were no clear advantages to rBCG over BCG or to AFRO-1 over AFV-102 in terms of protection, this may merely reflect limitations in the mouse model for evaluating tuberculosis vaccines.

We thus extended these studies to determine the immunogenicity and protection of AFRO-1 rBCG in guinea pigs. Guinea pigs (20 animals/group) were vaccinated with a single dose of either BCG or AFRO-1 rBCG. After 10 weeks, 3 animals/group were sacrificed to evaluate immune response using RT-PCR to measure the expression of IFN-γ (FIG. 16A), TNF (FIG. 16B) and IL-10 (FIG. 16C).

Figure 6:
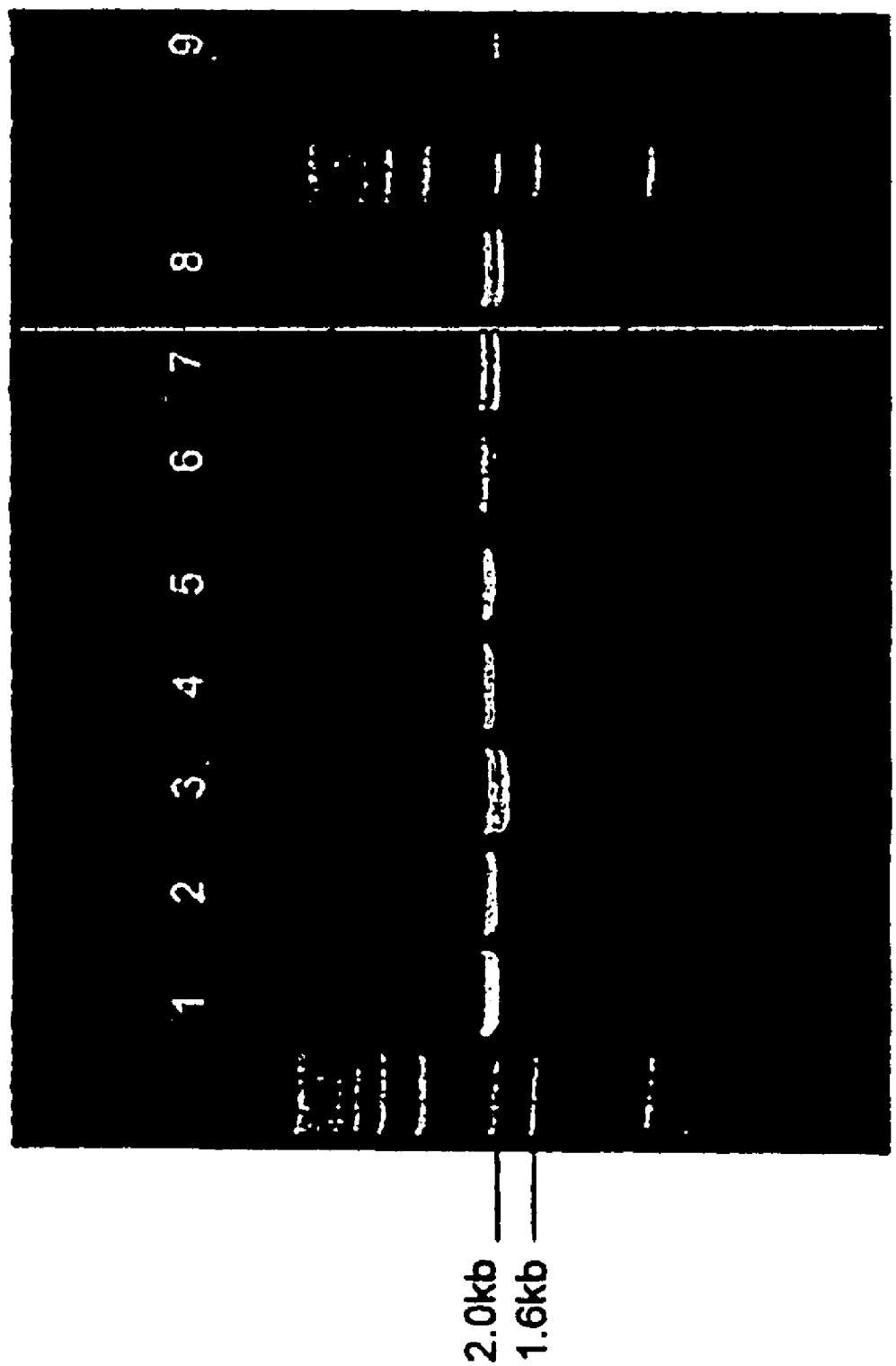

Lung cells and splenocytes from BCG-vaccinated guinea pigs expressed very little IFN-γ in response to individual mycobacterial antigens although they did respond to stimulation with the more complex PPD (FIG. 16A). In contrast, lung cells from animals vaccinated with AFRO-1 had greatly increased expression levels of IFN-γ in response to all 3 mycobacterial stimuli while substantial responses to three of the antigens were observed in splenocytes from AFRO-1-vaccinated animals (FIG. 16A). TNF expression in lung cells and splenocytes was only slightly induced above baseline in response to single mycobacterial antigens although substantial up-regulation of TNF transcription was noted in splenocytes following PPD stimulation (FIG. 16B). Finally, the expression of IL-10 was most strongly induced when Ag85A was used to stimulate splenocytes from AFRO-1-vaccinated guinea pigs (FIG. 16C). The remaining 17 guinea pigs in each group were challenged and sacrificed 10 weeks later to enumerate the bacterial burden in the lung and spleens of the animals. While the number of mycobacteria per organ varied dramatically from animal-to-animal, both AFRO-1 and BCG conferred protection against *M. tuberculosis* challenge (FIG. 6).

Ten weeks after vaccination, the remaining 17 guinea pigs/ group were challenged by aerosol with *M. tuberculosis* Erdman and 10 weeks post challenge, bacterial loads in the lung (FIG. 17A) and spleen (FIG. 17B) were determined As can be seen, both BCG and AFRO-1 rBCG conferred similar degrees of protection in this study. Thus, AFRO-1 rBCG appears to be safe, more immunogenic than BCG in both mice and guinea pigs and at least as protective as BCG.

"Prime-boost" vaccine strategies using heterologous vaccines induce stronger cellular immune responses than either a single vaccination or a booster vaccine with the same, homologous, vaccine. Thus, for potential pediatric vaccine regimens, subjects will be primed with an improved, recombinant BCG strain and then boosted with another vaccine candidate. Having previously shown that a recombinant Ad35-vectored TB vaccine (Ad35-TBS, a replication-deficient adenovirus type 35 vaccine vector encoding a fusion of Ag85A-Ag85B-TB10.4 that has been shown to be safe and immunogenic in animals and humans) could boost immunity in BCG-primed mice, we evaluated whether a greater effect could be attained when mice were first primed with rBCG AFRO-1. Accordingly, mice were primed with either BCG or AFRO-1 then, 10 weeks later, the same mice received a single i.m. boost of Ad35-TBS and the immune response to mycobacterial antigens was evaluated 1 week later (FIG. 18A-E). Splenocytes from mice that received only a BCG or AFRO-1 prime made little IFN-γ when stimulated in vitro with mycobacterial antigens (FIGS. 18B, C). In contrast, splenocytes from BCG-primed mice boosted with a single dose of Ad35-TBS made substantially more IFN-γ upon in vitro stimulation (FIG. 18D). However, an Ad35-TBS boost of mice primed with AFRO-1 elicited splenocytes that produced much more IFN-γ upon stimulation than splenocytes from mice similarly primed with BCG (compare FIGS. 18D to E). Additionally, we analyzed splenocytes from these mice after in vitro stimulation with overlapping mycobacterial peptides using intracellular staining (ICS). While in vitro stimulation with protein antigens followed by IFN-γ ELISA 3 days later preferentially evaluates CD4+ T cell responses, ICS following peptide stimulation assesses better CD8+ T cell IFN-γ responses. This analysis demonstrated that priming with AFRO-1 induced a larger CD8+ T cell response 1 week post Ad35-TBS boost than did BCG (FIG. 19). Thus, our AFRO-1 rBCG exhibits superior immunogenicity compared to BCG when used to prime mice that are subsequently boosted with Ad35-TBS. The advantage of AFRO-1 in this regimen is reflected by assays that preferentially evaluate CD4+ T cells responses (FIG. 18) as well as those that measure CD8+ T cells (FIG. 19).

The findings in the mouse model showing the immunogenicity of AFRO-1 rBCG to be better than that of BCG (FIGS. 18 and 22) are extended to compare AFRO-1 with BCG in guinea pigs when boosted with two (rather than one) doses of Ad35-TBS (FIG. 20). As part of a larger study, groups of 32 guinea pigs were primed with either BCG or rBCG AFRO-1. One control group (#1) of 17 animals received only saline injections while the other control group (#2) received only a single vaccination with BCG. Groups #3 and 4 were boosted i.m. with Ad35-TBS 14 weeks following priming with BCG or AFRO-1, respectively, and boosted again 16 weeks later. Following these vaccine regimens, all animals will be infected by aerosol with the virulent Erdman strain of *M. tuberculosis* and monitored for over 1 year during which survival, bacterial burdens and pulmonary pathology will be evaluated (FIG. 20). Thus, this study will provide important efficacy data that compares vaccination regimens using BCG or AFRO-1 rBCG for priming when boosted with Ad35-TBS.

A similar study has been undertaken to evaluate the immunogenicity and protective efficacy of several candidate vaccine regimens in non-human primates (FIG. 21). One arm of this study directly compares the immunogenicity of BCG with that of AFRO-1 when boosted twice with Ad35-TBS (FIG. 21A, Groups 1 and 2).

As shown in FIG. 22, animals primed with AFRO-1 (Group 2) generated greater prime responses to Ag85A and Ag85B as measured by the difference between antigen-specific lymphoproliferative responses before and after boosting with Ad35-TBS. These animals have been challenged with virulent M tb Erdman and will be followed for protection.

The studies in this example show the enhancement of MHC Class I immune responses of the endosome escape strain, AFV-102, and derivatives such as AFRO-1, when compared to the parental BCG, and have demonstrated the utility of such constructs as candidate vaccines.

While the invention has been described in detail, and with reference to specific embodiments thereof, it will be apparent to one of ordinary skill in the art that various changes and modifications can be made therein without departing from the spirit and scope thereof.

We claim:

1. A recombinant *Mycobacterium* that is genetically engineered to include a nucleic acid sequence that encodes an expressable and secretable Prefringolysin O (PFO) protein that is active at a pH of 6-8.

2. The recombinant *Mycobacterium* of claim 1, further comprising nucleic acid sequences that encode one or more proteins of interest.

3. The recombinant *Mycobacterium* of claim 2, wherein said one or more proteins of interest include one or more *Plasmodium* antigens.

4. The recombinant *Mycobacterium* of claim 1, wherein said recombinant *Mycobacterium* is an attenuated *Mycobacterium*.

5. The recombinant *Mycobacterium* of claim 4, wherein said attenuated *Mycobacterium* is Bacille Calmette Guerin (BCG).

6. The recombinant *Mycobacterium* of claim 5, wherein said BCG is BCG Danish 1331.

7. The recombinant *Mycobacterium* of claim 1, wherein said nucleic acid sequence that encodes an expressable and secretable PFO protein is present in a chromosome of said recombinant *Mycobacterium*.

8. The recombinant *Mycobacterium* of claim 1, wherein said nucleic acid sequence that encodes an expressable and secretable PFO protein replace a urease C gene in a chromosome of said recombinant *Mycobacterium*.

9. The recombinant *Mycobacterium* of claim 2, wherein said nucleic acid sequences that encode one or more proteins of interest are present in a chromosome of said recombinant *Mycobacterium*.

10. The recombinant *Mycobacterium* of claim 2, wherein said one or more proteins of interest of interest include *Mycobacterium tuberculosis* (Mtb) antigens.

11. The recombinant *Mycobacterium* of claim 10, wherein said Mtb antigens are selected from the group consisting of Ag85A, Ag85B, TB 10.4, Rv0125, Rv0203, Rv0287, Rv0288, Rv0603, Rv1196, Rv1223, Rv1271c, Rv1733c, Rv1738 Rv1804c, Rv1886, Rv2031c, Rv2032, Rv2253, Rv2290, Rv2389c, Rv2626c, Rv2627c, Rv2779c, Rv2873, Rv2875, Rv3017c, Rv3407, Rv3804c, Rv3810, and Rv3841.

12. The recombinant *Mycobacterium* of claim 2, wherein said nucleic acid sequences that encode one or more proteins of interest are present on a plasmid.

13. A composition comprising a recombinant *Mycobacterium* that is genetically engineered to include: a nucleic acid sequence that encodes an expressable and secretable Prefringolysin O (PFO) protein that is active at a pH of 6-8; and nucleic acid sequences that encode one or more proteins of interest.

14. The composition of claim 13, wherein said one or more proteins of interest of interest include *Mycobacterium tuberculosis* (Mtb) antigens.

15. The composition of claim 14, wherein said Mtb antigens are selected from the group consisting of Ag85A, Ag85B, TB 10.4, Rv0125, Rv0203, Rv0287, Rv0288, Rv0603, Rv1196, Rv1223, Rv1271c, Rv1733c, Rv1738 Rv1804c, Rv1886, Rv2031c, Rv2032, Rv2253, Rv2290, Rv2389c, Rv2626c, Rv2627c, Rv2779c, Rv2873, Rv2875, Rv3017c, Rv3407, Rv3804c, Rv3810, and Rv3841.

16. The composition of claim 13, wherein said nucleic acid sequences that encode one or more proteins of interest are present on a plasmid.

17. The composition of claim 13, wherein said recombinant *Mycobacterium* is an attenuated *Mycobacterium*.

18. The composition of claim 17, wherein said attenuated *Mycobacterium* is Bacille Calmette Guerin (BCG).

19. The composition of claim 18, wherein said BCG is BCG Danish 1331.

20. The composition of claim 13, wherein said nucleic acid sequence that encodes an expressable and secretable PFO protein is present in a chromosome of said recombinant *Mycobacterium*.

21. The composition of claim 13, wherein said nucleic acid sequence that encodes an expressable and secretable PFO protein replace a urease C gene in a chromosome of said recombinant *Mycobacterium*.

22. The composition of claim 13, wherein said nucleic acid sequences that encode one or more proteins of interest are present in a chromosome of said recombinant *Mycobacterium*.

23. The composition of claim 18, wherein said composition is a vaccine.

24. The composition of claim 23, wherein said vaccine is a vaccine for *Mycobacterium tuberculosis*.

25. The composition of claim 13, wherein said composition further comprises an adjuvant.

26. The composition of claim 13, wherein said composition further comprises a pharmacologically suitable carrier.

27. The composition of claim 13, wherein said one or more proteins or interest include *Plasmodium* antigens.

* * * * *